US00RE46724E

(19) United States
(12) Reissued Patent
Rossignol et al.

(10) Patent Number: US RE46,724 E
(45) Date of Reissued Patent: *Feb. 20, 2018

(54) HALOALKYL HETEROARYL BENZAMIDE COMPOUNDS

(71) Applicant: Romark Laboratories, L.C., Tampa, FL (US)

(72) Inventors: Jean-Francois Rossignol, St. Petersburg, FL (US); J. Edward Semple, Tampa, FL (US)

(73) Assignee: Romark Laboratories, L.C., Tampa, FL (US)

( * ) Notice: This patent is subject to a terminal disclaimer.

(21) Appl. No.: 15/156,580

(22) Filed: May 17, 2016

Related U.S. Patent Documents

Reissue of:
(64) Patent No.: 9,126,992
Issued: Sep. 8, 2015
Appl. No.: 14/451,637
Filed: Aug. 5, 2014

U.S. Applications:
(62) Division of application No. 12/777,383, filed on May 11, 2010, now Pat. No. 8,846,727.

(60) Provisional application No. 61/177,626, filed on May 12, 2009.

(51) Int. Cl.

| | |
|---|---|
| ***A61K 31/415*** | (2006.01) |
| ***A61K 31/4168*** | (2006.01) |
| ***A61K 31/4196*** | (2006.01) |
| ***A61K 31/421*** | (2006.01) |
| ***A61K 31/4245*** | (2006.01) |
| ***A61K 31/427*** | (2006.01) |
| ***A61K 31/433*** | (2006.01) |
| ***C07D 231/38*** | (2006.01) |
| ***C07D 233/38*** | (2006.01) |
| ***C07D 249/14*** | (2006.01) |
| ***C07D 261/14*** | (2006.01) |
| ***C07D 263/48*** | (2006.01) |
| ***C07D 271/07*** | (2006.01) |
| ***C07D 285/125*** | (2006.01) |
| ***C07D 417/12*** | (2006.01) |
| ***C07D 233/88*** | (2006.01) |
| ***C07D 233/90*** | (2006.01) |
| ***C07D 271/113*** | (2006.01) |
| ***C07D 275/03*** | (2006.01) |
| ***C07D 277/46*** | (2006.01) |
| ***C07D 277/56*** | (2006.01) |
| ***C07D 285/08*** | (2006.01) |
| ***C07D 285/135*** | (2006.01) |
| ***C07D 403/06*** | (2006.01) |
| ***C07D 403/12*** | (2006.01) |
| ***C07D 405/12*** | (2006.01) |
| ***C07D 409/06*** | (2006.01) |
| ***C07D 413/12*** | (2006.01) |
| ***C07D 417/06*** | (2006.01) |
| ***A61K 31/506*** | (2006.01) |
| ***A61K 31/497*** | (2006.01) |
| ***A61K 31/454*** | (2006.01) |
| ***C07D 401/12*** | (2006.01) |
| ***A61K 45/06*** | (2006.01) |
| ***C07D 231/40*** | (2006.01) |
| ***C07D 231/44*** | (2006.01) |

(52) U.S. Cl.
CPC ..... *C07D 417/12* (2013.01); *A61K 31/4196* (2013.01); *A61K 31/427* (2013.01); *A61K 31/4245* (2013.01); *A61K 31/433* (2013.01); *A61K 31/454* (2013.01); *A61K 31/497* (2013.01); *A61K 31/506* (2013.01); *A61K 45/06* (2013.01); *C07D 231/40* (2013.01); *C07D 231/44* (2013.01); *C07D 233/88* (2013.01); *C07D 233/90* (2013.01); *C07D 249/14* (2013.01); *C07D 261/14* (2013.01); *C07D 263/48* (2013.01); *C07D 271/07* (2013.01); *C07D 271/113* (2013.01); *C07D 275/03* (2013.01); *C07D 277/46* (2013.01); *C07D 277/56* (2013.01); *C07D 285/08* (2013.01); *C07D 285/135* (2013.01); *C07D 401/12* (2013.01); *C07D 403/06* (2013.01); *C07D 403/12* (2013.01); *C07D 405/12* (2013.01); *C07D 409/06* (2013.01); *C07D 413/12* (2013.01); *C07D 417/06* (2013.01)

(58) Field of Classification Search
None
See application file for complete search history.

(56) References Cited

U.S. PATENT DOCUMENTS

| | | | |
|---|---|---|---|
| 3,950,351 | A | 4/1976 | Rossignol et al. |
| 4,337,081 | A | 6/1982 | Gay |
| 4,343,945 | A | 8/1982 | Gay |

(Continued)

FOREIGN PATENT DOCUMENTS

| | | | |
|---|---|---|---|
| CA | 2618646 | A1 | 11/2007 |
| EP | 0 343 894 | B1 | 6/1992 |

(Continued)

OTHER PUBLICATIONS

Allen et al., "Identification and Characterization of Mutations in Hepatitis B Virus Resistant to Lamivudine," Hepatology, 1998, 27(6):1670-1677.
Amadi et al., "Effect of nitazoxanide on morbidity and mortality in Zambian children with cryptosporidiosis: a randomized controlled trial," The Lancet, Nov. 2, 2002, 360:1375-1380.
Blight et al., "Efficient Initiation of HCV RNA Replication in Cell Culture," Science, Dec. 8, 2000, 290:1972-1974.
Blight et al., "Efficient Replication of Hepatitis C Virus Genotype 1a RNAs in Cell Culture," Journal of Virology, Mar. 2003, 77(5):3181-3190.
Boyer et al., "Synthesis and photosynthetic inhibition activity of substituted 5-(bis-trifluoromethyl)methyl)-2-aminothiazoles," Journal of Fluorine Chemistry, 2006, 127:1522-1527.

(Continued)

*Primary Examiner* — Jerry D Johnson
(74) *Attorney, Agent, or Firm* — Foley & Lardner LLP

(57) ABSTRACT

A new class of haloalkyl heteroaryl benzamides is described. These compounds show strong activity against hepatitis viruses.

18 Claims, No Drawings

(56) References Cited

U.S. PATENT DOCUMENTS

| | | | | |
|---|---|---|---|---|
| 4,416,683 | A | 11/1983 | Burow, Jr. | |
| 5,169,846 | A | 12/1992 | Crooks | |
| 5,578,621 | A | 11/1996 | Rossignol | |
| 6,020,353 | A | 2/2000 | Rossignol | |
| 6,117,894 | A | 9/2000 | Rossignol | |
| 6,136,835 | A | 10/2000 | Camden | |
| 6,849,254 | B1 | 2/2005 | Brass et al. | |
| 7,241,781 | B2 * | 7/2007 | Barrish et al. | 514/342 |
| 7,285,567 | B2 | 10/2007 | Rossignol | |
| 7,285,576 | B2 | 10/2007 | Hyde et al. | |
| 8,124,632 | B2 | 2/2012 | Rossignol et al. | |
| 8,541,457 | B2 | 9/2013 | Fu et al. | |
| 8,846,727 | B2 | 9/2014 | Rossignol et al. | |
| 8,895,752 | B2 | 11/2014 | Rossignol et al. | |
| 9,023,877 | B2 | 5/2015 | Rossignol et al. | |
| 9,126,992 | B2 | 9/2015 | Rossignol et al. | |
| 2004/0082629 | A1 | 4/2004 | Iwataki et al. | |
| 2004/0192746 | A1 | 9/2004 | Sanner et al. | |
| 2004/0242518 | A1 | 12/2004 | Chen et al. | |
| 2005/0090506 | A1 | 4/2005 | Iwataki et al. | |
| 2005/0112751 | A1 | 5/2005 | Fang et al. | |
| 2006/0111409 | A1 | 5/2006 | Muto et al. | |
| 2006/0167053 | A1 | 7/2006 | Iino et al. | |
| 2006/0194853 | A1 | 8/2006 | Rossignol | |
| 2007/0004661 | A1 | 1/2007 | Stein et al. | |
| 2007/0004701 | A1 | 1/2007 | Murphy et al. | |
| 2007/0015803 | A1 | 1/2007 | Rossignol | |
| 2007/0110685 | A1 | 5/2007 | Auspitz et al. | |
| 2007/0167504 | A1 | 7/2007 | Rossignol | |
| 2008/0097106 | A1 | 4/2008 | Rossignol | |
| 2008/0161324 | A1 | 7/2008 | Johansen et al. | |
| 2008/0182837 | A1 | 7/2008 | Steurer et al. | |
| 2009/0036467 | A1 | 2/2009 | Rossignol et al. | |
| 2009/0176991 | A1 | 7/2009 | Murray et al. | |
| 2010/0009970 | A1 | 1/2010 | Johansen et al. | |
| 2010/0075964 | A1 | 3/2010 | Busch et al. | |
| 2010/0081713 | A1 | 4/2010 | Sharma et al. | |
| 2010/0331295 | A1 | 12/2010 | Busch et al. | |
| 2012/0122939 | A1 | 5/2012 | Rossignol et al. | |

FOREIGN PATENT DOCUMENTS

| | | | |
|---|---|---|---|
| EP | 1649852 | A1 | 4/2006 |
| GB | 2331748 | A | 6/1999 |
| JP | S27-122 | | 1/1952 |
| JP | 56-158703 | A | 12/1981 |
| JP | 64-009978 | A | 1/1989 |
| JP | 02-017177 | A | 1/1990 |
| JP | 2003-335680 | A | 11/2003 |
| SU | 910628 | B | 3/1982 |
| WO | WO 95/20567 | A1 | 8/1995 |
| WO | WO 95/28393 | A1 | 10/1995 |
| WO | WO 98/50035 | A1 | 11/1998 |
| WO | WO 00/02851 | A1 | 1/2000 |
| WO | WO 00/26202 | A2 | 5/2000 |
| WO | WO 02/092584 | A1 | 11/2002 |
| WO | WO 03/015774 | A1 | 2/2003 |
| WO | WO 03/103648 | A1 | 12/2003 |
| WO | WO 2004/028471 | A2 | 4/2004 |
| WO | WO 2004/085433 | A2 | 10/2004 |
| WO | WO 2006/031291 | A2 | 3/2006 |
| WO | WO 2006/042195 | A1 | 4/2006 |
| WO | WO 2006/122011 | A2 | 11/2006 |
| WO | WO 2007/002559 | A1 | 1/2007 |
| WO | WO 2007/008541 | A2 | 1/2007 |
| WO | WO 2007/016228 | A2 | 2/2007 |
| WO | WO 2007/076034 | A2 | 7/2007 |
| WO | WO 2007/125103 | A2 | 11/2007 |
| WO | WO 2007/140385 | A1 | 12/2007 |
| WO | WO 2008/070707 | A1 | 6/2008 |
| WO | WO 2009/001214 | A2 | 12/2008 |
| WO | WO 2009/065096 | A1 | 5/2009 |
| WO | WO 2009/152356 | A1 | 12/2009 |
| WO | WO 2009/152356 | A2 | 12/2009 |
| WO | WO 2010/026262 | A1 | 3/2010 |
| WO | WO 2010/034796 | A1 | 4/2010 |
| WO | WO 2010/059606 | A2 | 5/2010 |
| WO | WO 2010/107736 | A2 | 9/2010 |

OTHER PUBLICATIONS

Broekhuysen et al,. "Nitazoxanide: pharmacokinetics and metabolism in man," International Journal of Clinical Pharmacology and Therapeutics, 2000, 38(8):387-394.

Burger et al., "Isoterism and bioisoterism in drug design," Progress in Drug Research, Basel, 1991, 287-371.

Database Caplus [Online] Chemical Abstract Service, XP002498889, Database Accession No. 2000:53572 abstract of WO 00/02851, 3 pages.

Database Caplus [Online] Chemical Abstract Service, XP002498890, Database Accession No. 2003:918699, abstract of JP2003 335680 A, 1 page.

Database Caplus [Online] Chemical Abstract Service, XP002498892, Database Accession No. 2000:53572 abstract of WO 00/26202, 3 pages.

Database Registry [Online] Chemical Abstracts Service, Columbus, OH, US; 2000, XP002685340, retrieved from STN accession No. 304864-25-3 https://register.epo.org/espacenet/application?number=EP10775367, one page.

Hoffman et al., "Antiparasitic Drug Nitazoxanide Inhibits the Pyruvate Oxidoreductases of *Helicobacter pylori*, Selected Anaerobic Bacterial and Parasites, and *Campylobacter jejuni*," Antimicrobial Agents and Chemotherapy, Mar. 2007, 51(3):868-876.

Korba et al., "Use of a standardized cell culture assay to assess activities of nucleoside analogs against hepatitis B virus replication," Antiviral Research, 1992, 19:55-70.

Lipunova et al., "Fluorine-Containing Heterocycles: Xii. Fluorine-Containing Quinazolin-4-ones and Azolo[α]quinazolinone Derivatives," Russian Journal of Organic Chemistry, 2005, 41(7):1071-1080.

Locarnini, Stephen M.D., Ph.D., "Molecular Virology of Hepatitis B Virus," Seminars in Liver Disease, 2004, 24(Suppl. 1):3-10.

Ortiz et al., "Randomized clinical study of nitazoxanide compared to metronidazole in the treatment of symptomatic giardiasis in children from Northern Peru," Ailment Pharmacol. Ther., 2001, 15:1409-1415.

Pankuch et al., "Activities of Tizoxanide and Nitazoxanide Compared to Those of Five Other Thiazoles and Three Other Agents against Anaerobic Species," Antimicrobial Agents and Chemotherapy, Mar. 2006, 50(3):1112-1117.

Poland et al., "Influenza Virus Resistance to Antiviral Agents: A Plea for Rational Use," CID, May 1, 2009, 48:1254-1256.

Rao et al., "Design, Synthesis, and Biological Evaluation of 6-Substituted-3-(4-methanesulfonylphenyl)-4-phenylpyran-2-ones: A Novel Class of Diarylheterocyclic Selective Cyclooxygenase-2 Inhibitors," J. Med. Chem., 2003, 46:4872-4882.

Rossignol et al., "Thiazolides, a New Class of Anti-influenza Molecules Hemagglutinin at the Post-translation Level," J. Biol. Chem., Oct. 23, 2009, 284(43):29798-29808.

Rossignol et al., "Treatment of Diarrhea Caused by *Giardia intestinalis* and *Entamoeba histolytice* or *E. disbar.* A Randomized, Double-Blind, Placebo-Controlled Study of Nitazoxanide," J. Infect. Diseases, 2001, 184:381-384.

Stockis et al., "Nitazoxanide pharmacokinetics and tolerability in man during 7 days of 0.5 g and 1 g b.i.d. dosing," International Journal of Clinical Pharmacology and Therapeutics, 2002, 40(5):221-227.

Tellinghuisen et al., "Structure of the zinc-binding domain of an essential component of the hepatitis C virus replicase," Nature Letters, 2005, 435:374-379.

Tong et al., "Identification and analysis of fitness of resistance mutations against the HCV protease inhibitor SCH 503034," Antiviral Research, 2006, 70:26-38.

Balachandran et al., "Essential Role for the dsRNA-Dependent Protein Kinase PKR in Innate Immunity to Viral Infection," Immunity, Jul. 2000, 13(1):129-141.

(56) References Cited

OTHER PUBLICATIONS

Carr et al., "The lack of RNA-dependent protein kinase enhances susceptibility of mice to genital herpes simplex virus type 2 infection," Immunology, 2006, 118(4):520-526.
Elazar et al., "The Anti-Hepatitis C Agent Nitazoxanide Induces Phosphorylation of Eukaryotic Initiation Factor 2α Via Protein Kinase Activated by Double-Stranded RNA Activation," Gastroenterology, 2009, 137(5):1827-1835.
Garcia et al., "Impact of Protein Kinase PKR in Cell Biology: from Antiviral to Antiproliferative Ation," Microbiology and Molecular Biology Reviews, Dec. 2006, 70(4):1032-1060.
Hyojun Biseibutugaku (Microbiological Standard), Editorial supervision of Rinji Kawana, Igaku-Shoin Ltd., 1996, 6th Edition, p. 392.
Minor et al., "Double-Stranded RNA-Activated Protein Kinase Regulates Early Innate Immune Responses During Respiratory Syncytial Virus Infection," Journal of Interferon & Cytokine Research, Apr. 2010, 30(4):263-272.
Rossignol et al., "Effect of Nitazoxanide in Treating Rotavirus Gastroenteritis in Hospitalized Pediatric Patients," Gastroenterology, 2006, 130(4,Suppl.2):A-01, 10.
Seikagaku Jiten (Dictionary of Biochemistry), Editorial supervision of Kazutomo Imabori et al., Tokyo Kagaku Dojin Co. Ltd., 1998, 3rd Edition, pp. 552, 798 and 1462.
U.S. Appl. No. 15/133,534, filed Mar. 16, 2015, Rossignol et al.
Teran et al., "Nitozoxanide vs. probiotics for the treatment of acute rotavirus diarrhea in children: a randomized, single-blind, controlled trial in Bolivian children," International Journal of Infectious Diseases, 2009, 13:518-523.
Boyer et al, Journal Flourine Chemistry, vol. 127 (2006), pp. 1522-1527.*
Giocometti et al., "Activity of nitazoxanide alone and in combination with azithromycin and rifabutin against *Cryptosporidium parvum* in cell culture," Journal of Antimicrobial Chemotherapy, 2000, 45:453-456.
U.S. Appl. No. 12/821,571, filed Jun. 23, 2010, Rossignol et al.
Angus et al., "Resistance fo Adefovir Dipivoxil Therapy Associated With the Selection of a Novel Mutation in the HBV Polymerase," Gastoenterology, 2003, 125:292-297.
Belen'Kii et al., "Multiple drug effect analysis with confidence interval," Antiviral Research, 1994, 25:1-11.
Bellone et al., Annali di Chimica, 1964, V5 N54, 510-519, English Summary on first page.
Chen et al., "The Natural History of Hepatitis C Virus (HCV) Infection," Int. J. Med. Sci., 2006, 3:47-52.
Database Caplus [Online] Chemical Abstract Service, XP002498891, Database Accession No. 1964:468902, 1 page abstract of Bellone et al., "New substituted acetophenones and their derivatives," Annali di Chimica, Societa Chimia Italiana, Rome, Italy, vol. 5, No. 54, Jan. 1, 1964, 510-519.
Database Registry [Online] Chemical Abstracts Service, Columbus, Ohio, US, 2000, XP002684230, retrieved from STN accession No. 304864-25-3, compounds 304864-25-3.
Fox et al., "Nitazoxanide: A New Thiazolide Antiparasitic Agent," Review of Anti-Infective Agents, Apr. 15, 2005, 40:1173-1180.
International Search Report and Written Opinion dated Aug. 23, 2010, in PCT/US2010/039638, 11 pages.
International Search Report and Written Opinion dated Jul. 9, 2010, in corresponding PCT/US2010/034319, 10 pages.
International Search Report dated Oct. 17, 2008, in PCT/US2008/071990, 5 pages.
Iyer et al., "Phosphorothioate Di- and Trinucleotides as a Novel Class of Anti-Hepatitis B Virus Agents," Antimicrobial Agents and Chemotherapy, Jun. 2004, 48(6):2199-2205.
Kabanov, Alexander V., "Polymer Genomics: An Insight into Pharmacology and Toxicology of Nanomedicines," Adv. Drug Deliv. Rev., Dec. 30, 2006, 58(15):1597-1621.
Korba et al., "Antisense oligonucleotides are effective inhibitors of hepatitis B virus replication in vitro," Antiviral Research, 1995, 28:225-242.
Korba et al., "Nitazoxanide, tizoxanide and other thiazoles are potent inhibitors of hepatits B virus and hepatitis C virus replication," Antiviral Research, 2008, 77:56-63.
Korba et al., "Potential for Hepatitis C Virus Resistance to Nitazoxanide or Tizoxanide," Antimicrobial Agents and Chemotherapy, Nov. 2008, 52(11):4069-4071.
Lavanchy, D., "Hepatitis B virus epidemiology, disease burden, treatment, and current and emerging prevention and control measures," Journal of Viral Hepatitis, 2004, 11:97-107.
Masihi et al., "Low dose oral combination chemoprophylaxis with osletamivir and amantadine for influenza A virus infections in mice," J. Chemother., Jun. 2007, 19(3):295-303.
Mueller et al., "In Vitro Effects of Thiazolides on *Giardia lamblia* WB Cline C6 Cultured Axenically and in Coculture with Caco2 Cells," Antimicrobial Agents and Chemotherapy, Jan. 2006, 50(1):162-170.
Musher et al., "Nitazoxanide for the Treatment of *Clostridium difficile* Colitis," CID, Aug. 15, 2006, 43:421-427.
Okuse et al., "Enhancement of antiviral activity against hepatitis C virus in vitro by interferon combination therapy," Antiviral Research, 2005, 65:23-34.
Patani et al., "Bioisoterism: A Rational Approach in Drug Design," Chem. Rev., 1996, 96(8):3147-3176.
Rossignol et al., "Effect of nitazoxanide for treatment of severe rotavirus diarrhea: randomized double-blind placebo-controlled trial," The Lancet, Jun. 13, 2006 online, 1-6.
Rossignol et al., "Effect of Nitazoxanide in Diarrhea and Enteritis Caused by *Cryptosporidium* Species," Clinical Gastoenterology and Hepatology, 2006, 4:320-324.
Rossignol et al., "Effect of Nitazoxanide in Persistent Diarrhea and Enteritis Associated with *Blastocystis hominis*," Clinical Gastroenterology and Hepatology, 2005, 3:987-991.
Rossignol et al., "Nitazoxanide in the treatment of viral gastroenteritis: a randomized double-blind placebo-controlled clinical trial," Aliment. Pharacol. Ther., 2006, 24:1423-1430.
Santoro et al., "Thoazolides: A New Class of Broad-Spectrum Antiviral Drugs Targeting Virus Maturation," Antiviral Research, Program and Abstracts, The Twentieth International Conference on Antiviral Research, 2007, 74:A31 (11).
Schiavi et al., "Preparation of N-Tert-butoxycarbonylthiourea opens the way to protected 2-aminothiazoles," Synthetic Communications, 2002, 32(11):1671-1674.
Sells et al., "Replicative Intermediates of Hepatitis B Virus in HepG2 Cells That Produce Infectious Virions," J. Virol., Aug. 1988, 62(8):2836-2844.
Stockis et al., "Nitazoxandide pharmacokinetics and tolerability in man during 7 days of 0.5 g and 1 g b.i.d. dosing," International Journal of Clinical Pharmacology and Therapeutics, 2002, 40(5):221-227.
Tellinghuisen et al., Structure of the zinc-binding domain of an essential component of the hepatitis C virus replicase, Nature Letters, 2005, 435:374-379.
Tomei et al., "HCV antiviral resistance: the impact of in vitro studies on the development of antiviral agents targeting the viral NS5B polymerase," Antiviral Chemistry & Chemotherapy, 2005, 16:225-245.
Tong et al., "Identification and analysis of fitness of resistance mutations againstthe HCV protease inhibitor SCH 503034," Antiviral Research, 2006, 70:26-38.
Wong et al., "Update of viral hepatitis: 2005," Current Opinion in Gastroenterology, 2006, 22:241-247.
Yim et al., "Evolution of Multi-Drug Resistant Hepatitis B Virus During Sequential Therapy," Hepatology, Sep. 2006, 44(3):703-712.
Ziegler et al., "2-Aminothiazolesulfonamides," J. Org. Chem., 1960, 25:1454-1455.

* cited by examiner

HALOALKYL HETEROARYL BENZAMIDE COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application *is a Reissue Application of U.S. Pat. No. 9,126,992, which issued on Sep. 8, 2015 from U.S. application Ser. No. 14/658,409, which* is a Divisional of U.S. application Ser. No. 12/777,383, filed May 11, 2010, *which issued as U.S. Pat. No. 8,846,727, on Sep. 30, 2014,* which claims benefit of U.S. Provisional Application No. 61/177,626, filed May 12, 2009, the entire contents of which are incorporated herein by reference.

STATEMENT REGARDING FEDERALLY SPONSORED RESEARCH OR DEVELOPMENT

This invention was funded by NIAID contract NO1-AI-30046. The United States government has certain rights in the invention.

FIELD OF THE INVENTION

The present invention is directed to new heterocyclic compounds, pharmaceutically acceptable salts thereof, compositions comprising such compounds and salts, and methods of using those compounds, salts, and compositions for the treatment of viral disease. It is also directed to methods of inhibition of viral pathogen activity in humans and animals. It is also directed to treatment of hepatitis C virus (HCV), hepatitis B virus (HBV), and related viral pathogen infection in humans and animals.

BACKGROUND

The present application relates generally to the field of thiazolide compounds. In particular, the application relates to haloalkyl-substituted thiazolide compounds.

Hepatitis B Virus (HBV) and Hepatitis C Virus (HCV) are major public health problems, causing more than an estimated 500 million chronic infections worldwide. Both viruses cause significant progressive liver disease and are major risk factors for primary hepatocellular carcinoma. Current standards of care for both HBV and HCV infections, while effective in many cases, are sub-optimal and fail to produce either a virologic or a clinical 'cure' in most. The development of drug-resistance in HBV, including strains carrying resistance to multiple currently used agents, is an emerging clinical problem, and drug-resistance for future HCV therapies is predicted to be a significant clinical issue

SUMMARY

This invention provides novel compounds and pharmaceutical compositions that treat viral pathogens, as well as methods of synthesizing and using the compounds to treat and inhibit viral infection. The compounds of this invention are haloalkyl heteroaryl benzamides In one embodiment, this invention provides compounds of Formula I and (I)

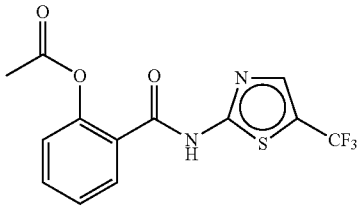

pharmaceutically acceptable salts thereof wherein:

$R_1$ through $R_5$ and $R_{10}$ are, independently chosen hydrogen, CN, $NO_2$, halogen, hydroxy, alkyl, alkenyl, alkynyl, alkoxy, alkenyloxy, alkynyloxy, alkoxyalkynyl, alkenyloxyalkyl, alkenyloxyalkenyl, alkenyloxyalkynyl, alkynyloxyalkyl, alkoxyalkylamino, hydroxyalkyl, acyl, acyloxy, aroyloxy, arylalkanoyloxy, arylalkenoyloxy, heteroaroyloxy, heteroarylalkanoyloxy, heteroarylalkenoyloxy, alkoxycarbonyl, aryloxycarbonyl, heteroaryloxycarbonyl, heteroarylalkoxycarbonyl, alkoxycarbonyloxy, carbamoyl, carbamoyloxy, alkylamino, dialkylamino, alkylaminoalkyl, amido, alkylamido, dialkylamido, perhaloalkoxy, alkylthio, perhaloalkylthio, alkylthioalkyl, alkylsulfonyl, alkylsulfonylalkyl, alkenylsulfonyl, alkynylsulfonyl, cycloalkylsulfonylalkyl, cycloalkylalkylsulfonylalkyl, arylsulfonyl, arylalkylsulfonyl, arylalkenylsulfonyl, heteroarylsulfonyl, heteroarylalkylsulfonyl, heteroarylalkenylsulfonyl, aryl, aryloxy, arylthio, arylalkylthio, alkylthio, perhaloalkylthio, arylamino, arylalkylamino, arylalkenyl, arylalkynyl, heteroaryl, heteroarylalkyl, heteroarylalkenyl, heteroarylalkynyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, or heterocycloalkenyloxy, all optionally substituted as described below wherein $R_6$ is selected from the group consisting of haloalkyl, perhaloalkyl, haloalkoxy, perhaloalkoxy, $S(O)_mC(R_7R_8)_nCF_3$, and $C(R_7R_8)_nCF_3$;

wherein W, X and Y are, independently, S, O, N, $NR_9$ or $CR_{10}$ where at least two of W, X, and Y are S, O, N, or $NR_9$;

wherein $R_7$, $R_8$, and $R_9$ are independently selected from the group consisting of hydrogen, fluoro, chloro, alkyl, perhaloalkyl, aryl, arylalkyl, heteroaryl and heteroarylalkyl, or $R_7$ and $R_8$, together with the atoms to which they are attached, are joined to form a 3- to 8-membered cycloalkyl ring or a 4- to 8-membered heterocycloalkyl, either ring optionally substituted as described below;

m is an integer between 0 and 2; and n is an integer between 0 and 5;

or a pharmaceutically acceptable salt or ester thereof

These compounds are useful in treating disorders and conditions caused by viral pathogens.

In another embodiment, this invention provides or contemplates a composition comprising a compound of formula I and a carrier.

In another embodiment, this invention provides or contemplates a pharmaceutical composition comprising a compound of Formula I and a pharmaceutically acceptable carrier.

In another embodiment, this invention provides or contemplates a method of treatment of viral infection comprising administering to a human or animal afflicted with viral infection a therapeutically effective amount of a compound of Formula I.

In a more specific embodiment, this invention provides or contemplates a method of treatment of HCV infection comprising administering to a human or animal afflicted with viral infection a therapeutically effective amount of a compound of Formula I.

In a more specific embodiment, this invention provides or contemplates a method of treatment of HBV infection comprising administering to a human or animal afflicted with viral infection a therapeutically effective amount of a compound of Formula I.

In other embodiments, the present invention provides or contemplates methods for inhibiting or modulating a viral pathogen. In other embodiments, the present invention provides or contemplates methods for treating a viral-mediated disorder in a patient in need of such treatment comprising administering to said patient a therapeutically effective amount of a compound or composition of compounds of this invention. In other embodiments, this invention provides or contemplates methods for treating HCV, HBV, and other viral infections comprising administering pharmaceutical compositions of the invention to a patient in need thereof. For example, the patient may have a chronic HCV infection. The present invention also contemplates the use of compounds disclosed herein for use in the manufacture of a medicament for the treatment of a disease or condition ameliorated by the inhibition or modulation of viral activity.

DETAILED DESCRIPTION

Unless otherwise specified, "a" or "an" means "one or more."

In one embodiment, this invention provides or contemplates a compound of Formula I, wherein $R_1$ through $R_5$ are, independently, hydrogen, cyano, fluoro, chloro, bromo, hydroxy, alkyl, alkoxy, aryloxy, aroyloxy, heteroaroyloxy, heteroarylalkanoyloxy, alkoxycarbonyloxy, carbamoyloxy, alkylamino, haloalkyl, perhaloalkyl, perhaloalkylthio, perhaloalkoxy, alkylthio, alkylthioalkyl, alkylsulfonyl, cycloalkylsulfonyl, or cycloalkylalkylsulfonyl, all optionally substituted as described below.

$R_6$ is selected from the group consisting of perhaloalkyl, $S(O)_mC(R_7R_8)_nCF_3$, and $C(R_7R_8)_nCF_3$;

$R_7$, $R_8$, and $R_9$ are, independently, hydrogen, fluoro, chloro, alkyl, or perhaloalkyl, any of which may be optionally substituted;

$R_{10}$ is selected from the group consisting of hydrogen, CN, $NO_2$, F, Cl, Br, alkyl, alkoxy, acyl, alkoxycarbonyl, aryloxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy; and m and n are, independently, integers equal to 0, 1, or 2.

In a more specific embodiment, this invention provides or contemplates a compound of Formula I wherein $R_1$, $R_2$, or $R_3$ are, independently, hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, or carbamoyloxy, any of which may be optionally substituted.

In another more specific embodiment, this invention provides or contemplates a compound of Formula I wherein one of $R_1$, $R_2$ and $R_3$ is hydroxy or acetoxy.

In another more specific embodiment, this invention provides or contemplates a compound of Formula I wherein either $R_3$ or $R_4$ is halogen.

In a still more specific embodiment, this invention provides or contemplates a compound of Formula I wherein one of $R_1$, $R_2$ and $R_3$ is hydroxy or acetoxy and wherein $R_4$ is halogen.

In a still more specific embodiment, this invention provides or contemplates a compound of Formula I wherein $R_1$ is hydroxy or acetoxy and wherein $R_2$, $R_3$ or $R_4$ is halogen.

In another more specific embodiment, this invention provides or contemplates a compound of Formula I wherein $R_3$ or $R_4$ is methyl or methoxy.

In another more specific embodiment, this invention provides or contemplates a compound of Formula I wherein one of $R_1$, $R_2$ and $R_3$ is hydroxy or acetoxy.

In another embodiment, this invention provides or contemplates a compound of Formula I wherein $R_6$ is selected from the group consisting of perhaloalkyl and $C(R_7R_8)_nCF_3$, wherein $R_7$ and $R_8$ are as defined above.

In another embodiment, this invention provides or contemplates a compound of Formula I wherein $R_6$ is perfluoroalkyl or perchloroalkyl.

In another embodiment, this invention provides or contemplates a compound of Formula I wherein $R_6$ is perfluoro or perchloro $C_1$-$C_3$ alkyl.

In another embodiment, this invention provides or contemplates a compound of Formula I wherein $R_6$ is trifluoromethyl.

In another embodiment this invention provides or contemplates pharmaceutical compositions comprising one or more compounds of the present invention together with a pharmaceutically acceptable carrier (e.g., a diluent or excipient). It other embodiments this invention provides or contemplates methods of making and using the compounds and compositions. In more specific embodiments, the invention provides or contemplates pharmaceutical compositions which comprise therapeutically effective amounts of the compound of this invention and methods of using such compositions for treating HCV, HBV, and other viral infections.

In one subgeneric embodiment, this invention provides or contemplates a compound of Formula I in which W is O and either X or Y is N or $NR_9$.

In another embodiment, this invention provides or contemplates a compound of Formula I in which W is O and both X and Y are N or $NR_9$.

In another embodiment, this invention provides or contemplates a compound of Formula I in which W is S and either X or Y is N or $NR_9$.

In another embodiment, this invention provides or contemplates a compound of Formula I in which W is S and both X and Y are N or $NR_9$.

In another embodiment, this invention provides or contemplates a compound of Formula I in which W is N and either X or Y is O.

In another embodiment, this invention provides or contemplates a compound of Formula I in which W is N and either X or Y is S.

In another embodiment, this invention provides or contemplates a compound of Formula I in which W is N and either X or Y is N or $NR_9$ In another embodiment, this invention provides or contemplates a compound of Formula I in which two of W, X, and Y are N or $NR_9$.

In another embodiment, this invention provides or contemplates a compound of Formula I in which W, X, and Y are N or $NR_9$.

In another embodiment, this invention provides or contemplates a compound of Formula I in which W is $CR_{10}$, one of X or Y is O, and the other is N or $NR_9$.

In another embodiment, this invention provides or contemplates a compound of Formula I in which W is $CR_{10}$, one of X or Y is O and the other is N or $NR_9$.

In one subgeneric embodiment, this invention provides or contemplates a compound of Formula I in which W is O and either X or Y is N or $NR_9$.

In another embodiment, this invention provides or contemplates a compound of Formula I in which W is O and both X and Y are N or $NR_9$.

In another embodiment, this invention provides or contemplates a compound of Formula I in which W is S and either X or Y is N or $NR_9$.

In another embodiment, this invention provides or contemplates a compound of Formula I in which W is S and both X and Y are N or $NR_9$.

In another embodiment, this invention provides or contemplates a compound of Formula I in which W is N or $NR_9$ and either X or Y is O.

In another embodiment, this invention provides or contemplates a compound of Formula I in which W is N or $NR_9$ and either X or Y is S.

In another embodiment, this invention provides or contemplates a compound of Formula I in which W is N; either X or Y is N or $NR_9$; and $R_6$ is $SO_2CF_3$ or $SO_2CH_2CF_3$.

In another embodiment, this invention provides or contemplates a compound of Formula I in which W is N; either X or Y is N or $NR_9$; and $R_6$ is $CF_2CH_3$, $CF_2CF_3$ or $CH_2CF_3$.

In another embodiment, this invention provides or contemplates a compound of Formula I in which W is N, in which either X or Y is N or $NR_9$, and wherein $R_6$ is $SO_2CF_3$ or $SO_2CH_2CF_3$.

In another embodiment, this invention provides or contemplates a compound of Formula I in which W is N, in which either X or Y is N or $NR_9$, and wherein $R_6$ is $CF_2CH_3$, $CF_2CF_3$ or $CH_2CF_3$.

In another embodiment, this invention provides or contemplates a compound of Formula I in which two of W, X, and Y are N or $NR_9$ and wherein $R_6$ is $CF_2CH_3$, $CF_2CF_3$ or $CH_2CF_3$.

In another embodiment, this invention provides or contemplates a compound of Formula I in which two of W, X, and Y are N or $NR_9$ and wherein $R_6$ is $SO_2CF_3$ or $SO_2CH_2CF_3$.

In another embodiment, this invention provides or contemplates a compound of Formula I in which W, ×, and Y are N or $NR_9$ and wherein $R_6$ is $SO_2CF_3$ or $SO_2CH_2CF_3$.

In another embodiment, this invention provides or contemplates a compound of Formula I in which W, X, and Y are N or $NR_9$ and wherein $R_6$ is $CF_2CH_3$, $CF_2CF_3$ or $CH_2CF_3$.

In another embodiment, this invention provides or contemplates a compound of Formula I in which one of X or Y is O and the other is N or $NR_9$ and wherein $R_6$ is methyl, fluoromethyl, or trifluoromethyl.

In another embodiment, this invention provides or contemplates a compound of Formula I in which one of X or Y is O and the other is N or $NR_9$ and wherein $R_6$ is $SO_2CF_3$ or $SO_2CH_2CF_3$.

In another embodiment, this invention provides or contemplates a compound of Formula I wherein one of X or Y is O and the other is N or $NR_9$ and wherein $R_6$ is methyl, fluoromethyl, or trifluoromethyl.

In another embodiment, this invention provides or contemplates a compound of Formula I wherein one of X or Y is O and the other is N or $NR_9$ and wherein $R_6$ is $SO_2CF_3$ or $SO_2CH_2CF_3$.

In another embodiment, this invention provides or contemplates a compound of Formula I wherein $R_6$ is methyl, fluoromethyl, or trifluoromethyl.

In another embodiment, this invention provides or contemplates a compound of Formula I wherein $R_6$ is $SO_2CF_3$ or $SO_2CH_2CF_3$.

In another embodiment, this invention provides or contemplates a compound of Formula I wherein $R_6$ is $CF_2CH_3$, $CF_2CF_3$ or $CH_2CF_3$.

In another embodiment, this invention provides or contemplates a compound of Formula I in which three of $R_1$-$R_5$— are H.

In another embodiment, this invention provides or contemplates a compound of Formula I in which two of $R_2$-$R_5$— are H.

In another embodiment, this invention provides or contemplates a compound of Formula I in which three of $R_2$-$R_5$— are H.

In another embodiment, this invention provides or contemplates a compound of Formula I in which $R_2$-$R_5$— are H.

In another embodiment, this invention provides or contemplates a compound of Formula I in which one of $R_1$-$R_5$ is O—$R_{12}$, where $R_{12}$ is H or $C_1$-$C_6$ alkanoyl, the latter optionally substituted with 1-3 halogens In another embodiment, this invention provides or contemplates a compound of Formula I in which $R_6$ is $C_1$-$C_3$ alkyl, optionally substituted with 1-3 halogens.

In another embodiment, this invention provides or contemplates a compound of Formula I wherein $R_6$ is methyl, fluoromethyl, or trifluoromethyl.

In another embodiment, this invention provides or contemplates a compound of Formula I wherein $R_6$ is $SO_2CF_3$ or $SO_2CH_2CF_3$.

In another embodiment, this invention provides or contemplates a compound of Formula I wherein $R_6$ is $CF_2CH_3$, $CF_2CF_3$ or $CH_2CF_3$.

In another embodiment, this invention provides or contemplates a compound of Formula I wherein $R_1$ is hydroxy or alkanoyloxy.

In a more specific embodiment, this invention provides or contemplates a compound of Formula I wherein $R_1$ is hydroxy or $C_1$-$C_3$ alkanoyloxy.

In another embodiment, this invention provides or contemplates a compound of Formula II (II)

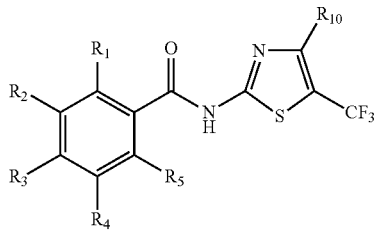

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In additional embodiments, this invention provides or contemplates a compound of Formula II wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In a still more specific embodiment, this invention provides or contemplates a compound of Formula II wherein $R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In a more specific embodiment, this invention provides or contemplates a compound of Formula II wherein $R_1$ is hydroxy or $C_1$-$C_3$ alkanoyloxy.

In a still more specific embodiment, this invention provides or contemplates a compound of Formula II wherein $R_1$ is hydroxy or acetoxy; and and 3, 4, or all of $R_2$-$R_5$ and $R_{10}$ are hydrogen.

In a still more specific embodiment, this invention provides or contemplates the following compounds of Formula I: 2-(5-(trifluoromethyl)thiazol-2-ylcarbamoyl)phenyl acetate and 2-hydroxy-N-(5-(trifluoromethyl)thiazol-2-yl) benzamide.

In another subgeneric embodiment, this invention provides or contemplates a compound of Formula III:

(III)

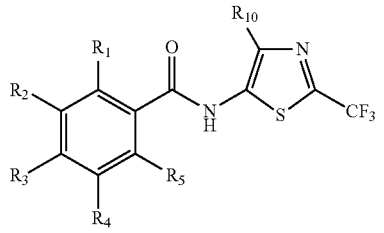

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In a more specific embodiment, this invention provides or contemplates a compound of Formula III wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In a still more specific embodiment, this invention provides or contemplates a compound of Formula III wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In another more specific embodiment, this invention provides or contemplates a compound of Formula III wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In a more specific embodiment, this invention provides or contemplates a compound of Formula III wherein $R_1$ is hydroxy or $C_1$-$C_3$ alkanoyloxy.

In another embodiment, this invention provides or contemplates a compound of Formula III wherein:

$R_1$ is chosen from the group consisting of hydroxy and acetoxy; and 3, 4, or all of $R_2$-$R_5$ and $R_{10}$ are hydrogen.

In another subgeneric embodiment, this invention provides or contemplates a compound of Formula IV:

(IV)

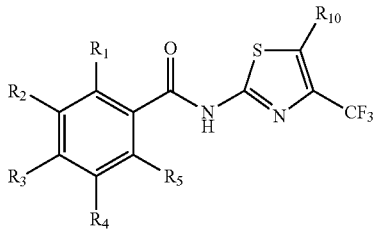

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In a more specific embodiment, this invention provides or contemplates a compound of Formula IV wherein:

$R_{10}$ is selected from the group consisting of hydrogen, CN, $NO_2$, F, Cl, alkyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl; an with the proviso that when $R_4$ is Br, $R_{10}$ may not be unsubstituted phenyl.

In a more specific subgeneric embodiment, this invention provides or contemplates a compound of Formula IV wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In a still more specific embodiment, this invention provides or contemplates a compound of Formula IV wherein $R_1$ is hydroxy or acetoxy; and 3, 4, or all of $R_2$-$R_5$ and $R_{10}$ are hydrogen.

Examples of this more specific embodiment include the compounds include 2-(4-(trifluoromethyl)thiazol-2-ylcarbamoyl)phenyl acetate and 2-hydroxy-N-(4-(trifluoromethyl)thiazol-2-yl)benzamide.

In another embodiment, this invention provides or contemplates a compound of Formula V:

(V)

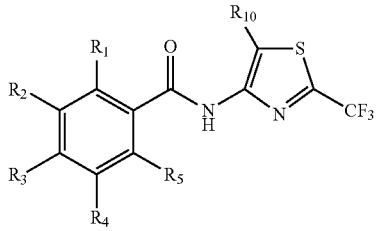

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In a more specific embodiment, this invention provides or contemplates a compound of Formula V wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In additional embodiments, this invention provides or contemplates a compound of Formula V wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In more specific embodiments, this invention provides or contemplates compounds of Formula V wherein:

$R_1$ is hydroxy or acetoxy; and 3, 4, or all of $R_2$ through $R_5$ and $R_{10}$ are hydrogen.

In another embodiment, this invention provides or contemplates a compound of Formula VI:

(VI)

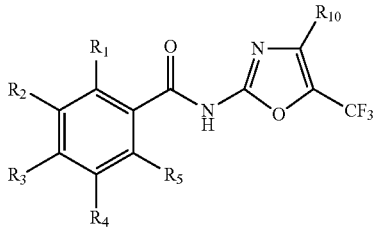

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In a more specific embodiment, this invention provides or contemplates a compound of Formula VI wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In a still more specific embodiment, this invention provides or contemplates a compound of Formula VI wherein:

$R_1$ is chosen from the group consisting of hydroxy, aryloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In more specific embodiments, this invention provides or contemplates compounds of Formula VI wherein $R_1$ is hydroxy or acetoxy; and 3, 4, or all of $R_2$ through $R_5$ and $R_{10}$ are hydrogen.

In a still more specific embodiment, this invention provides or contemplates a compound of Formula VI wherein:

$R_1$ is hydroxy or acetoxy; and $R_2$ through $R_5$ and $R_{10}$ are hydrogen.

In additional embodiments, this invention provides or contemplates a compound of Formula VII:

(VII)

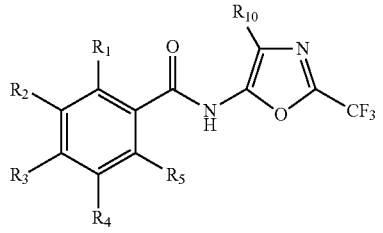

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In more specific subgeneric embodiments, the invention provides or contemplates a compound of Formula VII wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In more specific embodiments, this invention provides or contemplates a compound of Formula VII wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In more specific embodiments, this invention provides or contemplates compounds of Formula VII wherein $R_1$ is hydroxy or acetoxy; and 3, 4, or all of $R_2$ through $R_5$ and $R_{10}$ are hydrogen.

In a still more specific embodiment, this invention provides or contemplates a compound of Formula VII wherein:

$R_1$ is hydroxy or acetoxy; and $R_2$ through $R_5$ and $R_{10}$ are hydrogen.

In another embodiment, this invention provides or contemplates a compound of Formula VIII:

(VIII)

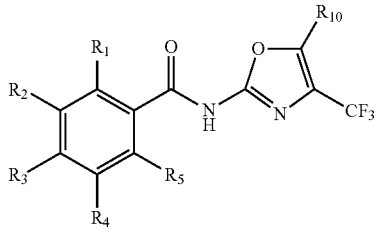

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy;

In some embodiments, the compounds of the present invention have structural Formula VIII wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In other embodiments, the compounds of the present invention have structural Formula VIII wherein:

$R_1$ is chosen from the group consisting of hydroxy, aryloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In more specific embodiments, this invention provides or contemplates compounds of Formula VIII wherein $R_1$ is hydroxy or acetoxy; and 3, 4, or all of $R_2$ through $R_5$ and $R_{10}$ are hydrogen.

In a still more specific embodiment, this invention provides or contemplates a compound of Formula VIII wherein: $R_1$ is hydroxy or acetoxy; and $R_2$ through $R_5$ and $R_{10}$ are hydrogen.

In certain embodiments, the compounds of the present invention have structural Formula IX:

(IX)

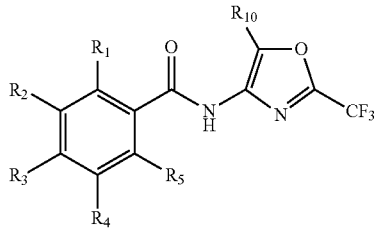

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy;

In some embodiments, the compounds of the present invention have structural Formula IX wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In other embodiments, the compounds of the present invention have structural Formula IX wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula IX wherein:

$R_1$ is chosen from the group consisting of hydroxy and acetoxy; and $R_2$ through $R_5$ and $R_{10}$ are hydrogen.

In certain embodiments, the compounds of the present invention have structural Formula X:

(X)

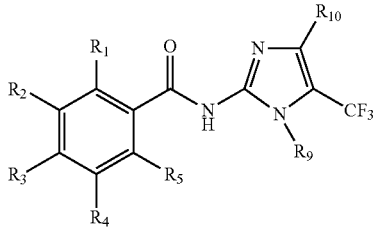

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted;

$R_9$ is selected from the group consisting of hydrogen, fluoro, chloro, alkyl, and perhaloalkyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In some embodiments, the compounds of the present invention have structural Formula X wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In other embodiments, the compounds of the present invention have structural Formula X wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted;

$R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted; and $R_9$ is selected from the group consisting of hydrogen, alkyl, and perhaloalkyl, any of which may be optionally substituted.

In other embodiments, the compounds of the present invention have structural Formula X wherein:

$R_1$ is chosen from the group consisting of hydroxy and acetoxy;

$R_2$ through $R_5$ and $R_{10}$ are hydrogen; and $R_9$ is alkyl, which may be optionally substituted.

In certain embodiments, the compounds of the present invention have structural Formula XI:

(XI)

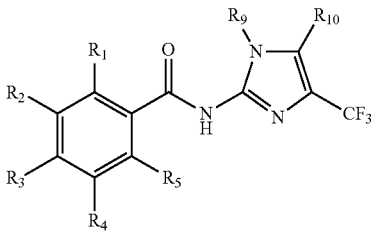

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted;

$R_9$ is selected from the group consisting of hydrogen, fluoro, chloro, alkyl, and perhaloalkyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In some embodiments, the compounds of the present invention have structural Formula XI wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In further embodiments, the compounds of the present invention have structural Formula XI wherein:

$R_1$ is chosen from the group consisting of hydroxy, aryloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted;

$R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted; and $R_9$ is selected from the group consisting of hydrogen, alkyl, and perhaloalkyl, any of which may be optionally substituted.

In certain embodiments, the compounds of the present invention have structural Formula XI wherein $R_1$ is chosen from the group consisting of hydroxy and acetoxy;

$R_2$ through $R_5$ and $R_{10}$ are hydrogen; and $R_9$ is alkyl, which may be optionally substituted.

In certain embodiments, the compounds of the present invention have structural Formula XII:

(XII)

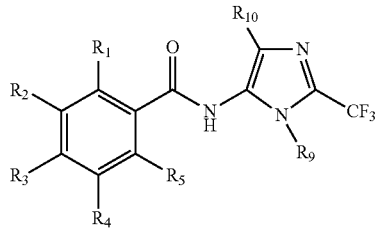

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted;

$R_9$ is selected from the group consisting of hydrogen, fluoro, chloro, alkyl, and perhaloalkyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In some embodiments, the compounds of the present invention have structural Formula XII wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In other embodiments, the compounds of the present invention have structural Formula XII wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted;

$R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted; and $R_9$ is selected from the group consisting of hydrogen, alkyl, and perhaloalkyl, any of which may be optionally substituted.

In certain embodiments, the compounds of the present invention have structural Formula XII wherein:

$R_1$ is chosen from the group consisting of hydroxy and acetoxy;

$R_2$ through $R_5$ and $R_{10}$ are hydrogen; and $R_9$ is alkyl, which may be optionally substituted.

In certain embodiments, the compounds of the present invention have structural Formula XIII:

(XIII)

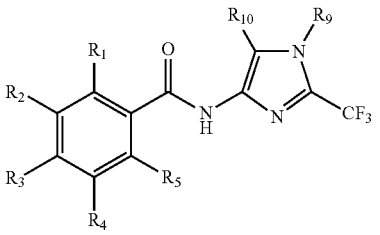

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted;

$R_9$ is selected from the group consisting of hydrogen, fluoro, chloro, alkyl, and perhaloalkyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy;

In some embodiments, the compounds of the present invention have structural Formula XIII wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In some embodiments, the compounds of the present invention have structural Formula XIII wherein:

$R_1$ is chosen from the group consisting of hydroxy, aryloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted;

$R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted; and $R_9$ is selected from the group consisting of hydrogen, alkyl, and perhaloalkyl, any of which may be optionally substituted.

In certain embodiments, the compounds of the present invention have structural Formula XIII wherein:

$R_1$ is chosen from the group consisting of hydroxy and acetoxy;

$R_2$ through $R_5$ and $R_{10}$ are hydrogen; and $R_9$ is alkyl, which may be optionally substituted.

In certain embodiments, the compounds of the present invention have structural Formula XIV:

(XIV)

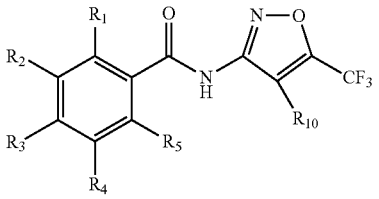

wherein:

$R_1$ through $R_5$ or, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, and cycloalkylalkylsulfonyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In some embodiments, the compounds of the present invention have structural Formula XIV wherein:

$R_1$ and $R_2$ are, independently, hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, or carbamoyloxy, any of which may be optionally substituted;

$R_3$ is selected from the group consisting of acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In other embodiments, the compounds of the present invention have structural Formula XIV wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula XIV wherein:

$R_1$ is chosen from the group consisting of hydroxy and acetoxy; and $R_2$ through $R_5$ and $R_{10}$ are hydrogen.

In certain embodiments, the compounds of the present invention have structural Formula XV:

(XV)

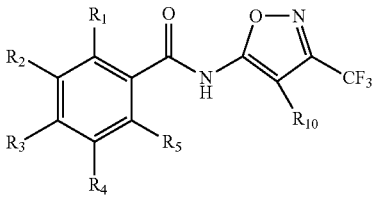

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In some embodiments, the compounds of the present invention have structural Formula XV wherein:

$R_1$ and $R_2$ are, independently, hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, or carbamoyloxy, any of which may be optionally substituted;

$R_3$ is selected from the group consisting of acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In other embodiments, the compounds of the present invention have structural Formula XV wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula XV wherein:

$R_1$ is chosen from the group consisting of hydroxy and acetoxy; and $R_2$ through $R_5$ and $R_{10}$ are hydrogen.

In certain embodiments, the compounds of the present invention have structural Formula XVI:

(XVI)

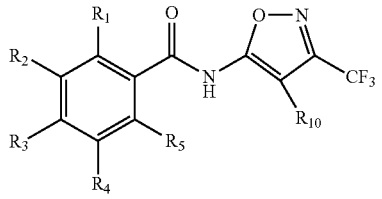

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In some embodiments, the compounds of the present invention have structural Formula XVI wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In further embodiments, the compounds of the present invention have structural Formula XVI wherein:

$R_1$ is chosen from the group consisting of hydroxy, aryloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula XVI wherein:

$R_1$ is chosen from the group consisting of hydroxy and acetoxy; and $R_2$ through $R_5$ and $R_{10}$ are hydrogen.

In certain embodiments, the compounds of the present invention have structural Formula XVII:

(XVII)

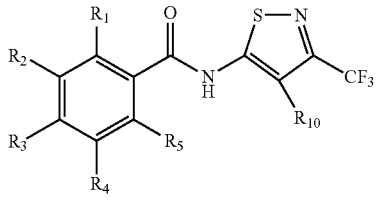

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In some embodiments, the compounds of the present invention have structural Formula XVII wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In other embodiments, the compounds of the present invention have structural Formula XVII wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula XVII wherein:

$R_1$ is chosen from the group consisting of hydroxy and acetoxy; and $R_2$ through $R_5$ and $R_{10}$ are hydrogen.

In certain embodiments, the compounds of the present invention have structural Formula XVIII:

(XVIII)

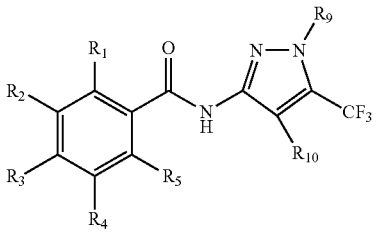

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted;

$R_9$ is selected from the group consisting of hydrogen, fluoro, chloro, alkyl, and perhaloalkyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy;

In some embodiments, the compounds of the present invention have structural Formula XVIII wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In other embodiments, the compounds of the present invention have structural Formula XVIII wherein:

$R_1$ is chosen from the group consisting of hydroxy, aryloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted;

$R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted; and $R_9$ is selected from the group consisting of hydrogen, alkyl, and perhaloalkyl, any of which may be optionally substituted.

In certain embodiments, the compounds of the present invention have structural Formula XVIII wherein:

$R_1$ is chosen from the group consisting of hydroxy and acetoxy;

$R_2$ through $R_5$ and $R_{10}$ are hydrogen; and $R_9$ is methyl.

In certain embodiments, the compounds of the present invention have structural Formula XIX:

(XIX)

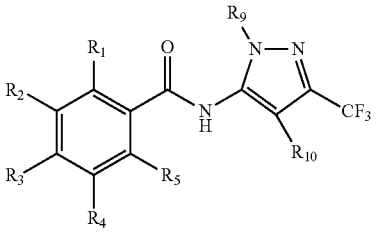

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted;

$R_9$ is selected from the group consisting of hydrogen, fluoro, chloro, alkyl, and perhaloalkyl, any of which may be optionally substituted; and $R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy.

In some embodiments, the compounds of the present invention have structural Formula XIX wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

In other embodiments, the compounds of the present invention have structural Formula XIX wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted:

$R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, and heterocycloalkoxy, any of which may be optionally substituted; or $R_9$ is selected from the group consisting of hydrogen, alkyl, and perhaloalkyl, any of which may be optionally substituted.

In certain embodiments, the compounds of the present invention have structural Formula XIX wherein:

$R_1$ is chosen from the group consisting of hydroxy and acetoxy;

$R_2$ through $R_5$ and $R_{10}$ are hydrogen; and $R_9$ is methyl.

In certain embodiments, the compounds of the present invention have structural Formula XX:

(XX)

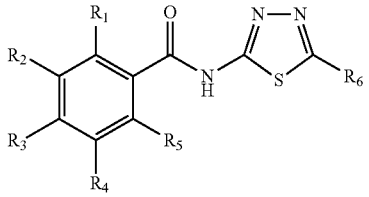

wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted;

$R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted;

$R_6$ is selected from the group consisting of perhaloalkyl, $S(O)_mC(R_7R_8)_nCF_3$, and $C(R_7R_8)_nCF_3$;

$R_7$ and $R_8$ are independently selected from the group consisting of hydrogen, fluoro, chloro, alkyl, and perhaloalkyl, any of which may be optionally substituted;

m is an integer between 0 and 2;

n is an integer between 0 and 2; and with the following provisos when $R_6$ is trifluoromethyl:

when $R_1$ is selected from the group consisting of hydroxy, and acetoxy, $R_2$-$R_5$ cannot be hydrogen;

when $R_1$ is hydroxy, $R_4$ cannot be selected from the group consisting of Cl and Br; and when $R_3$ is acetoxy, $R_1$, $R_2$, $R_4$ and $R_5$ may not be hydrogen.

In some embodiments, the compounds of the present invention have structural Formula XX:

$R_1$ is chosen from the group consisting of hydroxy and acetoxy;

$R_2$ through $R_5$ are hydrogen; and $R_6$ is perfluoroethyl, $CF_3CH_2$—, and $CH_3CF_2$—.

In certain embodiments, the compounds of the present invention have structural Formula XXI:

(XXI)

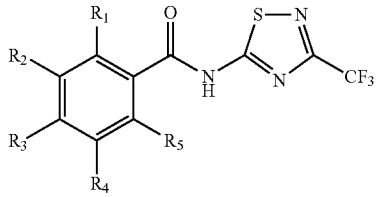

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted.

In other embodiments, the compounds of the present invention have structural Formula XXI, wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula XXI, wherein:

$R_1$ is chosen from the group consisting of hydroxy and acetoxy; and $R_2$ through $R_5$ are hydrogen.

In certain embodiments, the compounds of the present invention have structural Formula XXII:

(XXII)

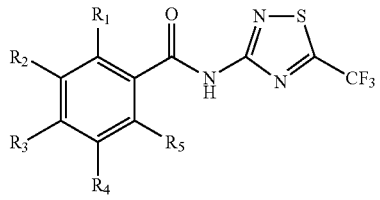

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted.

In other embodiments, the compounds of the present invention have structural Formula XXII, wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula XXII, wherein:

$R_1$ is chosen from the group consisting of hydroxy and acetoxy; and $R_2$ through $R_5$ are hydrogen.

In certain embodiments, the compounds of the present invention have structural Formula XXIII:

(XXIII)

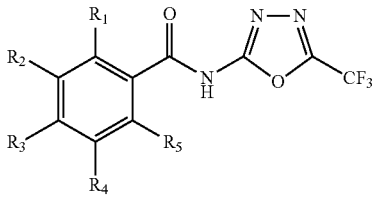

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted.

In other embodiments, the compounds of the present invention have structural Formula XXIII, wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula XXIII, wherein:

$R_1$ is chosen from the group consisting of hydroxy and acetoxy; and $R_2$ through $R_5$ are hydrogen.

In certain embodiments, the compounds of the present invention have structural Formula XXIV:

(XXIV)

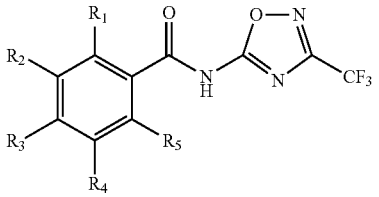

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted.

In other embodiments, the compounds of the present invention have structural Formula XXIV, wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula XXIV, wherein:

$R_1$ is chosen from the group consisting of hydroxy and acetoxy; and $R_2$ through $R_5$ are hydrogen.

In certain embodiments, the compounds of the present invention have structural Formula XXV:

(XXV)

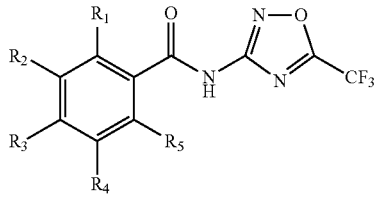

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted.

In other embodiments, the invention provides or contemplates a compound of Formula XXV, wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula XXV, wherein:

$R_1$ is chosen from the group consisting of hydroxy and acetoxy; and $R_2$ through $R_5$ are hydrogen.

In certain embodiments, the compounds of the present invention have structural Formula XXVI:

(XXVI)

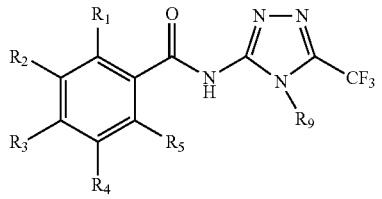

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_9$ is selected from the group consisting of hydrogen, alkyl, and perhaloalkyl, any of which may be optionally substituted.

In some embodiments, the compounds of the present invention have structural Formula XXVI wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula XXVI wherein:

$R_1$ is chosen from the group consisting of hydroxy and acetoxy;

$R_2$ through $R_5$ are hydrogen; and $R_9$ is methyl.

In certain embodiments, the compounds of the present invention have structural Formula XXVII:

(XXVII)

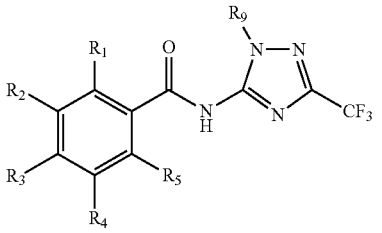

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_9$ is selected from the group consisting of hydrogen, alkyl, and perhaloalkyl, any of which may be optionally substituted.

In some embodiments, the compounds of the present invention have structural Formula XXVII wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula XXVII wherein:

$R_1$ is chosen from the group consisting of hydroxy and acetoxy;

$R_2$ through $R_5$ are hydrogen; and $R_9$ is methyl.

In certain embodiments, the compounds of the present invention have structural Formula XXVIII:

(XXVIII)

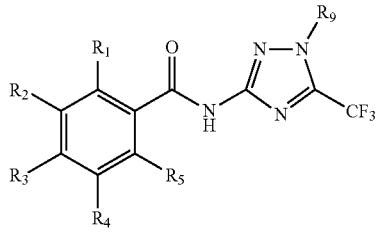

wherein:

$R_1$ through $R_5$ are, independently, hydrogen, CN, F, Cl, Br, hydroxy, alkyl, cycloalkyl, cycloalkylalkyl, alkoxy, alkoxyalkyl, cycloalkoxy, cycloalkylalkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted; and $R_9$ is selected from the group consisting of hydrogen, alkyl, and perhaloalkyl, any of which may be optionally substituted.

In some embodiments, the compounds of the present invention have structural Formula XXVIII wherein:

$R_1$ is chosen from the group consisting of hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, and carbamoyloxy, any of which may be optionally substituted; and $R_2$ through $R_5$ are, independently, hydrogen, CN, $NO_2$, F, Cl, Br, alkyl, cycloalkyl, alkoxy, cycloalkoxy, alkoxycarbonyl, aryloxycarbonyl, heteroaryloxycarbonyl, carbamoyl, amido, perhaloalkyl, alkylthio, alkylthioalkyl, alkylsulfonyl, cycloalkylsulfonyl, aryl, arylalkyl, aryloxy, arylalkoxy, arylthio, arylalkylthio, heteroaryl, heteroarylalkyl, heteroaryloxy, heteroarylthio, heteroarylalkylthio, heterocycloalkyl, or heterocycloalkoxy, any of which may be optionally substituted.

In certain embodiments, the compounds of the present invention have structural Formula XXVIII wherein:

$R_1$ is chosen from the group consisting of hydroxy and acetoxy;

$R_2$ through $R_5$ are hydrogen; and $R_9$ is methyl.

The disclosed compounds include compounds of formula (I), salts, and solvates thereof. For example, in some embodiments, the compound of the present invention may be a salt or a solvate.

Many compounds of this invention are capable of existing in more than one stereoisomeric form. All depictions of and references to compounds of this invention are intended to include all diastereomeric and enantiomeric forms of those compounds.

Because compounds of this invention may be used in the diagnosis as well as the treatment of disease, isotopically labeled versions of these compounds are included in this disclosure and in the claims. All references to elements in compounds of this invention are intended to include all isotopes of those elements, including unstable isotopes. For example, references to "hydrogen" or H in formulas or in claims are intended to include deuterium, (D) and tritium (T.)

In another embodiment, this invention provides or contemplates a kit, comprising, in a compartment, at least one pharmaceutical composition comprising, in a pharmaceutically acceptable carrier, an effective amount of at least one compound of the invention. In some embodiments, the kit further comprises written instructions for administering the pharmaceutical composition. In some embodiments, written instructions for administering concern indications noted elsewhere in this disclosure. In some embodiments, written instructions for administering concern an administration regimen noted elsewhere in this disclosure.

As used in the present specification the following terms have the meanings indicated:

The term "salts" is used in its broadest sense. For example, the term salts includes hydrogen salts and hydroxide salts with ions of the present compound. In some embodiments, the term salt may be a subclass referred to as pharmaceutically acceptable salts, which are salts of the present compounds having a pharmacological activity and which are neither biologically nor otherwise undesirable. In all embodiments, the salts can be formed with acids, such as, without limitation, hydrogen, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycero-phosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. In all embodiments, the salts can be formed with bases, such as, without limitation, hydroxide, ammonium salts, alkali metal salts such as lithium, sodium and potassium salts, alkaline earth metal salts such as calcium, magnesium salts, aluminum salts, salts with organic bases such as ammonia, methylamine, diethylamine, ethanolamine, dicyclohexylamine, N-methylmorpholine, N-methyl-D-glucamine, and salts with amino acids such as arginine and lysine. Basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The terms "therapeutically acceptable salt," and "pharmaceutically acceptable salt," as used herein, represent salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Basic addition salts can be prepared during the final isolation and purification of the compounds by reacting a carboxy, phenol or similar group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

The term "solvates" is used in its broadest sense. For example, the term solvates includes hydrates formed when a compound of the present invention contains one or more bound water molecules.

The term "acyl," as used herein, alone or in combination, refers to a carbonyl attached to an alkyl, alkenyl, aryl, heteroaryl, heterocycle, or any other moiety where the atom attached to the carbonyl is carbon. An "acetyl" group refers to a —C(O)$CH_3$ group. Examples of acyl groups include alkanoyl groups such as formyl, acetyl, and propionyl, aroyl groups such as benzoyl, and mixed alkyl-aryl groups such as cinnamoyl.

The term "acylamino" embraces an amino radical substituted with an acyl group. An example of an "acylamino" radical is acetylamino ($CH_3$C(O)NH—) The term "alkenyl," as used herein, alone or in combination, refers to a straight-chain, branched-chain, or cyclic unsaturated hydrocarbon radical, or a radical containing any combination of straight-chain or branched-chain, and cyclic moieties, having one or more double bonds and containing from 2 to 20 carbon atoms, or, in the case of cyclic moieties, having from 3 to 20 ring members. In many embodiments alkenyl groups comprise from 2 to 6 carbon atoms. The term "alkenyl groups" is used in its broadest sense. Alkenylene refers to a carbon-carbon double bond system attached at two or more positions such as ethenylene [(—CH═CH—),(—C::C—)]. For example, the term "($C_2$-$C_8$) alkenyl groups" embraces straight, branched, and cyclic hydrocarbon radicals containing 2 to 8 carbon atoms having at least one double bond. Examples of suitable alkenyl radicals include ethenyl, also known as vinyl, propenyl, iso-propenyl, butenyl, iso-butenyl, sec-butenyl, tert-butenyl, 1,3-butadienyl, n-pentenyl, n-hexenyl, cycloalkenyl radicals such as cyclohexenyl and 1,3-cyclopentadienyl, cycloalkenylalkyl radicals such as cyclohexenylmethyl, alkenylcycloalkyl radicals such as methylenecyclohexyl, and the like. The term "alkoxy," as used herein, alone or in combination, refers to an alkyl ether radical, wherein the term alkyl is as defined herein. Examples of suitable alkyl ether radicals include methoxy, ethoxy, n-propoxy, isopropoxy, n-butoxy, iso-butoxy, sec-butoxy, tert-butoxy, cyclopentoxy, and the like.

The term "alkoxyalkoxy," as used herein, alone or in combination, refers to one or more alkoxy groups attached to the parent molecular moiety through another alkoxy group. Examples include ethoxyethoxy, methoxypropoxyethoxy, ethoxypentoxyethoxyethoxy and the like.

The term "alkoxyalkyl," as used herein, alone or in combination, refers to an alkoxy group attached to the parent molecular moiety through an alkyl group. The term "alkoxyalkyl" also embraces alkoxyalkyl groups having one or more alkoxy groups attached to the alkyl group, that is, to form monoalkoxyalkyl and dialkoxyalkyl groups.

The term "alkoxycarbonyl," as used herein, alone or in combination, refers to an alkoxy group attached to the parent molecular moiety through a carbonyl group. Examples of such "alkoxycarbonyl" groups include methoxycarbonyl, ethoxycarbonyl, propoxycarbonyl, butoxycarbonyl and hexyloxycarbonyl.

The term "alkoxycarbonylalkyl" embraces radicals having "alkoxycarbonyl," as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl.

The term "alkyl," as used herein, alone or in combination, refers to a straight-chain, branched, or cyclic alkyl radical, or a radical consisting of any combination of straight, branched, and/or cyclic radicals, which is a saturated aliphatic hydrocarbon group containing from 1-20 carbon atoms. In many embodiments, alkyl groups comprise 1-10 carbon atoms. In many other embodiments, alkyl groups comprise 1-6 carbon atoms. The term "alkyl groups" is used in its broadest sense. Alkyl groups may be optionally substituted as defined herein. Examples of alkyl radicals include methyl, ethyl, n-propyl, isopropyl, cyclopropyl, cyclopropylmethyl, n-butyl, isobutyl, sec-butyl, tert-butyl, cyclobutyl, pentyl, neopentyl, iso-amyl, hexyl, cyclohexyl, trans-1, 2-di-ethylcyclohexyl, octyl, nonyl and the like. For example, the abbreviation "($C_1$-$C_6$)-alkyl groups" includes ($C_3$-$C_6$)-cycloalkyl groups as well as straight and branched alkyl groups, and "O($C_1$-$C_8$)-alkyl groups" includes the straight-chain O($C_1$-$C_8$)-alkyl groups, branched O($C_1$-$C_6$")-alkyl groups, and cyclic O($C_1$-$C_6$)-alkyl groups. The term "alkylene," as used herein, alone or in combination, refers to a saturated aliphatic group derived from a straight or branched chain saturated hydrocarbon attached at two or more positions, such as methylene (—$CH_2$—), ethylene, and 1,3-cyclobutylene.

The term "alkylamino," as used herein, alone or in combination, refers to an amino group attached to the parent molecular moiety through an alkyl group.

The term "alkylaminocarbonyl" as used herein, alone or in combination, refers to an alkylamino group attached to the parent molecular moiety through a carbonyl group. Examples of such radicals include N-methylaminocarbonyl and N,N-dimethylcarbonyl.

The term "alkylcarbonyl" and "alkanoyl," as used herein, alone or in combination, refers to an alkyl group attached to the parent molecular moiety through a carbonyl group. Examples of such groups include methylcarbonyl, also known as acetyl; ethylcarbonyl, also known as propionyl; and 2-methyl-cyclopentylcarbonyl, etc.

The term "alkylidene," as used herein, alone or in combination, refers to an alkenyl group in which one carbon atom of the carbon-carbon double bond belongs to the moiety to which the alkenyl group is attached.

The term "alkylsulfinyl," as used herein, alone or in combination, refers to an alkyl group attached to the parent molecular moiety through a sulfinyl group. Examples of alkylsulfinyl groups include methylsulfinyl, ethylsulfinyl, butylsulfinyl and hexylsulfinyl.

The term "alkylsulfonyl," as used herein, alone or in combination, refers to an alkyl group attached to the parent molecular moiety through a sulfonyl group. Examples of alkylsulfinyl groups include methanesulfonyl, ethanesulfonyl, tert-butanesulfonyl, and the like.

The term "alkylthio," as used herein, alone or in combination, refers to an alkyl thioether (R—S—) radical wherein the term alkyl is as defined above. Examples of suitable alkyl thioether radicals include methylthio, ethylthio, n-propylthio, isopropylthio, n-butylthio, iso-butylthio, sec-butylthio, tert-butylthio, ethoxyethylthio, methoxypropoxyethylthio, ethoxypentoxyethoxyethylthio and the like.

The term "alkylthioalkyl" embraces alkylthio radicals attached to an alkyl radical. Alkylthioalkyl radicals include "lower alkylthioalkyl" radicals having alkyl radicals of one to six carbon atoms and an alkylthio radical as described above. Examples of such radicals include methylthiomethyl.

The term "alkynyl," as used herein in its broadest sense, alone or in combination, refers to a straight-chain, branched chain, or cyclic unsaturated hydrocarbon radical, as well as a radical which contains any combination of straight, branched, and/or cyclic radicals, having one or more carbon-carbon triple bonds and containing from 2 to 20 carbon atoms. In many embodiments alkynyl groups contain from 2 to 6 carbon atoms. In many other embodiments alkynyl groups contain from 2 to 4 carbon atoms. "Alkynylene" refers to a carbon-carbon triple bond attached at two positions such as ethynylene (—C:::C—, —C≡C—). For example, ($C_2$-$C_8$) alkynyl groups embraces straight, branched, and cyclic hydrocarbon chains containing 2 to 8 carbon atoms having at least one triple bond, and the term includes but is not limited to substituents such as ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl, and the like, unless otherwise indicated.

The term "amido," as used herein, alone or in combination, refers to an amino group as described below attached to the parent molecular moiety through a carbonyl or sulfonyl group. The term "C-amido" as used herein, alone or in combination, refers to a —C(═O)—$NR_2$ group with R as defined herein. The term "N-amido" as used herein, alone or in combination, refers to a RC(═O)NH— group, with R as defined herein.

The term "amino," as used herein, alone or in combination, refers to —NRR', wherein R and R' are independently selected from the group consisting of hydrogen, alkenyl, alkoxy, alkoxyalkyl, alkoxycarbonyl, alkyl, alkylcarbonyl, aryl, arylalkenyl, arylalkyl, cycloalkyl, haloalkylcarbonyl, heteroaryl, heteroarylalkenyl, heteroarylalkyl, heterocycle, heterocycloalkenyl, and heterocycloalkyl, wherein the aryl, the aryl part of the arylalkenyl, the arylalkyl, the heteroaryl, the heteroaryl part of the heteroarylalkenyl and the heteroarylalkyl, the heterocycle, and the heterocycle part of the heterocycloalkenyl and the heterocycloalkyl can be optionally substituted with one, two, three, four, or five substituents independently selected from the group consisting of alkenyl, alkoxy, alkoxyalkyl, alkyl, cyano, halo, haloalkoxy, haloalkyl, hydroxy, hydroxy-alkyl, nitro, and oxo.

The term "aminoalkyl," as used herein, alone or in combination, refers to an amino group attached to the parent molecular moiety through an alkyl group. Examples include aminomethyl, aminoethyl and aminobutyl. The term "alkylamino" denotes amino groups which have been substituted with one or two alkyl radicals. Suitable "alkylamino" groups may be mono- or dialkylated, forming groups such as, for example, N-methylamino, N-ethylamino, N,N-dimethylamino, N,N-diethylamino and the like.

The terms "aminocarbonyl" and "carbamoyl," as used herein, alone or in combination, refer to an amino-substituted carbonyl group, wherein the amino group can be a primary or secondary amino group containing substituents selected from alkyl, aryl, aralkyl, cycloalkyl, cycloalkylalkyl radicals and the like.

The term "aminocarbonylalkyl," as used herein, alone or in combination, refers to an aminocarbonyl radical attached to an alkyl radical, as described above. An example of such radicals is aminocarbonylmethyl. The term "amidino" denotes an —C(NH)$NH_2$ radical. The term "cyanoamidino" denotes an —C(N—CN)$NH_2$ radical.

The term "aralkenyl" or "arylalkenyl," as used herein, alone or in combination, refers to an aryl group attached to the parent molecular moiety through an alkenyl group.

The term "aralkoxy" or "arylalkoxy," as used herein, alone or in combination, refers to an aryl group attached to the parent molecular moiety through an alkoxy group.

The term "aralkyl" or "arylalkyl," as used herein, alone or in combination, refers to an aryl group attached to the parent molecular moiety through an alkyl group.

The term "aralkylamino" or "arylalkylamino," as used herein, alone or in combination, refers to an arylalkyl group attached to the parent molecular moiety through a nitrogen atom, wherein the nitrogen atom is substituted with hydrogen.

The term "aralkylidene" or "arylalkylidene," as used herein, alone or in combination, refers to an aryl group attached to the parent molecular moiety through an alkylidene group The term "aralkylthio" or "arylalkylthio," as used herein, alone or in combination, refers to an arylalkyl group attached to the parent molecular moiety through a sulfur atom.

The term "aralkynyl" or "arylalkynyl," as used herein, alone or in combination, refers to an aryl group attached to the parent molecular moiety through an alkynyl group.

The term "aralkoxycarbonyl," as used herein, alone or in combination, refers to a radical of the formula aralkyl-O—C(O)— in which the term "aralkyl," has the significance given above. Examples of an aralkoxycarbonyl radical are benzyloxycarbonyl ("Z" or "Cbz") and 4-methoxyphenylmethoxycarbonyl ("MOS").

The term "aralkanoyl," as used herein, alone or in combination, refers to an acyl radical derived from an arylsubstituted alkanecarboxylic acid such as benzoyl, phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like. The term "aroyl" refers to an acyl radical derived from an arylcarboxylic acid, "aryl" having the meaning given below. Examples of such aroyl radicals include substituted and unsubstituted benzoyl or napthoyl such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "aryl," as used herein, alone or in combination, means a carbocyclic aromatic system containing one, two or three rings wherein such rings may be attached together in a pendent manner or may be fused. The term "aryl" embraces aromatic radicals such as phenyl, naphthyl, anthracenyl, phenanthryl, and biphenyl. The aryl groups of the present invention can be optionally substituted with one, two, three, four, or five substituents independently selected from the groups as defined herein.

The term "arylamino" as used herein, alone or in combination, refers to an aryl group attached to the parent moiety through an amino group, such as N-phenylamino, and the like.

The terms "arylcarbonyl" and "aroyl," as used herein, alone or in combination, refer to an aryl group attached to the parent molecular moiety through a carbonyl group.

The term "aryloxy," as used herein, alone or in combination, refers to an aryl group attached to the parent molecular moiety through an oxygen atom.

The term "arylsulfonyl," as used herein, alone or in combination, refers to an aryl group attached to the parent molecular moiety through a sulfonyl group.

The term "arylthio," as used herein, alone or in combination, refers to an aryl group attached to the parent molecular moiety through a sulfur atom.

The terms "carboxy" or "carboxyl," whether used alone or with other terms, such as "carboxyalkyl," denotes —$CO_2H$.

The terms "benzo" and "benz," as used herein, alone or in combination, refer to the divalent radical $C_6H_4$= derived from benzene. Examples include benzothiophene and benzimidazole.

The term "carbamoyloxy," as used herein, alone or in combination, refers to an amino-substituted carbonyl group attached to the parent molecular moiety through a oxygen atom (e.g. RR'NC(=O)O—), wherein the amino group can be a primary or secondary amino group containing substituents selected from alkyl, aryl, aralkyl, cycloalkyl, cycloalkylalkyl radicals and the like.

The term "O-carbamyl" as used herein, alone or in combination, refers to a —OC(O)NR, group—with R as defined herein.

The term "C-linked" as used herein, alone or in combination, refers to any substituent that is attached to the parent molecular moiety through a carbon-carbon bond.

The term "N-carbamyl" as used herein, alone or in combination, refers to a ROC(O)NH— group, with R as defined herein.

The term "carbonate" as used herein, alone or in combination, refers to a —O—C(=O)OR group, with R as defined herein.

The term "carbonyl," as used herein, when alone includes formyl [—C(O)H] and in combination is a —C(O)— group.

The term "carboxy," as used herein, refers to —C(O)OH or the corresponding "carboxylate" such as a carboxylic acid salt derivative or ester derivative. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," as used herein, alone or in combination, refers to a saturated or partially saturated monocyclic, bicyclic or tricyclic alkyl radical wherein each cyclic moiety contains from 3 to 12, preferably three to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by bicyclo[2,2,2]octane, bicyclo[2,2,2]octane, bicyclo[1,1,1]pentane, camphor and bicyclo[3,2,1]octane.

The term "cycloalkenyl," as used herein, alone or in combination, refers to a partially unsaturated monocyclic, bicyclic or tricyclic radical wherein each cyclic moiety contains from 3 to 12, preferably five to eight, carbon atom ring members and which may optionally be a benzo fused ring system which is optionally substituted as defined herein. Examples of such cycloalkenyl radicals include cyclopentenyl, cyclohexenyl, cyclohexadienyl, cycloheptenyl, cyclooctadienyl, -1H-indenyl and the like.

The term "cycloalkylalkyl," as used herein, alone or in combination, refers to an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

The term "cycloalkenylalkyl," as used herein, alone or in combination, refers to an alkyl radical as defined above which is substituted by a cycloalkenyl radical as defined above. Examples of such cycloalkenylalkyl radicals include 1-methylcyclohex-1-enyl-, 4-ethylcyclohex-1-enyl-, 1-butylcyclopent-1-enyl-, 3-methylcyclopent-1-enyl- and the like.

The term "ester," as used herein, alone or in combination, refers to a carbonyloxy —(C=O)O— group bridging two moieties linked at carbon atoms. Examples include ethyl benzoate, n-butyl cinnamate, phenyl acetate and the like.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, trichloroethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a halohydrocarbyl group attached at two or more positions. Examples include fluoromethylene (—CFH—), difluoromethylene (—$CF_2$—), chloromethylene (—CHCl—) and the like. Examples of such haloalkyl radicals include chloromethyl, 1-bromoethyl, fluoromethyl, difluoromethyl, trifluoromethyl, 1,1,1-trifluoroethyl, perfluorodecyl and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —$CH_2$—NH—$OCH_3$.

The term "heteroaryl," as used herein, alone or in combination, refers to an aromatic five- or six-membered ring, where at least one atom is selected from the group consisting of N, O, and S, and the remaining ring atoms are carbon. The five-membered rings have two double bonds, and the six-membered rings have three double bonds. The heteroaryl groups are connected to the parent molecular group through a substitutable carbon or nitrogen atom in the ring. The term "heteroaryl" also includes systems where a heteroaryl ring is fused to an aryl group, as defined herein, a heterocycle group, as defined herein, or an additional heteroaryl group. Heteroaryls are exemplified by benzothienyl, benzoxazolyl, benzofuranyl, benzimidazolyl, benzthiazolyl benzotriazolyl, cinnolinyl, furyl, imidazolyl, triazolyl [e.g., 4H-1,2,4-triazolyl, 1H-1,2,3-triazolyl, 2H-1,2,3-triazolyl, etc.], tetrazolyl

[e.g. 1H-tetrazolyl, 2H-tetrazolyl, etc.], indazolyl, indolyl, isoxazolyl, isoquinolinyl, isothiazolyl, naphthyridinyl, oxadiazolyl [e.g., 1,2,4-oxadiazolyl, 1,3,4-oxadiazolyl, 1,2,5-oxadiazolyl, etc.], oxazolyl, isoxazolyl, purinyl, thiazolyl, isothiazolyl, thienopyridinyl, thienyl, thiadiazolyl [e.g., 1,2,4-thiadiazolyl, 1,3,4-thiadiazolyl, 1,2,5-thiadiazolyl, etc.], pyridinyl, pyridazinyl, pyrimidinyl, pyrazinyl, pyrazolyl, pyrrolyl, pyrido[2,3-d]pyrimidinyl, pyrrolo[2,3-b]pyridinyl, quinazolinyl, quinolinyl, thieno[2,3-c]pyridinyl, tetrazolyl, triazinyl, and the like. The heteroaryl groups of the present invention can be optionally substituted with one, two, three, four, or five substituents independently selected from the groups as defined herein.

Examples of preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, triazolyl, and isoxazolyl The term "heteroaralkyl" or "heteroarylalkyl," as used herein, alone or in combination, refers to a heteroaryl group attached to the parent molecular moiety through an alkyl group.

The term "heteroaralkenyl" or "heteroarylalkenyl," as used herein, alone or in combination, refers to a heteroaryl group attached to the parent molecular moiety through an alkenyl group.

The term "heteroaralkoxy" or "heteroarylalkoxy," as used herein, alone or in combination, refers to a heteroaryl group attached to the parent molecular moiety through an alkoxy group.

The term "heteroaralkylidene" or "heteroarylalkylidene," as used herein, alone or in combination, refers to a heteroaryl group attached to the parent molecular moiety through an alkylidene group.

The term "heteroaryloxy," as used herein, alone or in combination, refers to a heteroaryl group attached to the parent molecular moiety through an oxygen atom.

The term "heteroarylsulfonyl," as used herein, alone or in combination, refers to a heteroaryl group attached to the parent molecular moiety through a sulfonyl group.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing one or more heteroatoms as ring members, wherein each said heteroatom may be independently selected from the group consisting of nitrogen, oxygen, and sulfur, and wherein there are typically 3 to 8 ring members in each ring. Most commonly heterocyclic rings contain 5 to 6 ring members. In some embodiments of this invention heterocyclic rings contain 1 to 4 heteroatoms; in other embodiments, heterocyclic rings contain 1 to 2 heteroatoms. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "heterocycloalkenyl," as used herein, alone or in combination, refers to a heterocycle group attached to the parent molecular moiety through an alkenyl group.

The term "heterocycloalkoxy," as used herein, alone or in combination, refers to a heterocycle group attached to the parent molecular group through an oxygen atom.

The term "heterocycloalkylalkyl," as used herein, alone or in combination, refers to an alkyl radical as defined above in which at least one hydrogen atom is replaced by a heterocycloalkyl radical as defined above, such as pyrrolidinylmethyl, tetrahydrothienylmethyl, pyridylmethyl and the like.

The term "heterocycloalkylidene," as used herein, alone or in combination, refers to a heterocycle group attached to the parent molecular moiety through an alkylidene group.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl" as used herein, alone or in combination, refers to a linear or branched alkyl group having one to about ten carbon atoms any one of which may be substituted with one or more hydroxyl radicals. Examples of such radicals include hydroxymethyl, hydroxyethyl, hydroxypropyl, hydroxybutyl and hydroxyhexyl.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein in such terms as "lower alkyl," alone or in combination, means containing from 1 to and including 6 carbon atoms.

The term "mercaptoalkyl" as used herein, alone or in combination, refers to an R'SR— group, where R and R' are as defined herein.

The term "mercaptomercaptyl" as used herein, alone or in combination, refers to a RSR'S— group, where R is as defined herein.

The term "mercaptyl" as used herein, alone or in combination, refers to an RS— group, where R is as defined herein.

The term "null" refers to a lone electron pair.

The term "nitro," as used herein, alone or in combination, refers to —$NO_2$.

The term "optionally substituted" means the anteceding group may be substituted or unsubstituted. When substituted, the hydrogen atoms bound to the carbon, nitrogen, sulfur, or oxygen atoms are replaced by "substituents" which may include carbonyl (oxo), carboxyl, lower alkyl carboxylate, lower alkyl carbonate, lower alkyl carbamate, halogen, hydroxy, amino, amido, cyano, hydrazinyl, hydrazinylcarbonyl, alkylhydrazinyl, dialkylhydrazinyl, arylhydrazinyl, heteroarylhydrazinyl, nitro, thiol, sulfonic acid, trisubstituted silyl, urea, acyl, acyloxy, acylamino, acylthio, lower alkyl, lower alkylamino, lower dialkylamino, lower alkyloxy, lower alkoxyalkyl, lower alkylthio, lower alkylsulfonyl, lower alkenyl, lower alkenylamino, lower dialkenylamino, lower alkenyloxy, lower alkenylthio, lower alkenyl sulfonyl, lower alkynyl, lower alkynylamino, lower dialkynylamino, lower alkynyloxy, lower alkynylthio, lower alkynylsulfonyl, lower cycloalkyl, lower cycloalkyloxy, lower cycloalkylamino, lower cycloalkylthio, lower cycloalkylsulfonyl, lower cycloalkylalkyl, lower cycloalkylalkyloxy, lower cycloalkylalkylamino, lower cycloalkylalkylthio, lower cycloalkylalkylsulfonyl, aryl, aryloxy, arylamino, arylthio, arylsulfonyl, arylalkyl, arylalkyloxy, arylalkylamino, arylalkylthio, arylalkylsulfonyl, heteroaryl, heteroaryloxy, heteroarylamino, heteroarylthio, heteroarylsulfonyl, heteroarylalkyl, heteroarylalkyloxy, heteroarylalkylamino, heteroarylalkylthio, heteroarylalkylsulfonyl, heterocycloalkyl, heterocycloalkyloxy, heterocycloalkylamino, heterocycloalkylthio, heterocycloalkylsulfonyl, lower haloalkyl, lower haloalkenyl, lower haloalkynyl, lower perhaloalkyl, lower perhaloalkoxy, lower haloalkoxy, and lower acyloxy. Two substituents may be joined together to form a fused four-, five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. All pendant aryl, heteroaryl, and heterocyclo moieties can be further optionally substituted with one, two, three, four, or five substituents independently selected from the groups listed above.

The terms "oxy" or "oxa," as used herein, alone or in combination, refer to —O—.

The term "oxo" as used herein, alone or in combination, refers to a doubly bonded oxygen =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "phosphonate" as used herein, alone or in combination, refers to the —P(=O)(OG)(OG1) group, where G and G1 are chosen from H, alkyl, alkenyl, alkynyl, aryl, heteroaryl, etc.

The term "phosphinate" as used herein, alone or in combination, refers to the —P(=O)(G)(OG1) group, where G and G1 are chosen from H, alkyl, alkenyl, alkynyl, aryl, heteroaryl, etc.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S and —S—.

The term "sulfinyl," as used herein, alone or in combination, refers to —S(O)—.

The term "sulfonyl," as used herein, alone or in combination, refers to —$SO_2$—.

The term "N-sulfonamido" refers to a $RS(=O)_2NH$— group with R as defined herein.

The term "S-sulfonamido" refers to a —$S(=O)_2NR_2$, group, with R as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thioether," as used herein, alone or in combination, refers to a thio group bridging two moieties linked at carbon atoms.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NH— group, with R as defined herein.

The term "O-thiocarbamyl" refers to a —OC(S)NR, group with R as defined herein.

The term "thiocyanato" refers to a —CNS group.

The term "trihalomethanesulfonamido" refers to a $X_3CS(O)_2NR$— group with X is a halogen and R as defined herein.

The term "trihalomethanesulfonyl" refers to a $X_3CS(O)_2$— group where X is a halogen.

The term "trihalomethoxy" refers to a $X_3CO$— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

The term "urea," as used herein, alone or in combination, refers to —N(R)C(=O)N(R)(R), with R as defined herein.

The term "carrier" is used in its broadest sense. For example, the term carrier refers to any carriers, diluents, excipients, wetting agents, buffering agents, suspending agents, lubricating agents, adjuvants, vehicles, delivery systems, emulsifiers, disintegrants, absorbents, preservatives, surfactants, colorants, flavorants, and sweeteners. In some embodiments, the carrier may be a pharmaceutically acceptable carrier, a term narrower than carrier, because the term pharmaceutically acceptable carrier" means a non-toxic that would be suitable for use in a pharmaceutical composition.

The present invention also relates to a pharmaceutical composition comprising, in a pharmaceutically acceptable carrier, an effective amount of at least one compound of the invention.

The term effective amount is used in its broadest sense. The term, for example, refers to the amount required to produce a desired effect.

In some embodiments, the compound of the invention is present in a pharmaceutical composition in an effective amount for treating HCV infection (e.g., chronic HCV infection). "Treating HCV infection" may refers to: (i) preventing HCV infection from occurring in an animal that may be predisposed to HCV infection but has not yet been diagnosed as having it; (ii) inhibiting or slowing HCV infection, e.g. arresting its development; (iii) relieving chronic infection, e.g. causing its regression; (iv) improving a symptom in a subject having chronic infection; and/or (v) prolonging the survival of a subject having chronic infection.

In any embodiment of the compounds of formula (I), $R_1$ through $R_5$ may be the same, may be different, or some members of $R_1$ through $R_5$ may be the same while the others are different. Any combination is possible.

Examples of compounds of the present invention may include, but are not limited to the following compounds listed in Table 1 below:
TABLE 1
| No. | Structure |
|---|---|
| 1 | 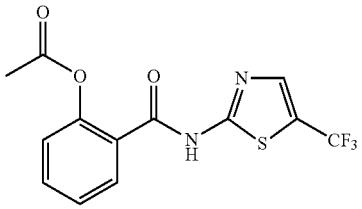 |
| 2 | 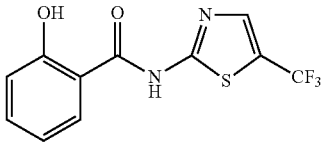 |
| 3 | 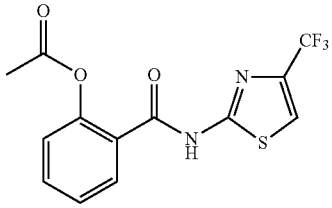 |
| 4 | 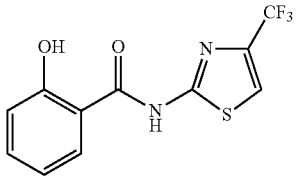 |
| 5 | 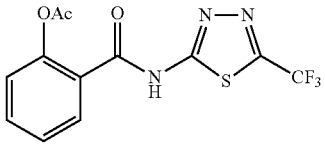 |
| 6 | 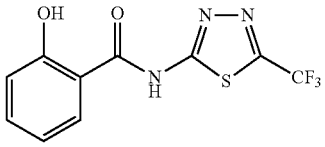 |
| 7 | 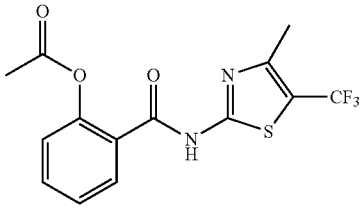 |
| 8 | 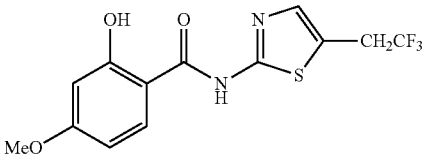 |
TABLE 1-continued
| No. | Structure |
|---|---|
| 9 | 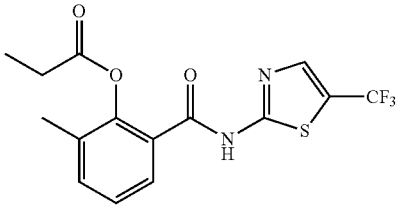 |
| 10 | 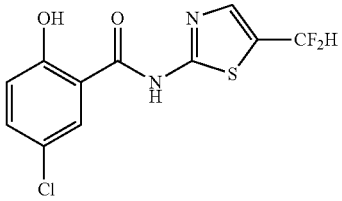 |
| 11 | 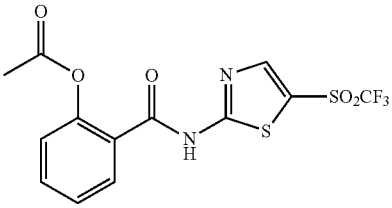 |
| 12 | 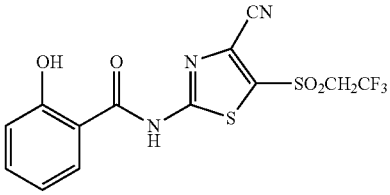 |
| 13 | 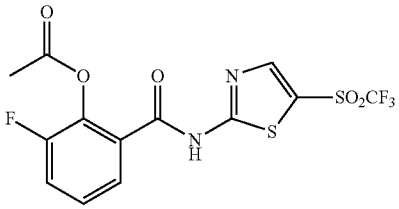 |
| 14 | 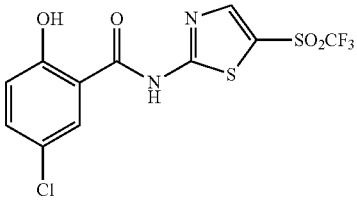 |
| 15 | 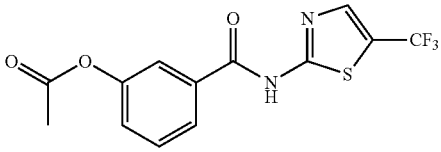 |
| 16 | 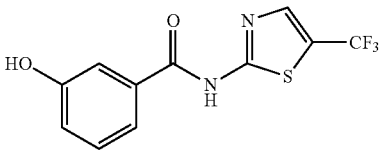 |

TABLE 1-continued
| No. | Structure |
|---|---|
| 17 | 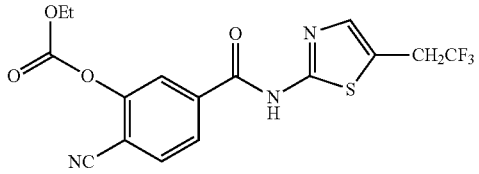 |
| 18 | 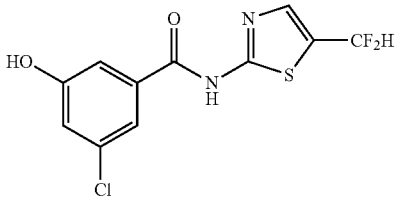 |
| 19 | 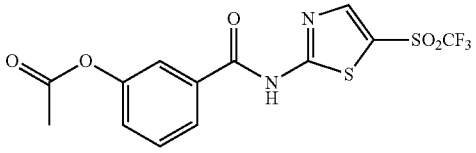 |
| 20 | 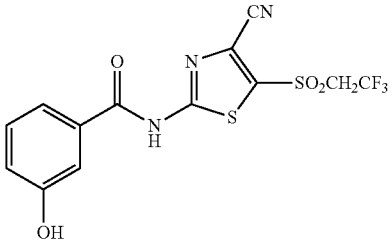 |
| 21 | 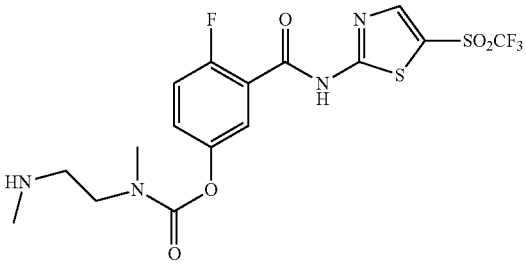 |
| 22 | 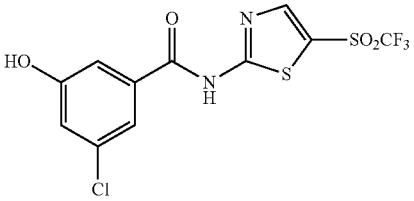 |
| 23 | 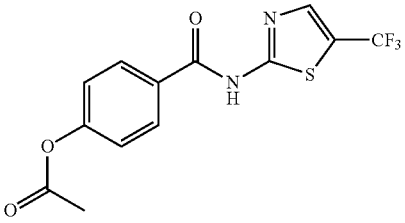 |
TABLE 1-continued
| No. | Structure |
|---|---|
| 24 | 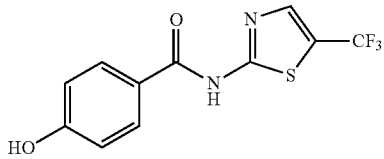 |
| 25 | 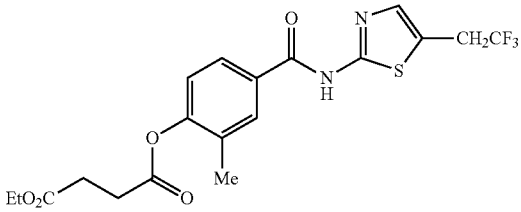 |
| 26 | 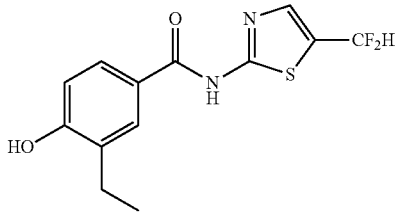 |
| 27 | 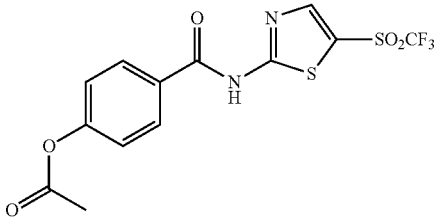 |
| 28 | 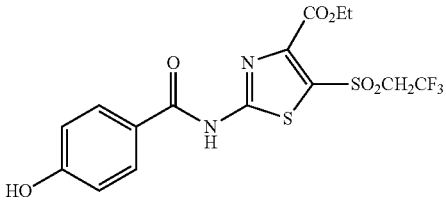 |
| 29 | 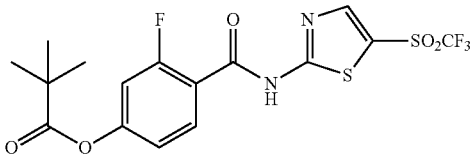 |
| 30 | 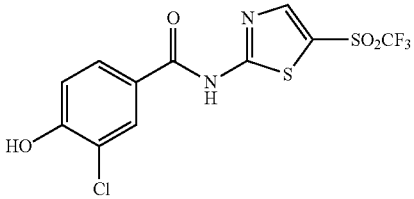 |

TABLE 1-continued
| No. | Structure |
|---|---|
| 31 | 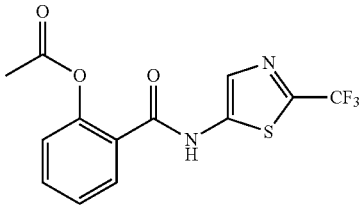 |
| 32 | 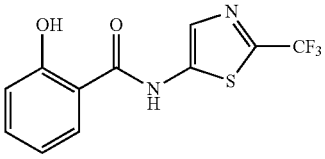 |
| 33 | 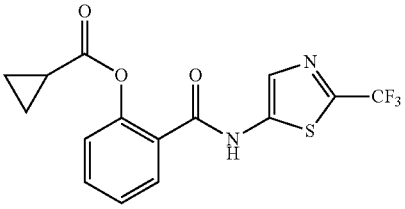 |
| 34 | 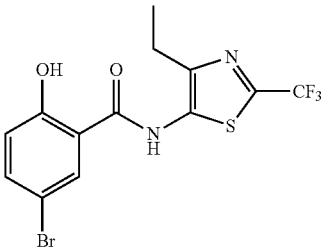 |
| 35 | 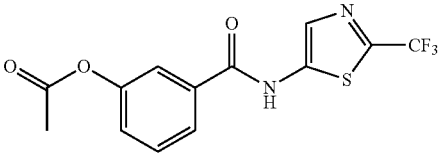 |
| 36 | 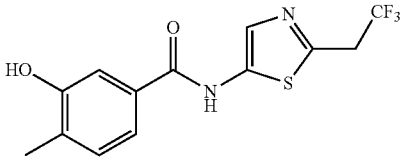 |
| 37 | 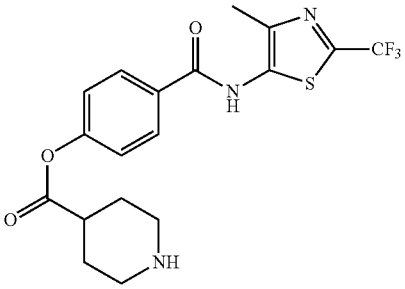 |
TABLE 1-continued
| No. | Structure |
|---|---|
| 38 | 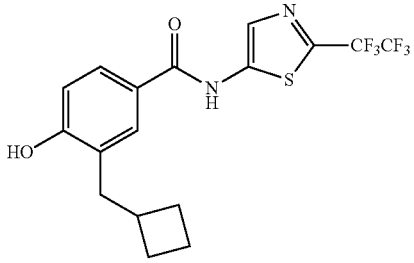 |
| 39 | 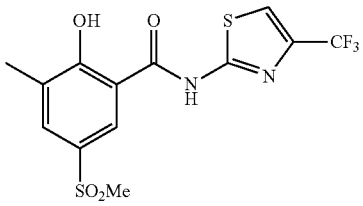 |
| 40 | 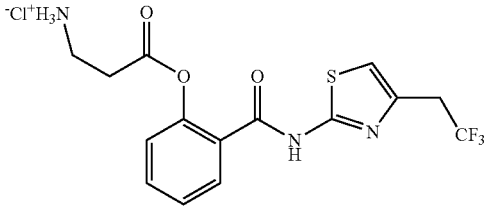 |
| 41 | 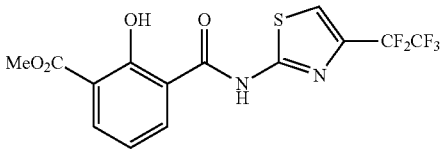 |
| 42 | 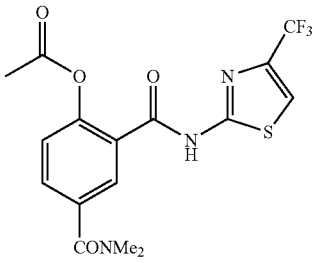 |
| 43 | 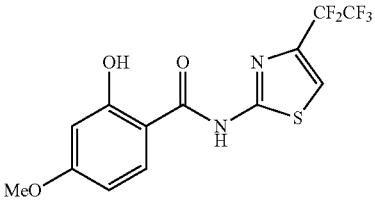 |
| 44 | 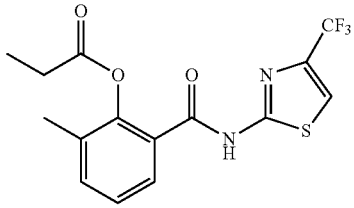 |

TABLE 1-continued
| No. | Structure |
|---|---|
| 45 | 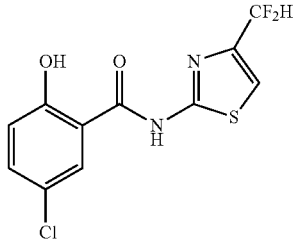 |
| 46 | 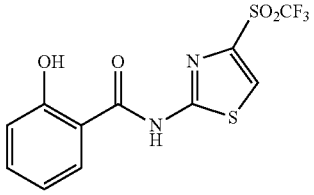 |
| 47 | 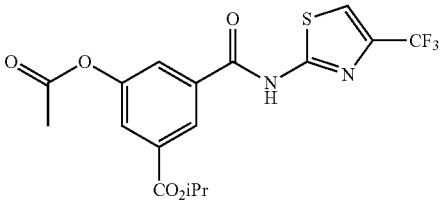 |
| 48 | 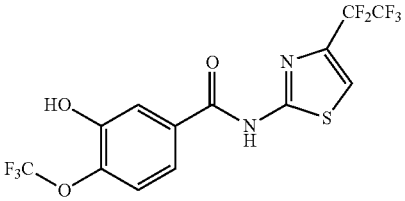 |
| 49 | 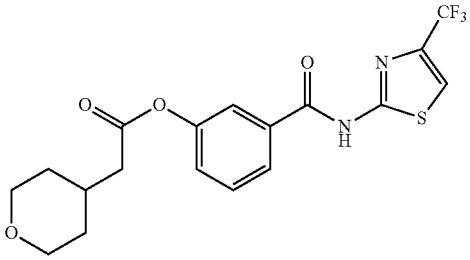 |
| 50 | 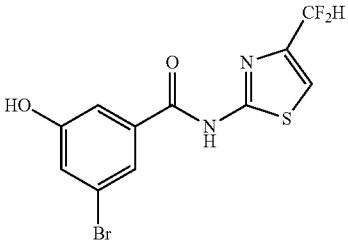 |
| 51 | 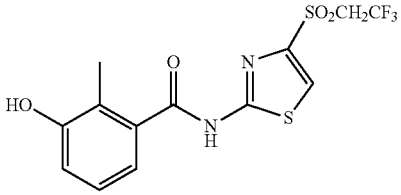 |
TABLE 1-continued
| No. | Structure |
|---|---|
| 52 | 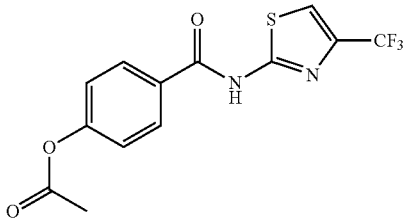 |
| 53 | 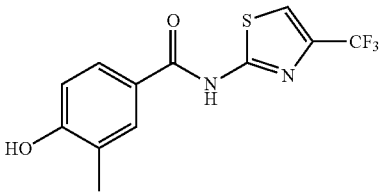 |
| 54 | 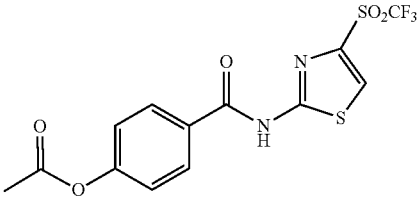 |
| 55 | 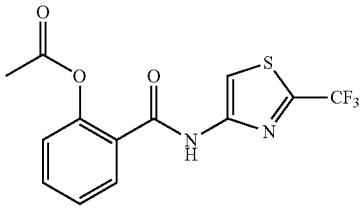 |
| 56 | 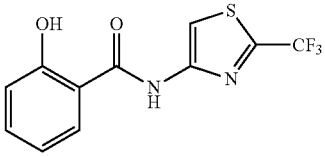 |
| 57 | 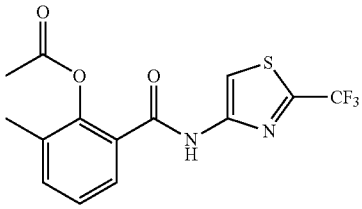 |
| 58 | 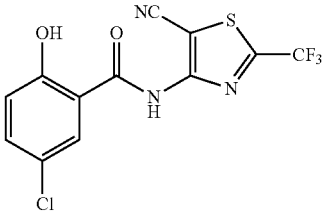 |

TABLE 1-continued
| No. | Structure |
|---|---|
| 59 | 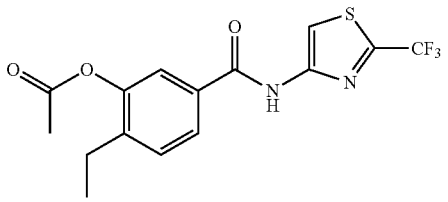 |
| 60 | 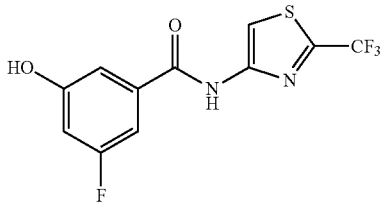 |
| 61 | 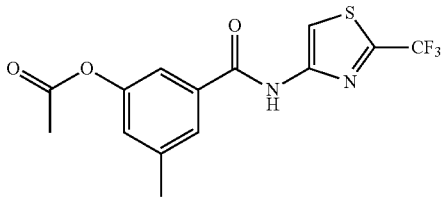 |
| 62 | 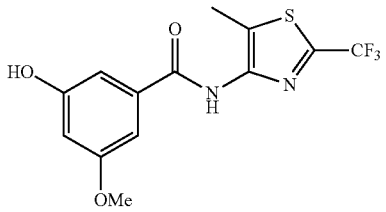 |
| 63 | 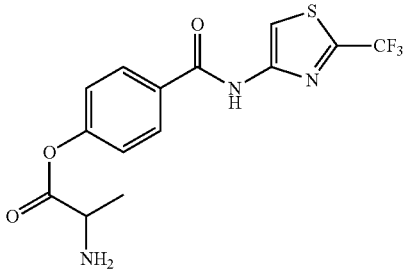 |
| 64 | 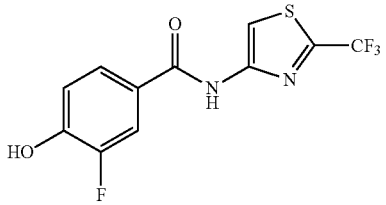 |
TABLE 1-continued
| No. | Structure |
|---|---|
| 65 | 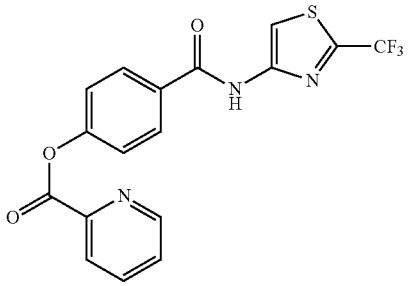 |
| 66 | 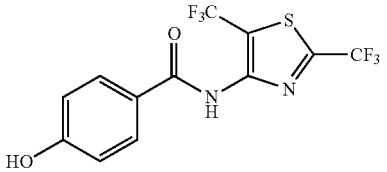 |
| 67 | 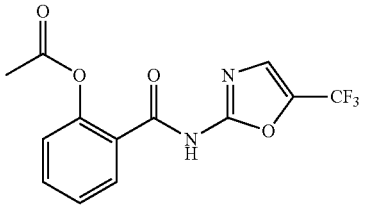 |
| 68 | 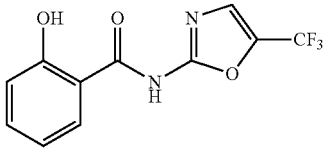 |
| 69 | 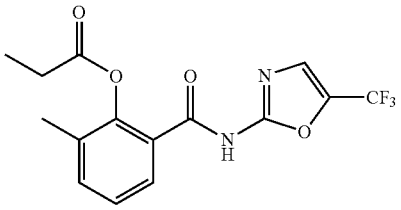 |
| 70 | 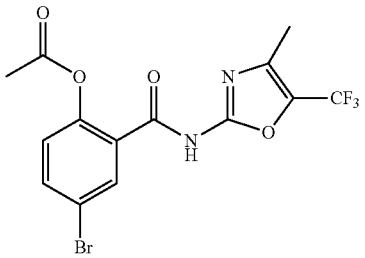 |
| 71 | 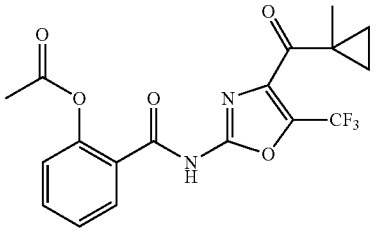 |

TABLE 1-continued
| No. | Structure |
|---|---|
| 72 | 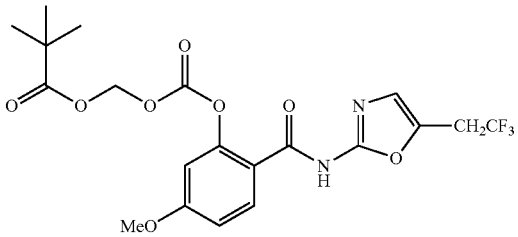 |
| 73 | 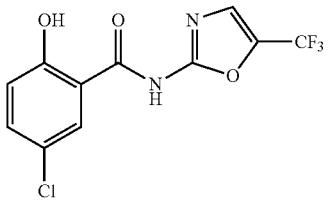 |
| 74 | 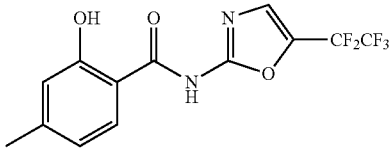 |
| 75 | 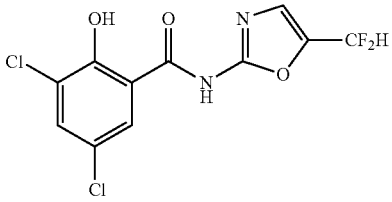 |
| 76 | 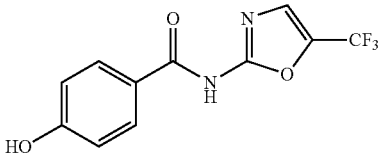 |
| 77 | 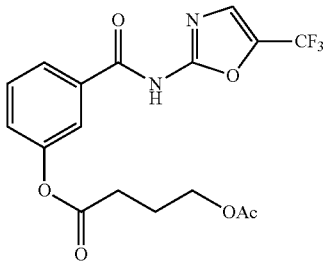 |
| 78 | 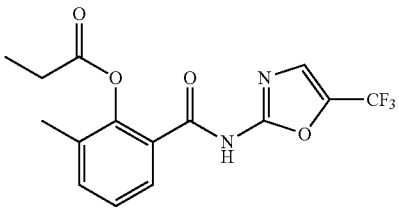 |
TABLE 1-continued
| No. | Structure |
|---|---|
| 79 | 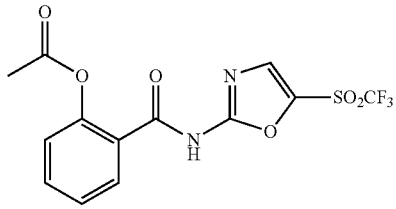 |
| 80 | 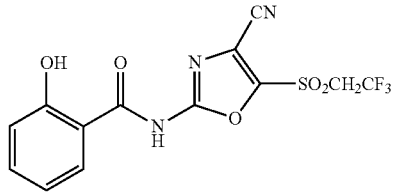 |
| 81 | 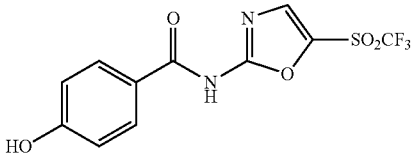 |
| 82 | 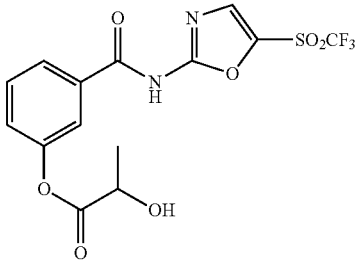 |
| 83 | 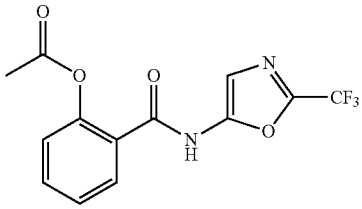 |
| 84 | 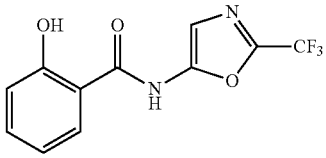 |
| 85 | 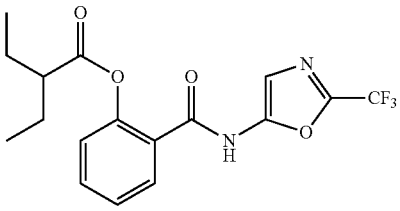 |

TABLE 1-continued
| No. | Structure |
|---|---|
| 86 | 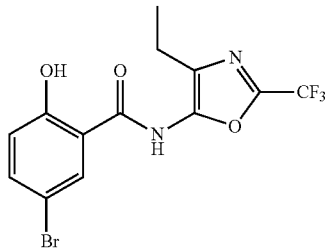 |
| 87 | 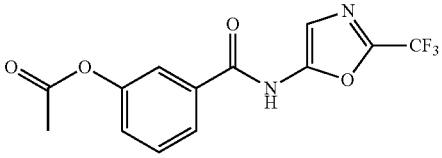 |
| 88 | 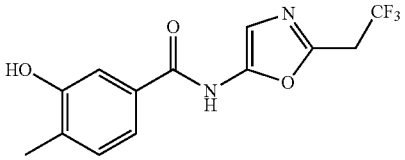 |
| 89 | 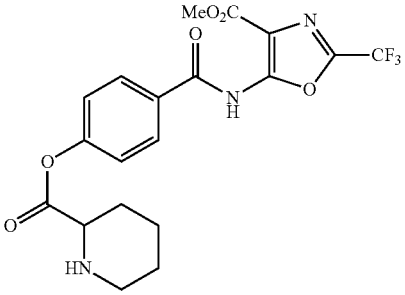 |
| 90 | 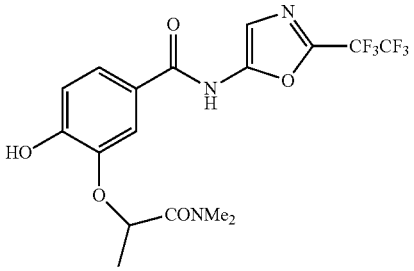 |
| 91 | 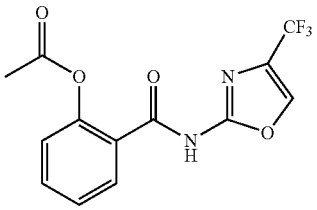 |
| 92 | 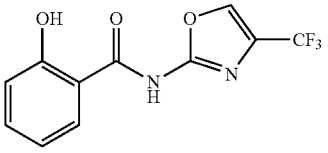 |
TABLE 1-continued
| No. | Structure |
|---|---|
| 93 | 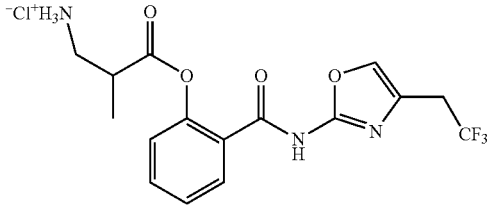 |
| 94 | 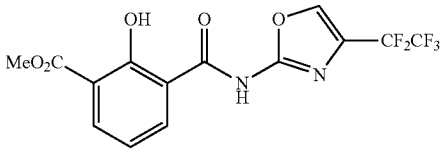 |
| 95 | 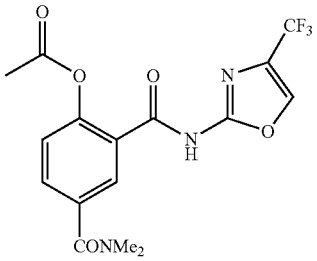 |
| 96 | 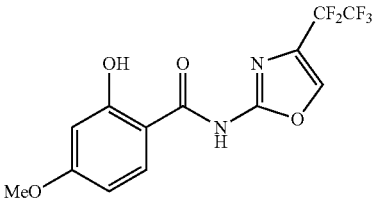 |
| 97 | 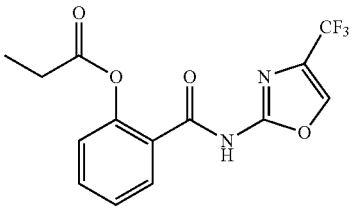 |
| 98 | 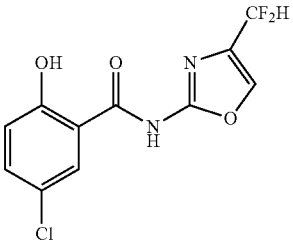 |
| 99 | 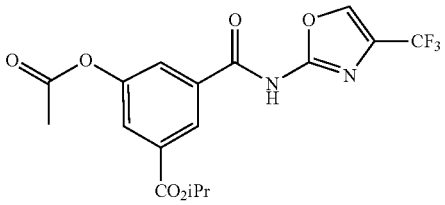 |

TABLE 1-continued
| No. | Structure |
|---|---|
| 100 | 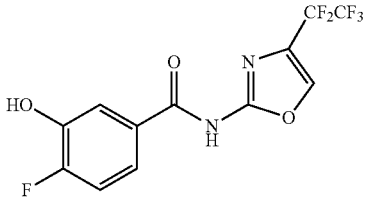 |
| 101 | 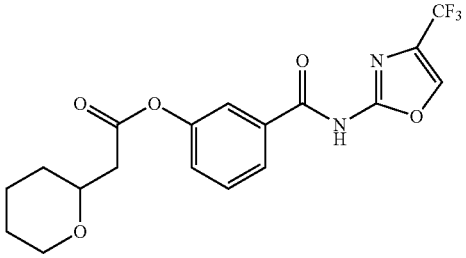 |
| 102 | 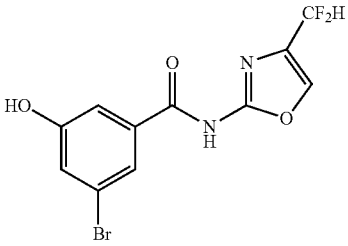 |
| 103 | 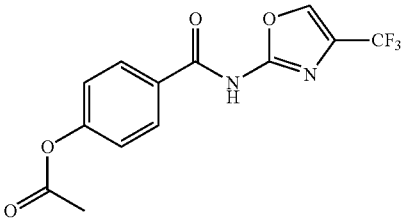 |
| 104 | 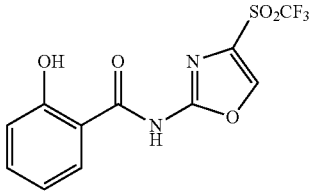 |
| 105 | 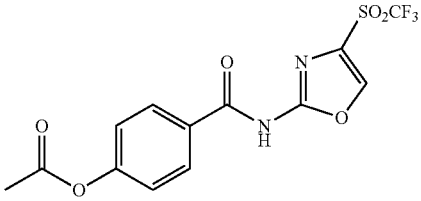 |
| 106 | 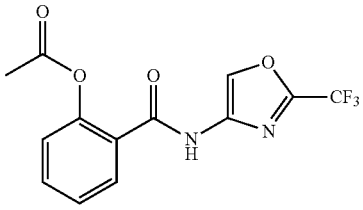 |
TABLE 1-continued
| No. | Structure |
|---|---|
| 107 | 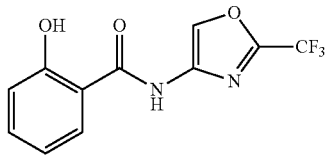 |
| 108 | 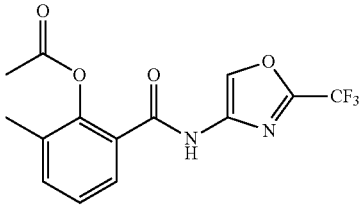 |
| 109 | 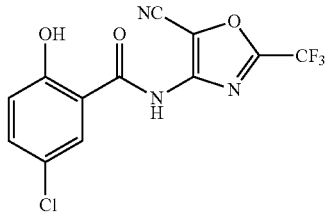 |
| 110 | 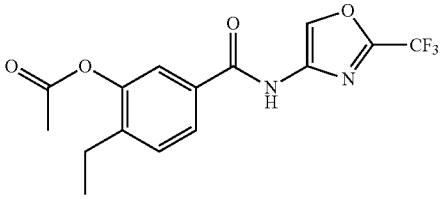 |
| 111 | 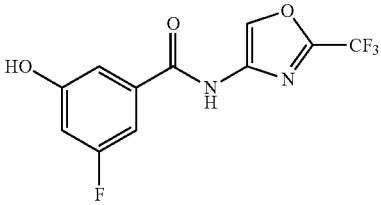 |
| 112 | 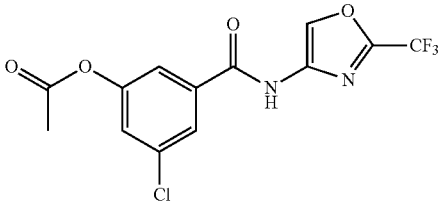 |
| 113 | 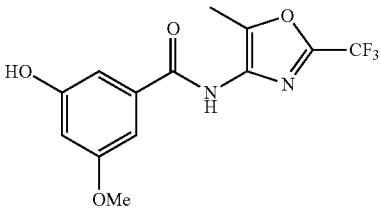 |

TABLE 1-continued
| No. | Structure |
|---|---|
| 114 | 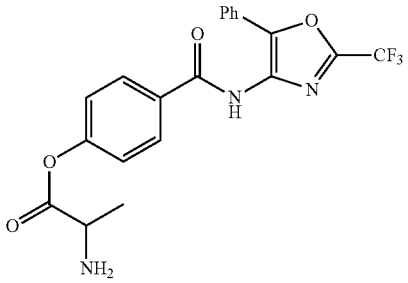 |
| 115 | 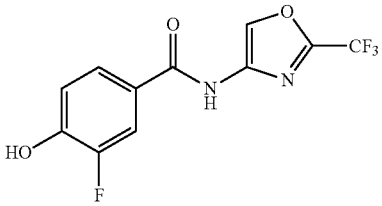 |
| 116 | 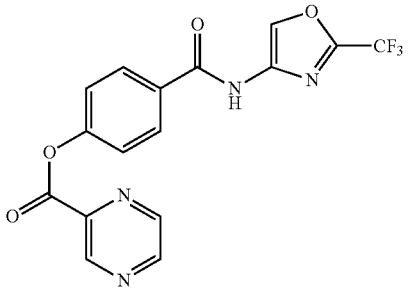 |
| 117 | 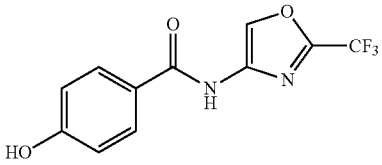 |
| 118 | 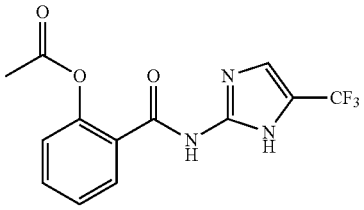 |
| 119 | 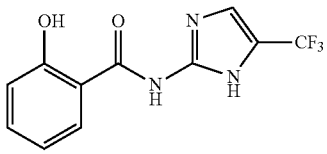 |
| 120 | 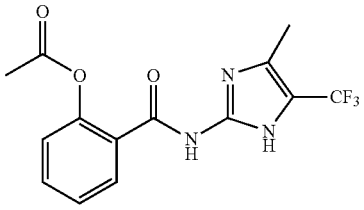 |
TABLE 1-continued
| No. | Structure |
|---|---|
| 121 | 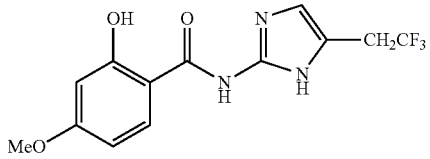 |
| 122 | 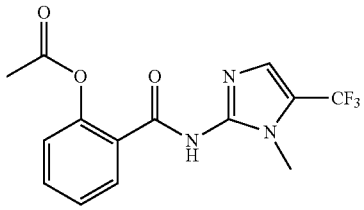 |
| 123 | 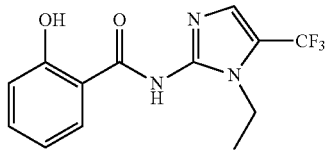 |
| 124 | 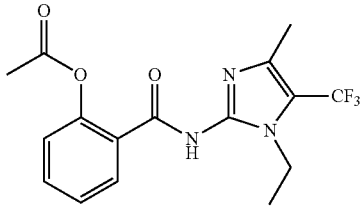 |
| 125 | 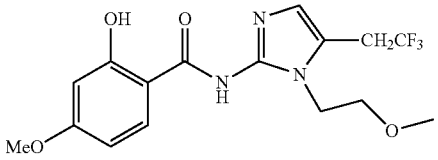 |
| 126 | 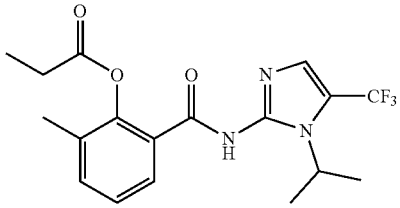 |
| 127 | 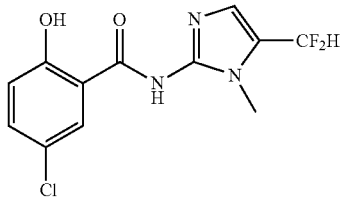 |
| 128 | 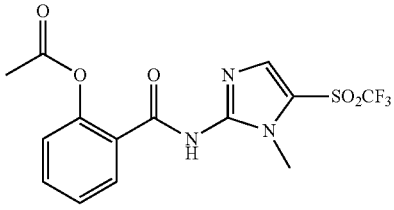 |

TABLE 1-continued
| No. | Structure |
|---|---|
| 129 | 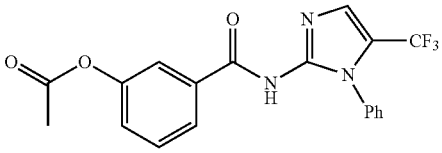 |
| 130 | 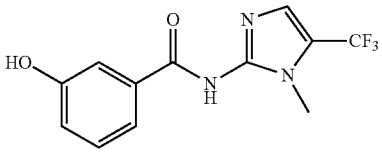 |
| 131 | 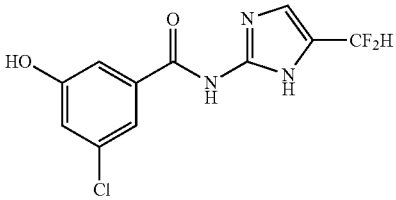 |
| 132 | 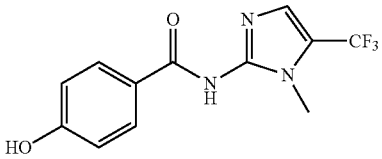 |
| 133 | 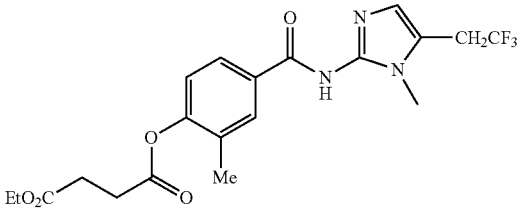 |
| 134 | 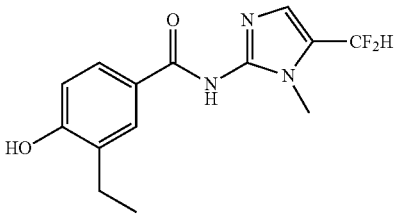 |
| 135 | 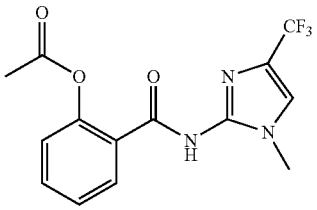 |
| 136 | 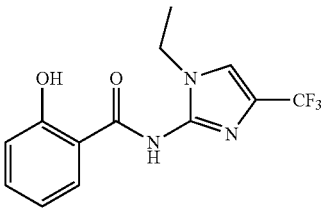 |
TABLE 1-continued
| No. | Structure |
|---|---|
| 137 | 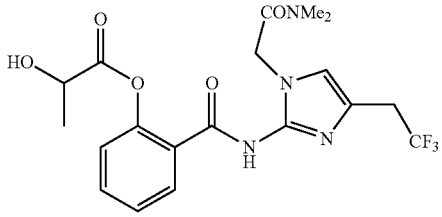 |
| 138 | 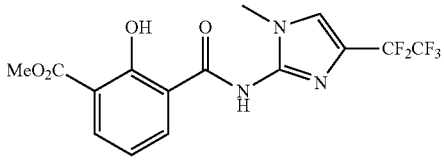 |
| 139 | 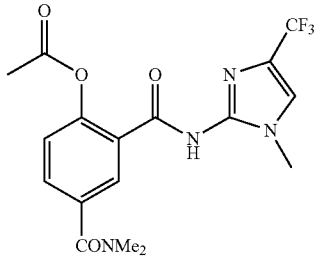 |
| 140 | 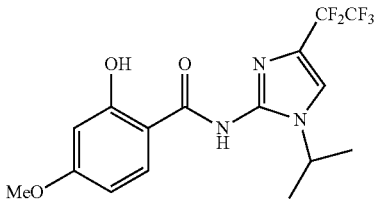 |
| 141 | 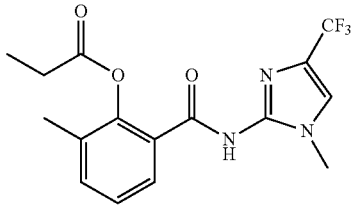 |
| 142 | 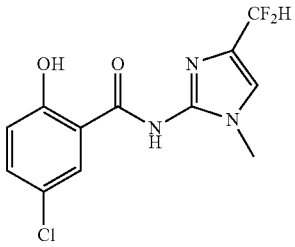 |

TABLE 1-continued
| No. | Structure |
|---|---|
| 143 | 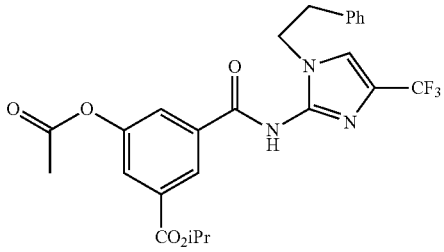 |
| 144 | 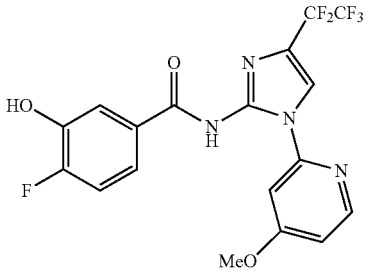 |
| 145 | 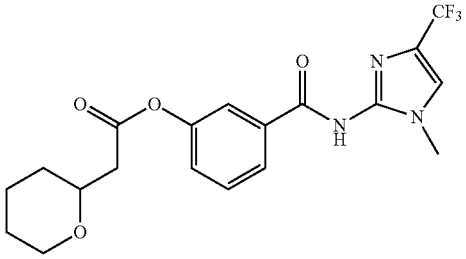 |
| 146 | 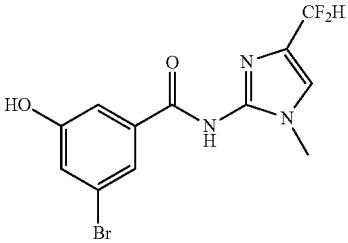 |
| 147 | 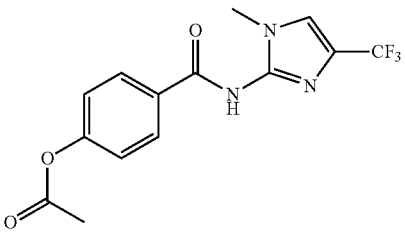 |
| 148 | 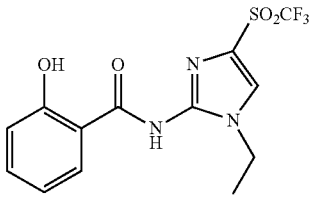 |
TABLE 1-continued
| No. | Structure |
|---|---|
| 149 | 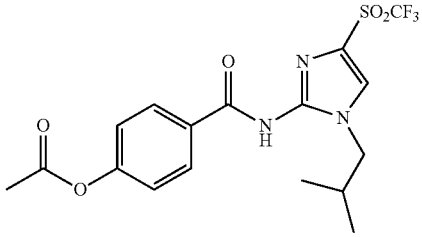 |
| 150 | 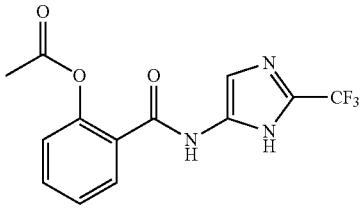 |
| 151 | 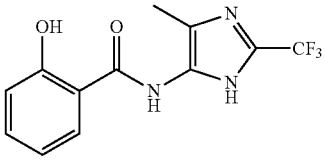 |
| 152 | 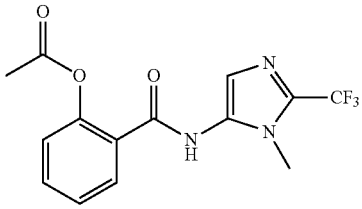 |
| 153 | 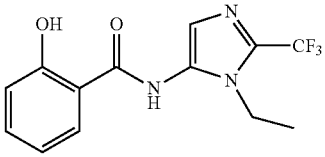 |
| 154 | 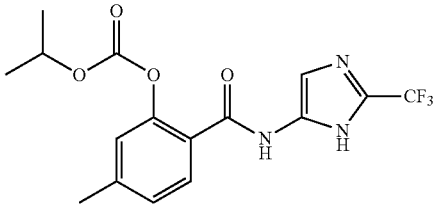 |
| 155 | 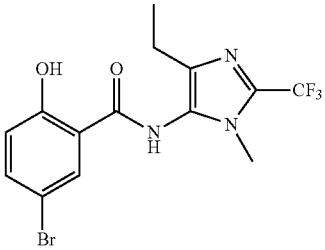 |

TABLE 1-continued
| No. | Structure |
|---|---|
| 156 | 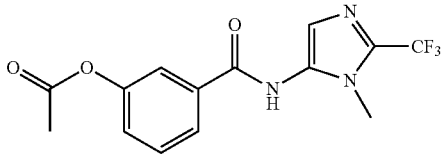 |
| 157 | 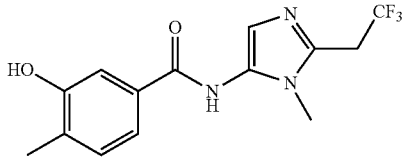 |
| 158 | 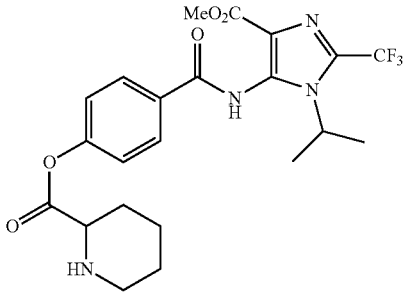 |
| 159 | 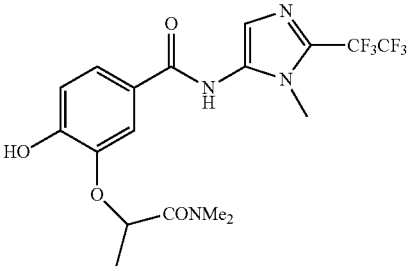 |
| 160 | 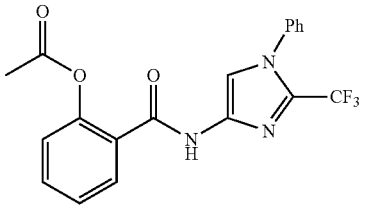 |
| 161 | 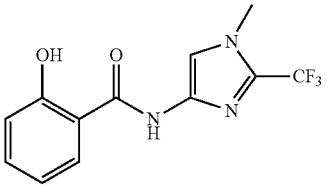 |
| 162 | 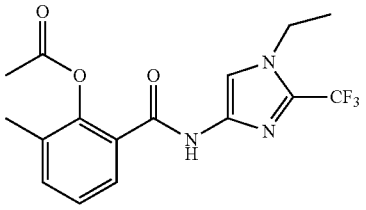 |
TABLE 1-continued
| No. | Structure |
|---|---|
| 163 | 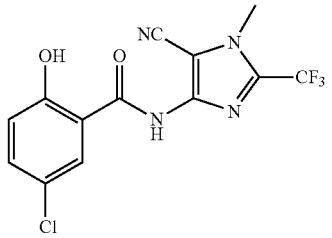 |
| 164 | 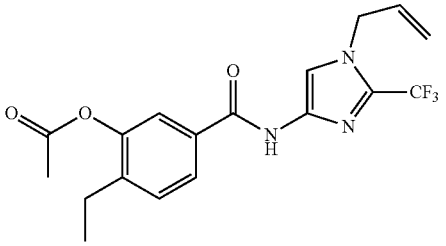 |
| 165 | 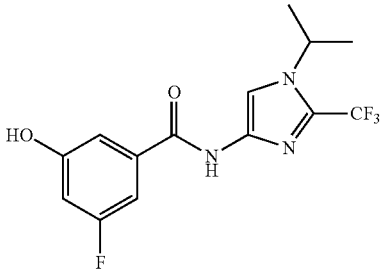 |
| 166 | 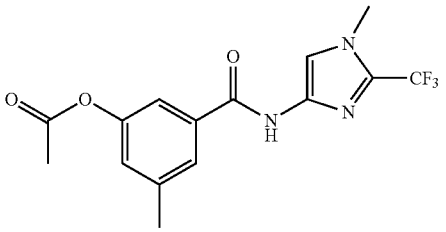 |
| 167 | 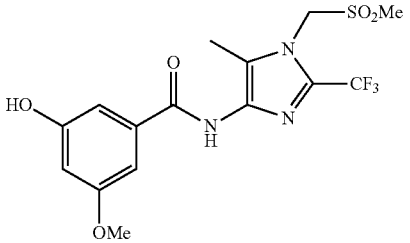 |
| 168 | 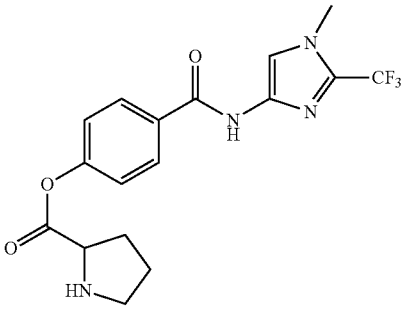 |

TABLE 1-continued
| No. | Structure |
|---|---|
| 169 | 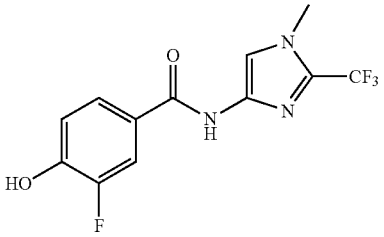 |
| 170 | 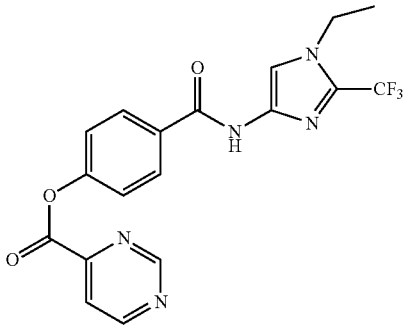 |
| 171 | 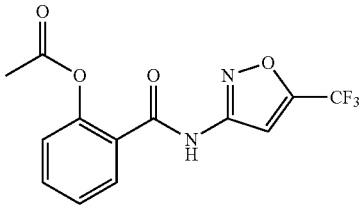 |
| 172 | 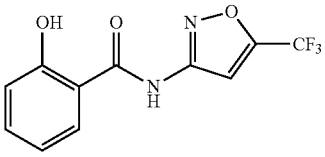 |
| 173 | 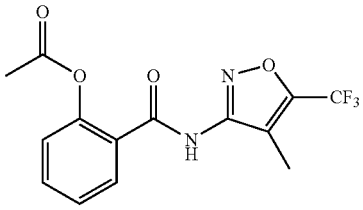 |
| 174 | 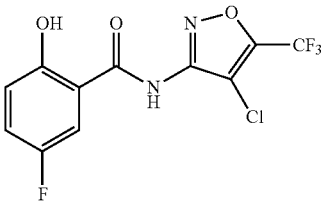 |
| 175 | 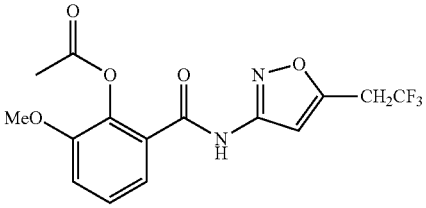 |
TABLE 1-continued
| No. | Structure |
|---|---|
| 176 | 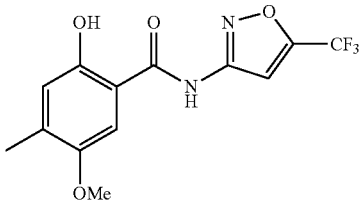 |
| 177 | 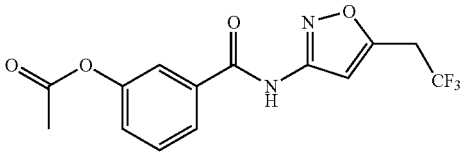 |
| 178 | 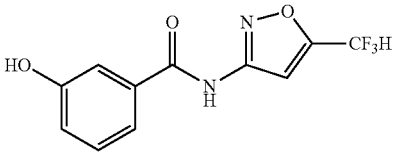 |
| 179 | 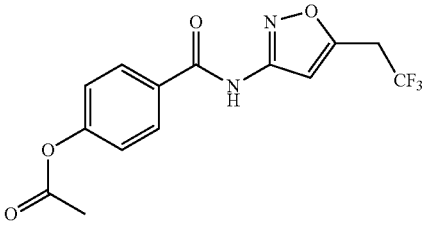 |
| 180 | 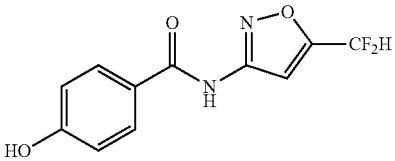 |
| 181 | 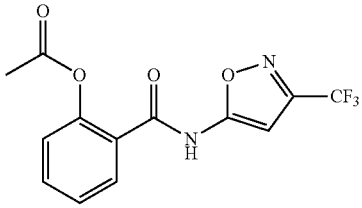 |
| 182 | 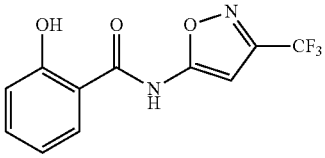 |
| 183 | 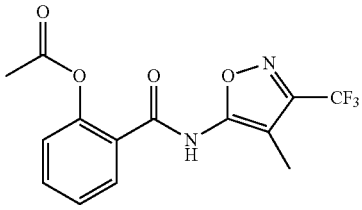 |

TABLE 1-continued
| No. | Structure |
|---|---|
| 184 | 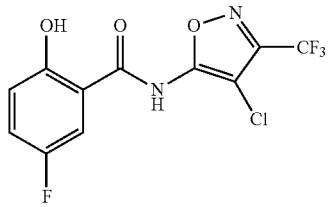 |
| 185 | 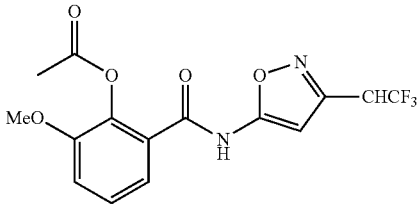 |
| 186 | 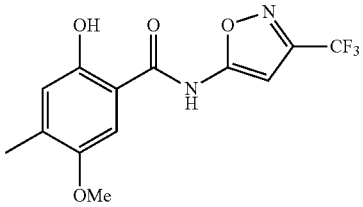 |
| 187 | 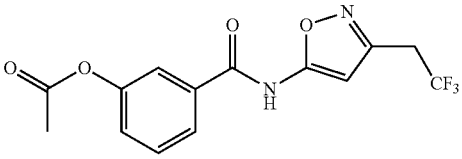 |
| 188 | 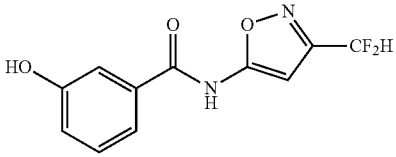 |
| 189 | 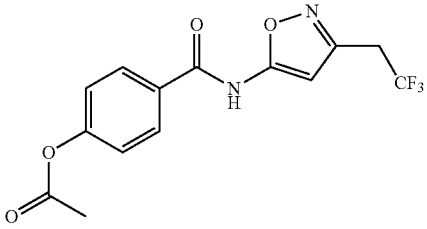 |
| 190 | 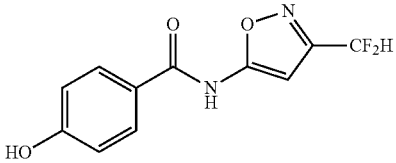 |
TABLE 1-continued
| No. | Structure |
|---|---|
| 191 | 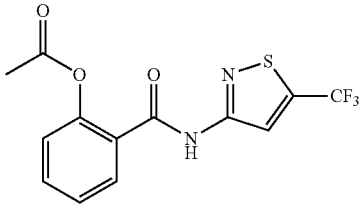 |
| 192 | 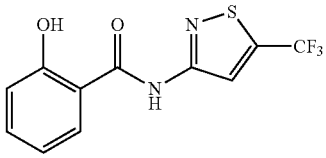 |
| 193 | 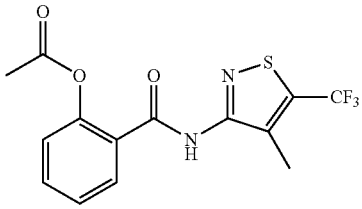 |
| 194 | 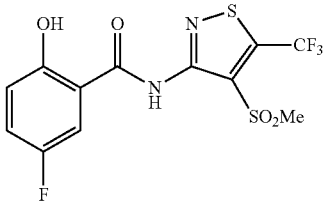 |
| 195 | 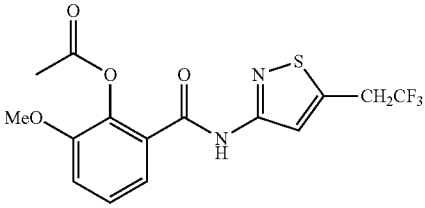 |
| 196 | 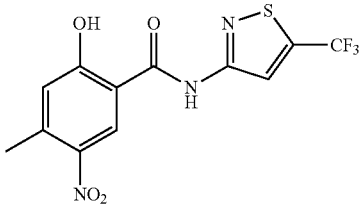 |
| 197 | 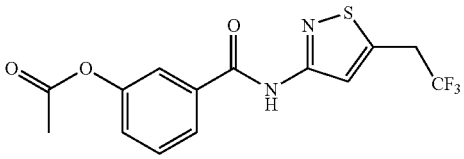 |
| 198 | 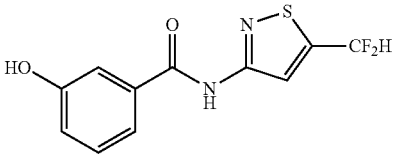 |

TABLE 1-continued
| No. | Structure |
|---|---|
| 199 | 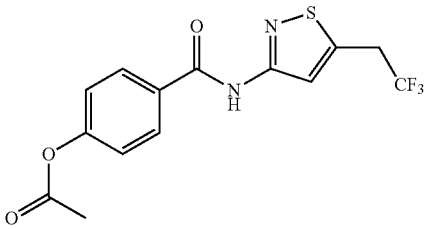 |
| 200 | 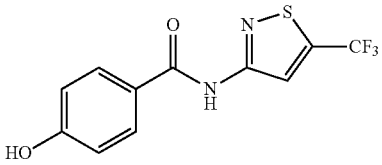 |
| 201 | 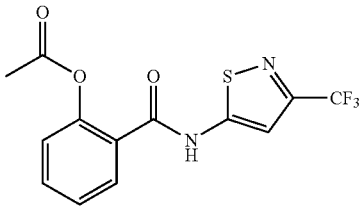 |
| 202 | 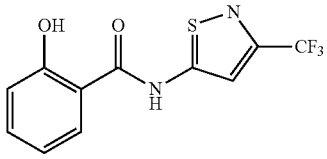 |
| 203 | 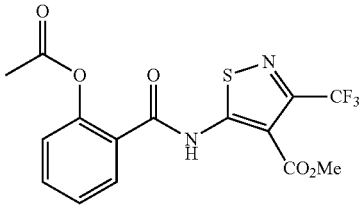 |
| 204 | 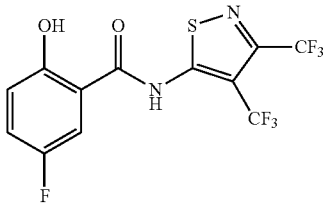 |
| 205 | 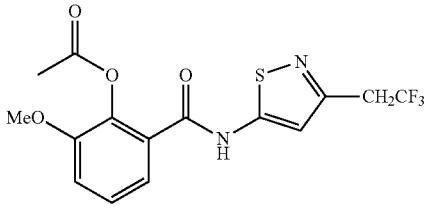 |
TABLE 1-continued
| No. | Structure |
|---|---|
| 206 | 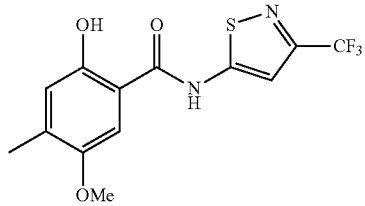 |
| 207 | 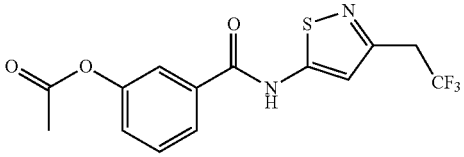 |
| 208 | 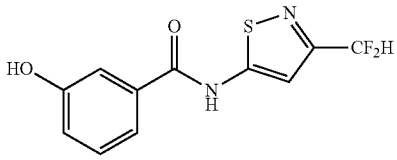 |
| 209 | 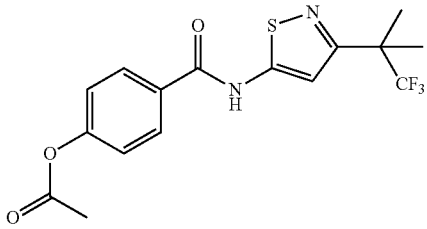 |
| 210 | 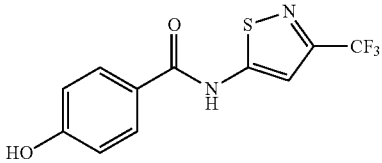 |
| 211 | 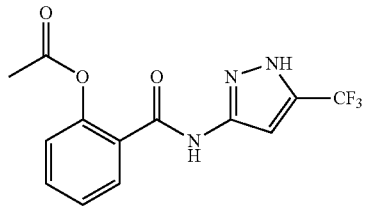 |
| 212 | 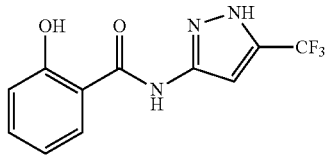 |
| 213 | 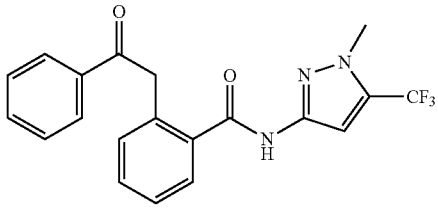 |

TABLE 1-continued
| No. | Structure |
|---|---|
| 214 | 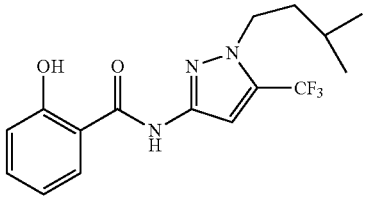 |
| 215 | 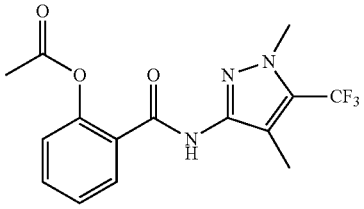 |
| 216 | 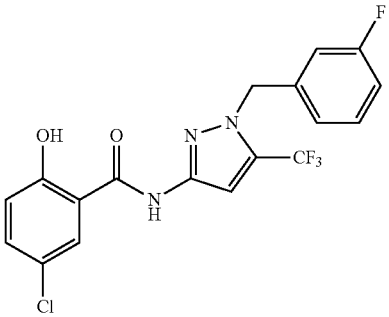 |
| 217 | 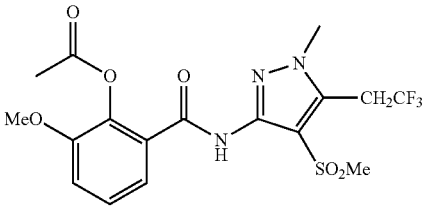 |
| 218 | 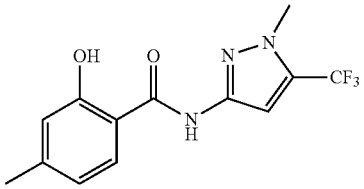 |
| 219 | 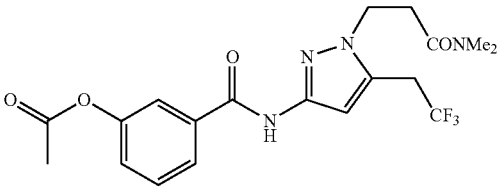 |
| 220 | 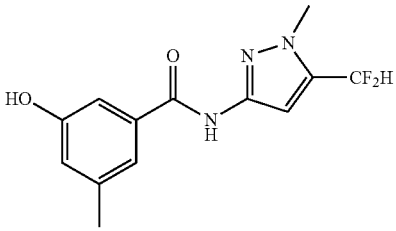 |
TABLE 1-continued
| No. | Structure |
|---|---|
| 221 | 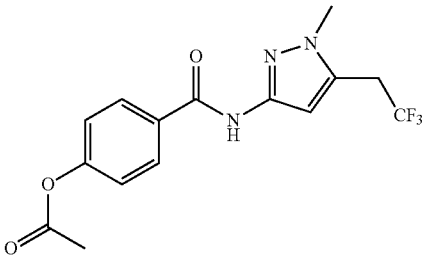 |
| 222 | 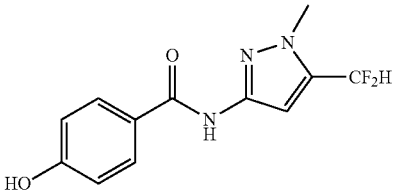 |
| 223 | 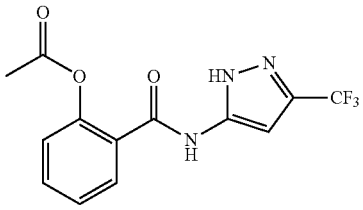 |
| 224 | 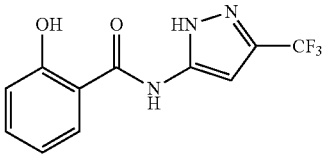 |
| 225 | 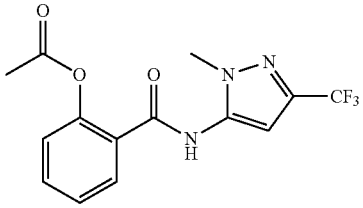 |
| 226 | 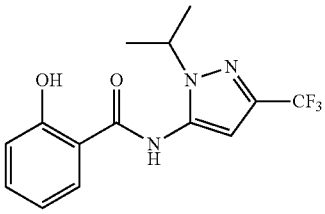 |
| 227 | 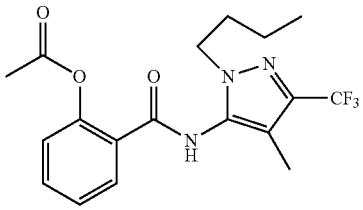 |

TABLE 1-continued
| No. | Structure |
|---|---|
| 228 | 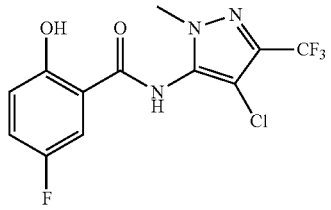 |
| 229 | 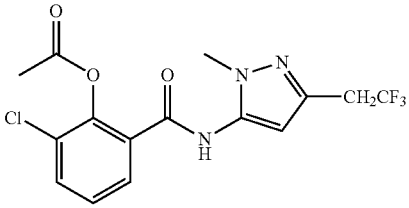 |
| 230 | 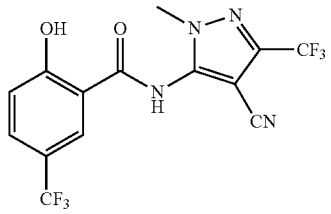 |
| 231 | 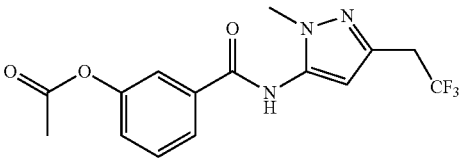 |
| 232 | 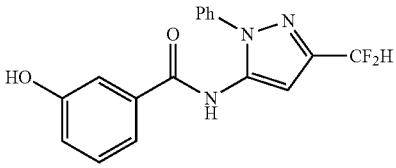 |
| 233 | 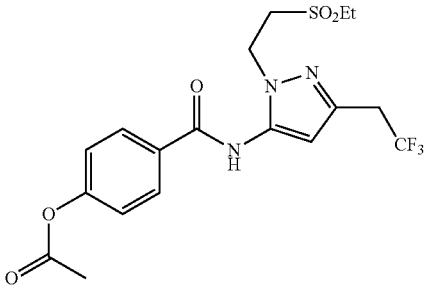 |
| 234 | 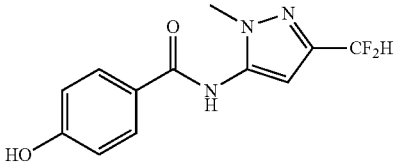 |
TABLE 1-continued
| No. | Structure |
|---|---|
| 235 | 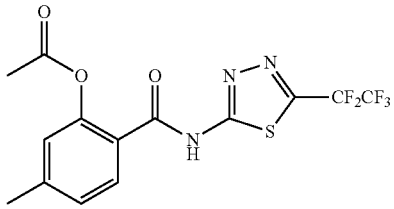 |
| 236 | 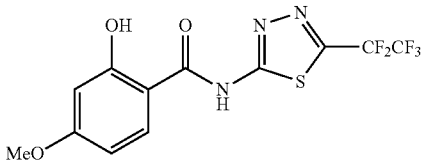 |
| 237 | 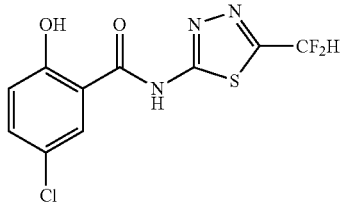 |
| 238 | 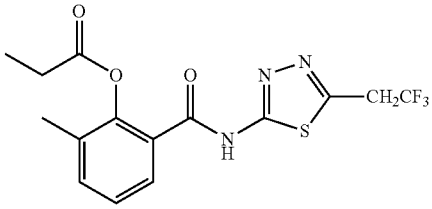 |
| 239 | 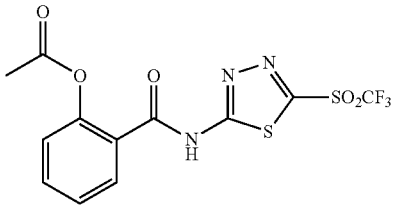 |
| 240 | 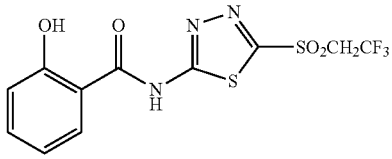 |
| 241 | 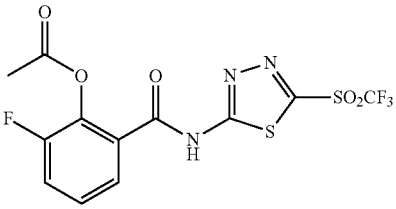 |

TABLE 1-continued
| No. | Structure |
|---|---|
| 242 | 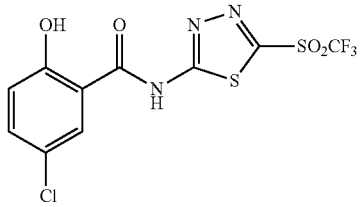 |
| 243 | 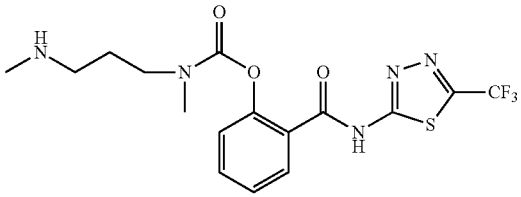 |
| 244 | 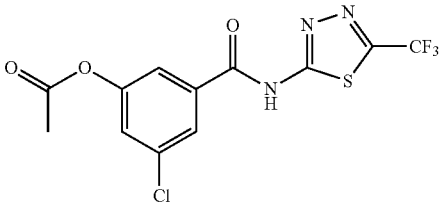 |
| 245 | 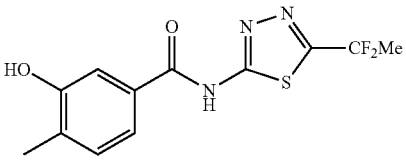 |
| 246 | 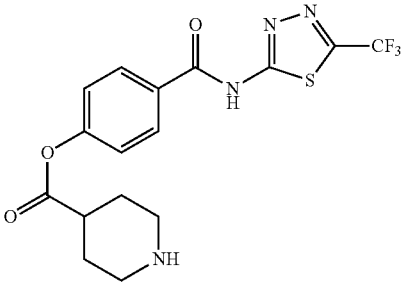 |
| 247 | 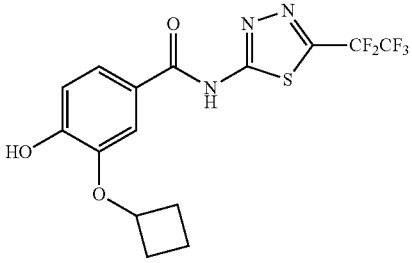 |
| 248 | 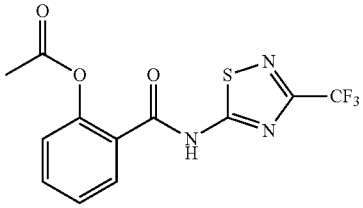 |
TABLE 1-continued
| No. | Structure |
|---|---|
| 249 | 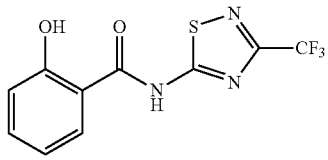 |
| 250 | 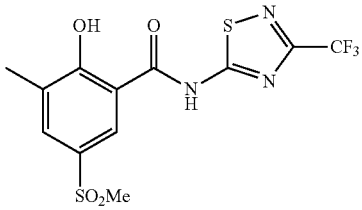 |
| 251 | 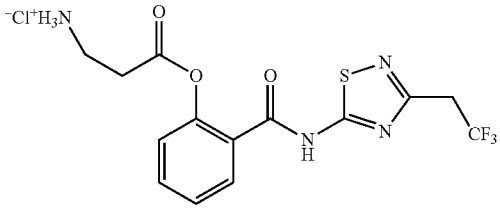 |
| 252 | 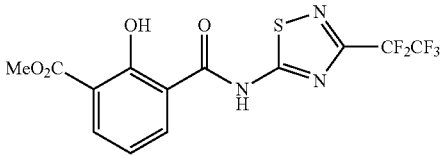 |
| 253 | 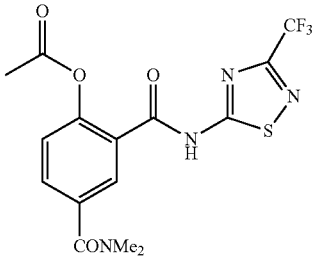 |
| 254 | 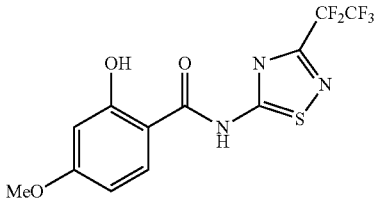 |
| 255 | 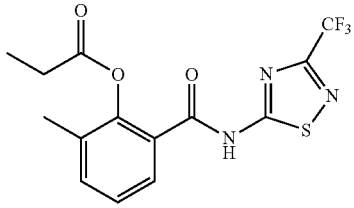 |

TABLE 1-continued
| No. | Structure |
|---|---|
| 256 | 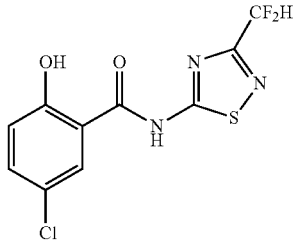 |
| 257 | 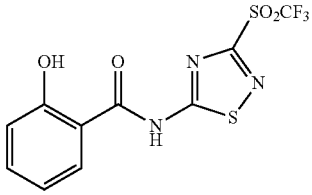 |
| 258 | 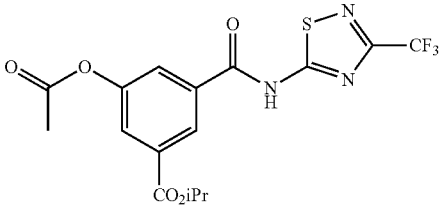 |
| 259 | 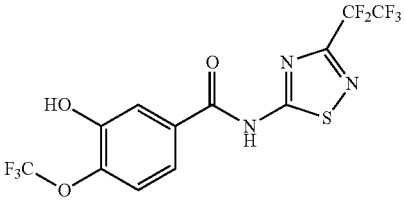 |
| 260 | 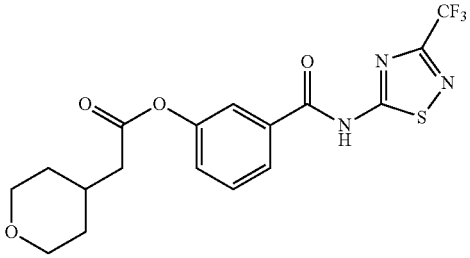 |
| 261 | 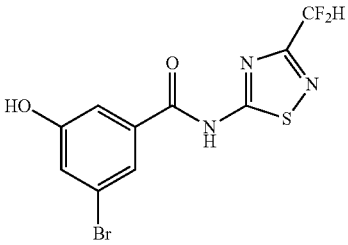 |
| 262 | 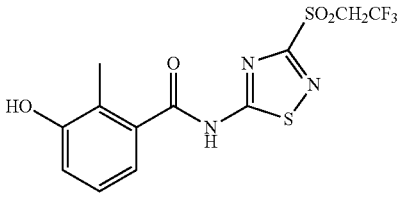 |
TABLE 1-continued
| No. | Structure |
|---|---|
| 263 | 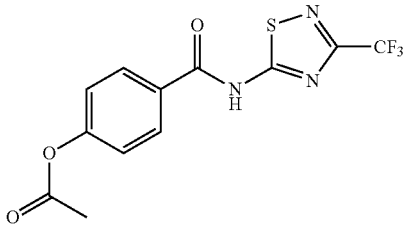 |
| 264 | 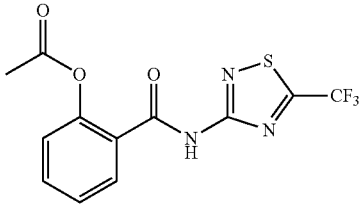 |
| 265 | 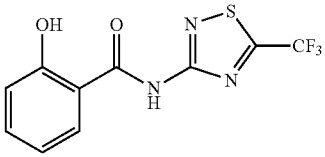 |
| 266 | 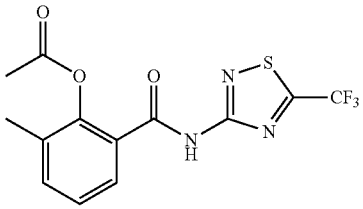 |
| 267 | 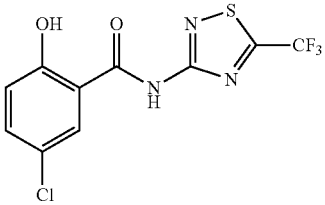 |
| 268 | 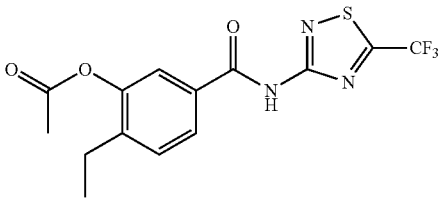 |
| 269 | 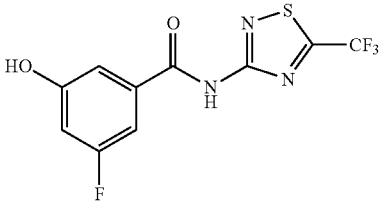 |

TABLE 1-continued
| No. | Structure |
|---|---|
| 270 | 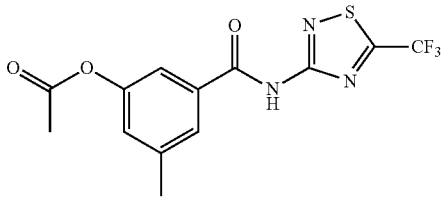 |
| 271 | 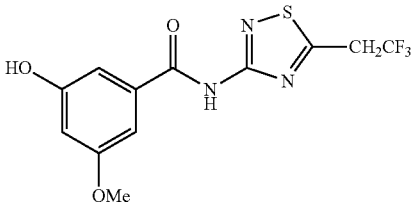 |
| 272 | 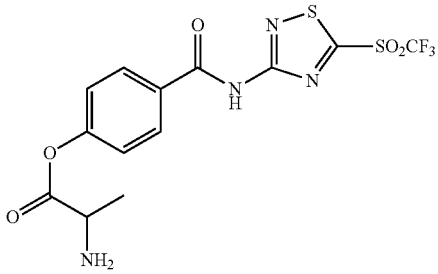 |
| 273 | 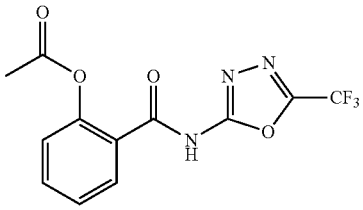 |
| 274 | 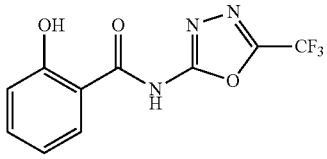 |
| 275 | 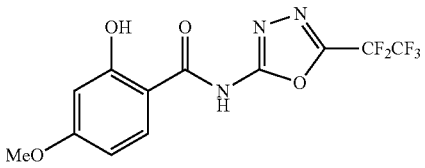 |
| 276 | 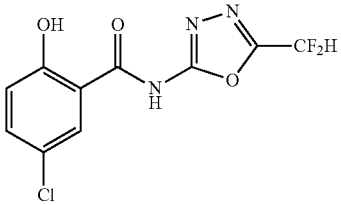 |
TABLE 1-continued
| No. | Structure |
|---|---|
| 277 | 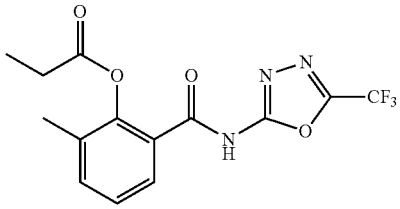 |
| 278 | 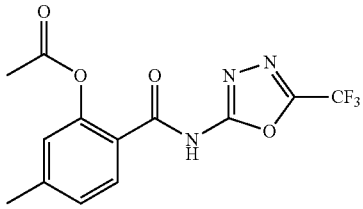 |
| 279 | 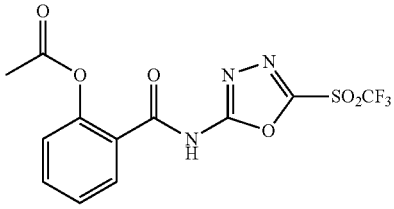 |
| 280 | 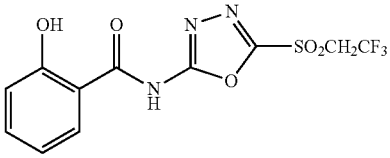 |
| 281 | 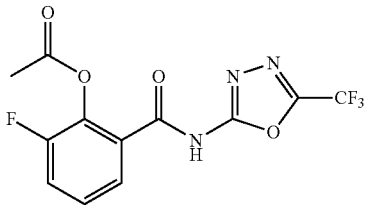 |
| 282 | 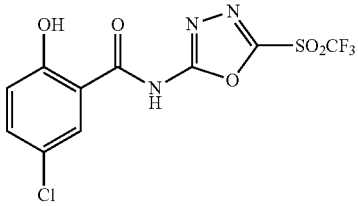 |
| 283 | 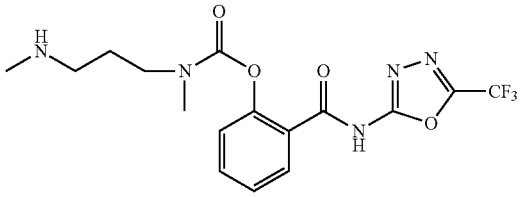 |

TABLE 1-continued
| No. | Structure |
|---|---|
| 284 | 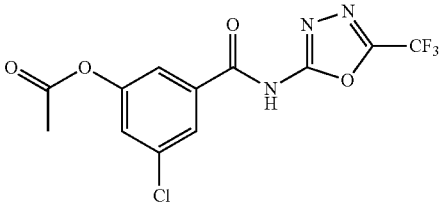 |
| 285 | 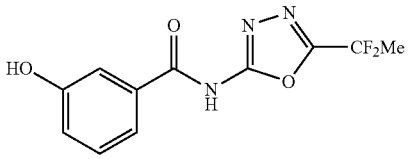 |
| 286 | 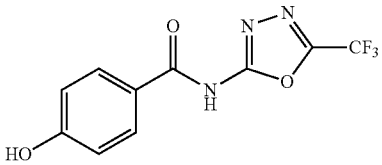 |
| 287 | 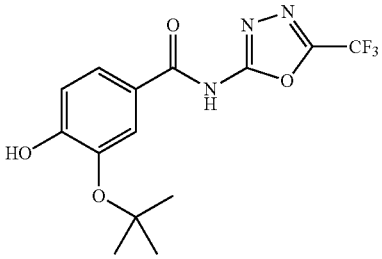 |
| 288 | 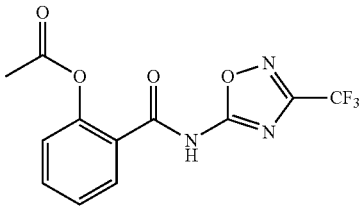 |
| 289 | 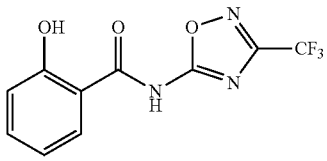 |
| 290 | 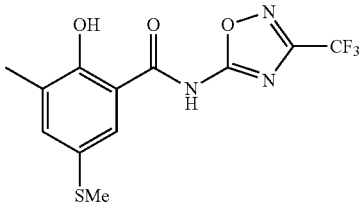 |
TABLE 1-continued
| No. | Structure |
|---|---|
| 291 | 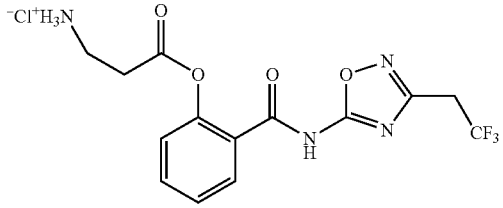 |
| 292 | 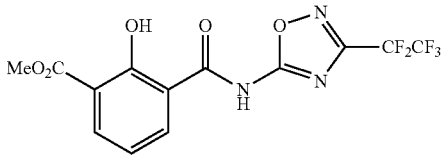 |
| 293 | 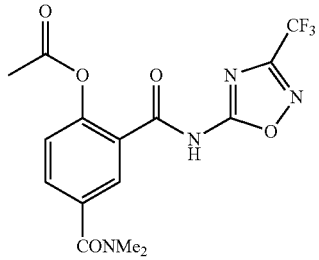 |
| 294 | 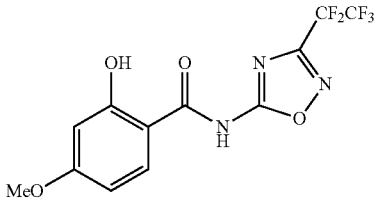 |
| 295 | 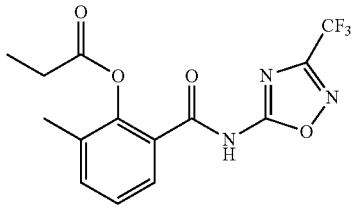 |
| 296 | 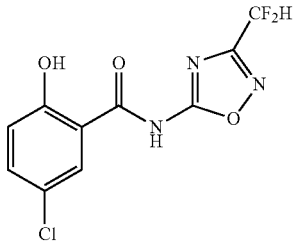 |
| 297 | 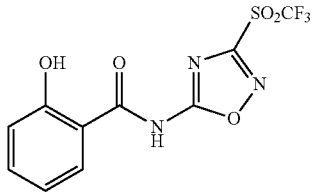 |

TABLE 1-continued
| No. | Structure |
|---|---|
| 298 | 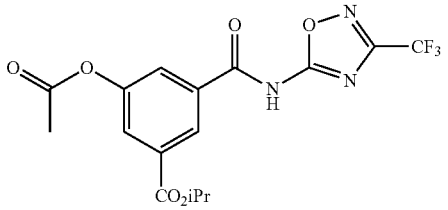 |
| 299 | 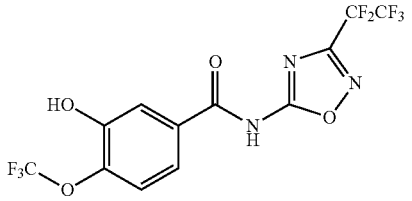 |
| 300 | 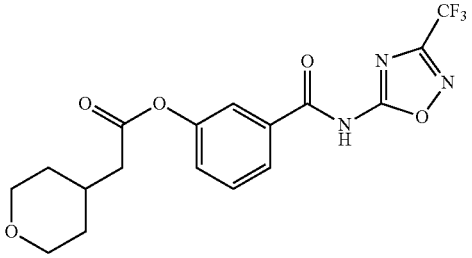 |
| 301 | 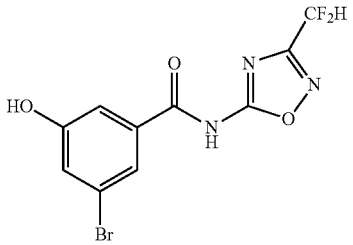 |
| 302 | 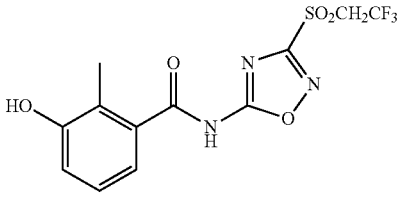 |
| 303 | 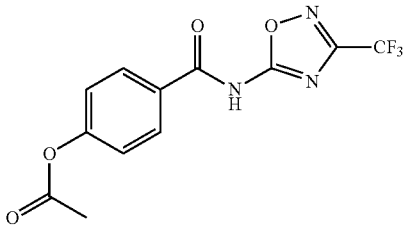 |
| 304 | 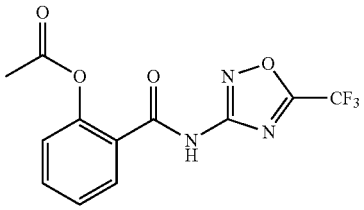 |
TABLE 1-continued
| No. | Structure |
|---|---|
| 305 | 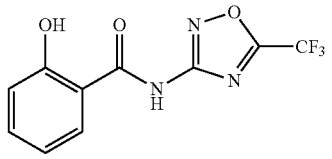 |
| 306 | 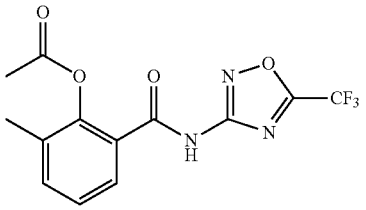 |
| 307 | 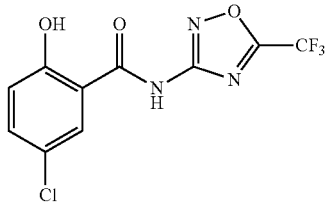 |
| 308 | 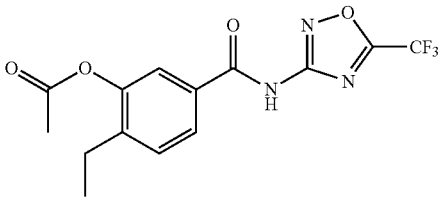 |
| 309 | 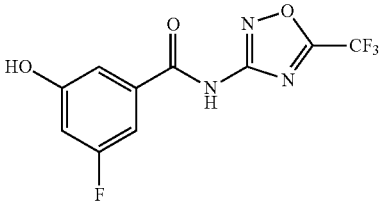 |
| 310 | 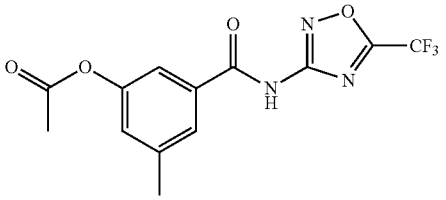 |
| 311 | 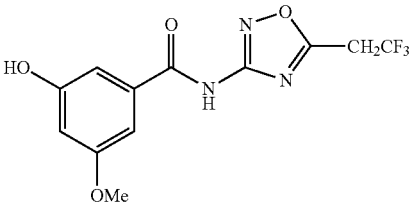 |

TABLE 1-continued
| No. | Structure |
|---|---|
| 312 | 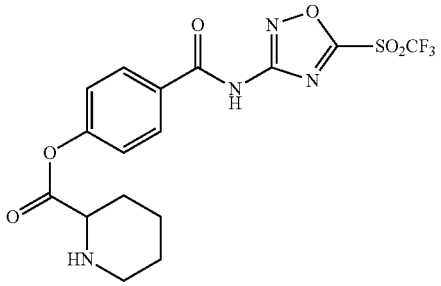 |
| 313 | 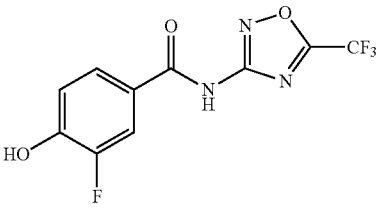 |
| 314 | 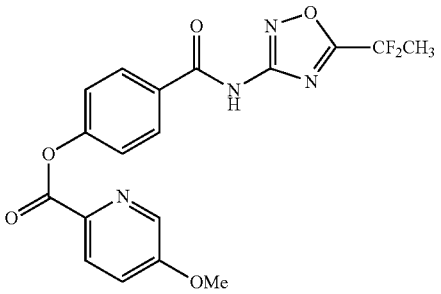 |
| 315 | 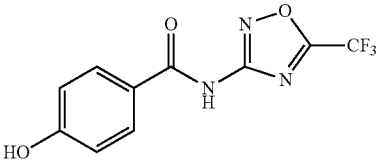 |
| 316 | 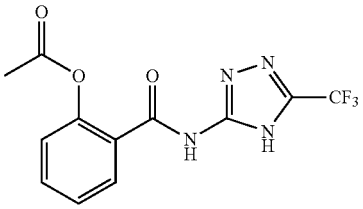 |
| 317 | 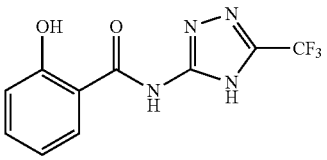 |
| 318 | 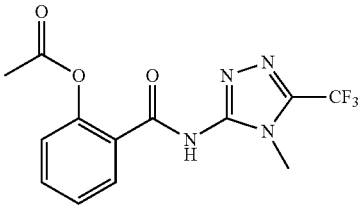 |
TABLE 1-continued
| No. | Structure |
|---|---|
| 319 | 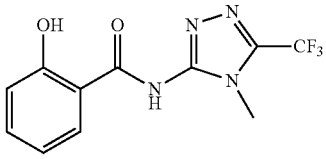 |
| 320 | 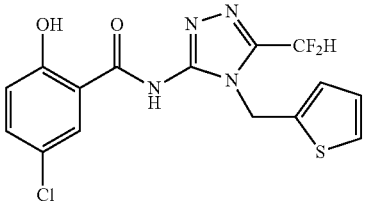 |
| 321 | 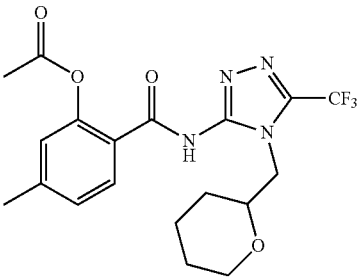 |
| 322 | 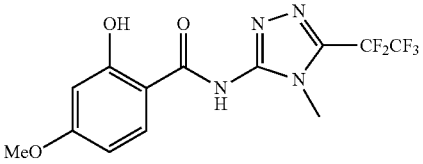 |
| 323 | 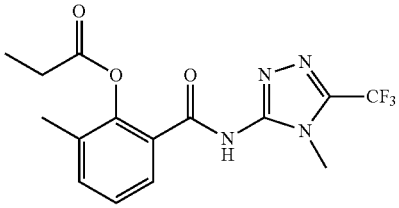 |
| 324 | 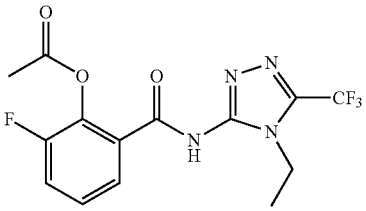 |
| 325 | 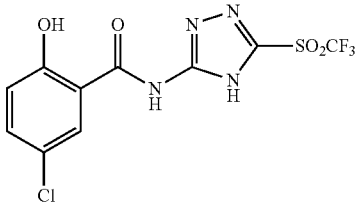 |

TABLE 1-continued
| No. | Structure |
|---|---|
| 326 | 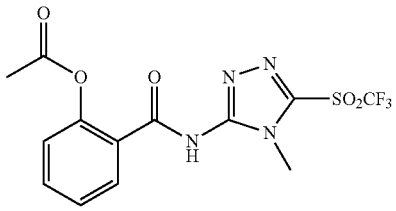 |
| 327 | 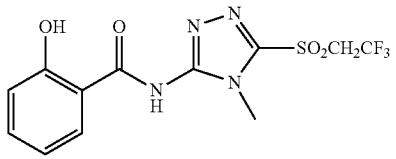 |
| 328 | 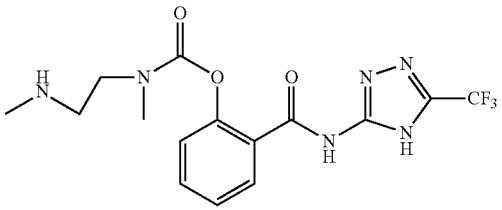 |
| 329 | 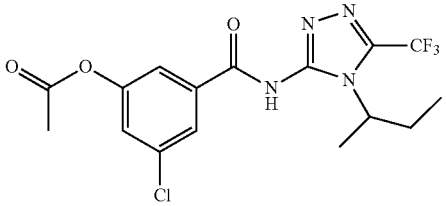 |
| 330 | 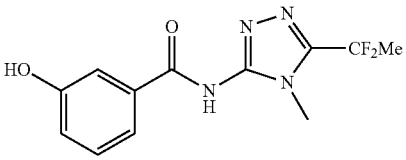 |
| 331 | 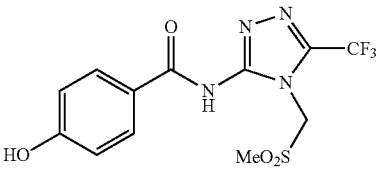 |
| 332 | 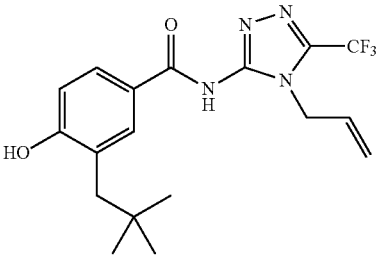 |
TABLE 1-continued
| No. | Structure |
|---|---|
| 333 | 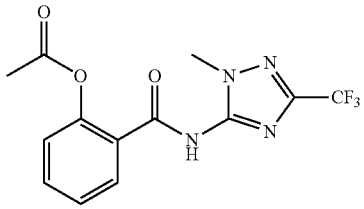 |
| 334 | 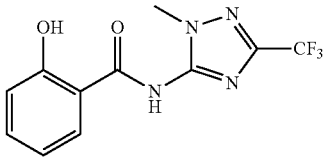 |
| 335 | 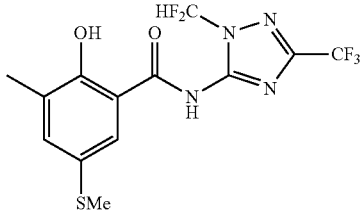 |
| 336 | 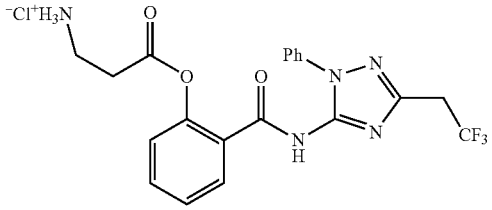 |
| 337 | 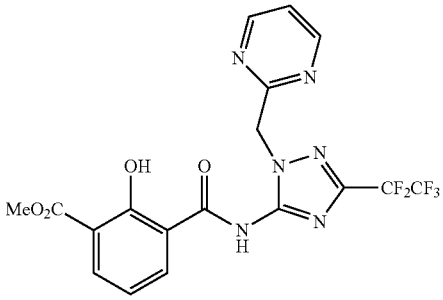 |
| 338 | 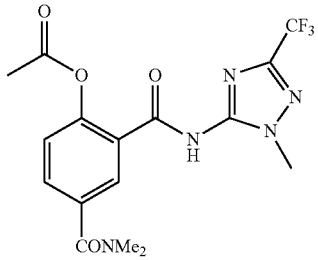 |

TABLE 1-continued
| No. | Structure |
|---|---|
| 339 | 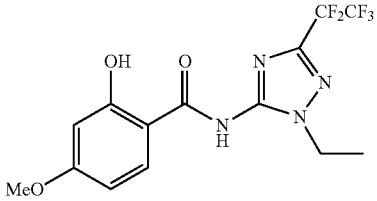 |
| 340 | 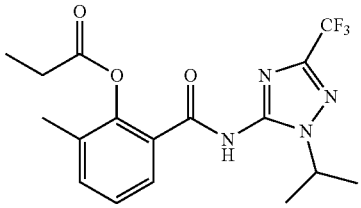 |
| 341 | 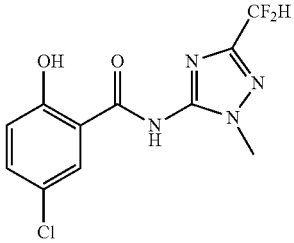 |
| 342 | 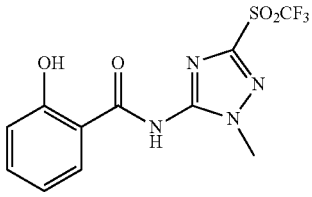 |
| 343 | 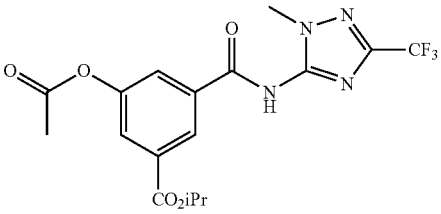 |
| 344 | 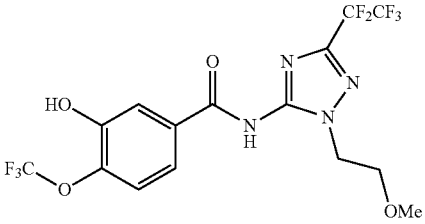 |
| 345 | 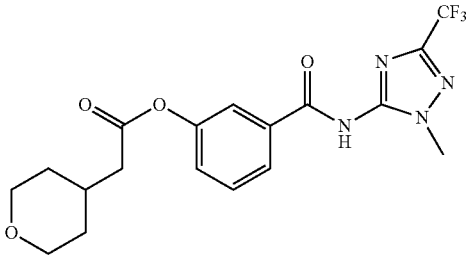 |
TABLE 1-continued
| No. | Structure |
|---|---|
| 346 | 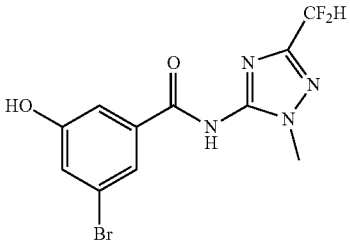 |
| 347 | 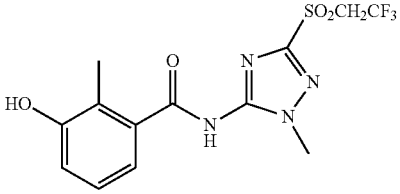 |
| 348 | 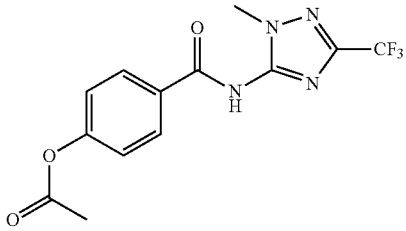 |
| 349 | 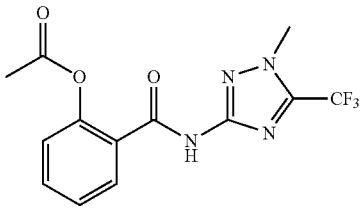 |
| 350 | 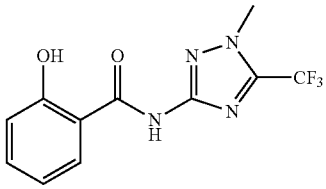 |
| 351 | 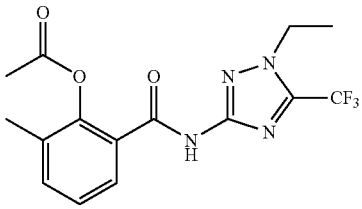 |

TABLE 1-continued
| No. | Structure |
|---|---|
| 352 | 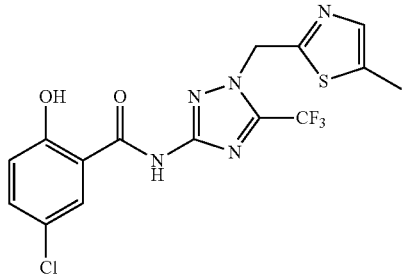 |
| 353 | 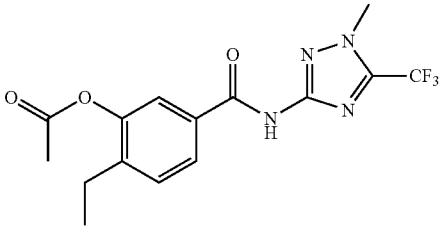 |
| 354 | 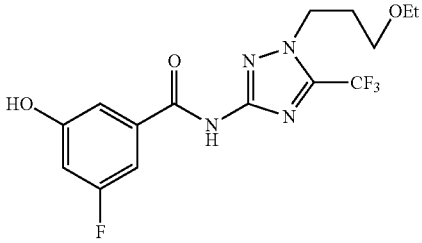 |
| 355 | 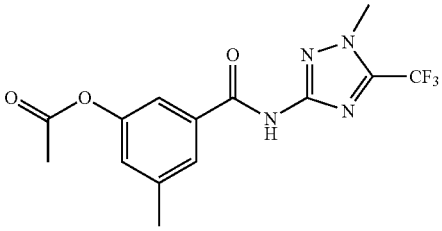 |
| 356 | 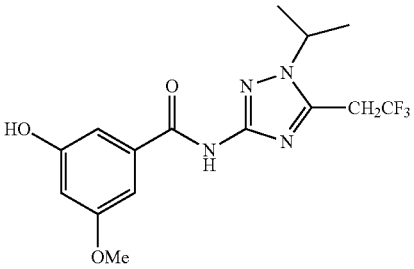 |
| 357 | 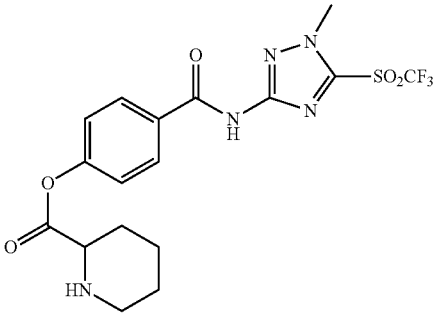 |
TABLE 1-continued
| No. | Structure |
|---|---|
| 358 | 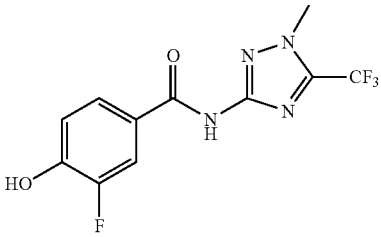 |
| 359 | 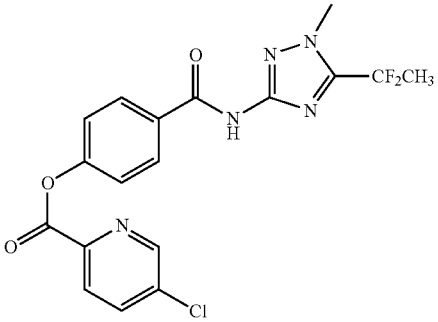 |
| 360 | 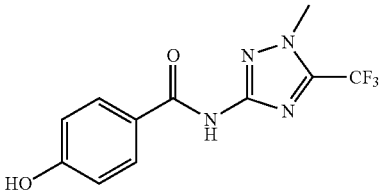 |
Table 2 designates the melting points of various compounds.
TABLE 2
| No. | Structure | Melting Point (° C.) |
|---|---|---|
| 1 | 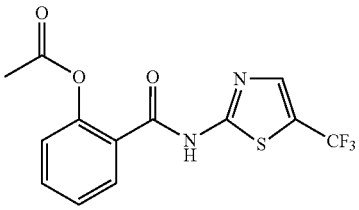 | 127.5-129.0 |
| 2 | 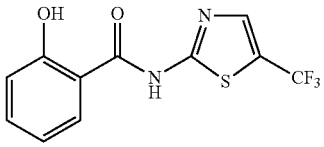 | 260-264 (dec) |
| 3 | 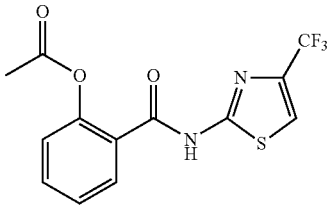 | 126-128 |

TABLE 2-continued

| No. | Structure | Melting Point (° C.) |
|---|---|---|
| 4 | 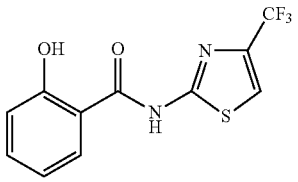 | 254-257 |
| 5 | 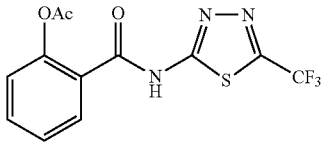 | 172-174 |
| 6 | 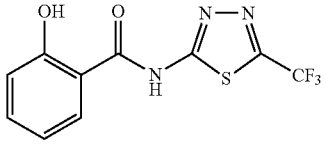 | >300 |

For the above compounds that have a trifluoromethyl group (—$CF_3$), it is also envisioned by the inventors that in place of the trifluoromethyl, a moiety selected from —$CF_2H$, —$CH_2CF_3$, —$CF_2CH_3$, —$CF_2CF_3$, —$SCF_3$, —$SO_2CF_3$, —$OCF_3$ and —$CH_2CH_2CF_3$ may be used.

Compounds of Formula (I), where $R_6$ is any of haloalkyl, perhaloalkyl, haloalkoxy, perhaloalkoxy, $S(O)_mC(R_7R_8)_nCF_3$, and $C(R_7R_8)_nCF_3$, may be synthesized by reacting an aroyl derivative, wherein $G_1$ is hydroxy, chloro, fluoro, bromo, alkoxy and the like with a heteroaromatic amine as shown below, wherein W, X, and Y are as defined above, under suitable reaction conditions. In some embodiments, the reaction may be generically represented as follows:

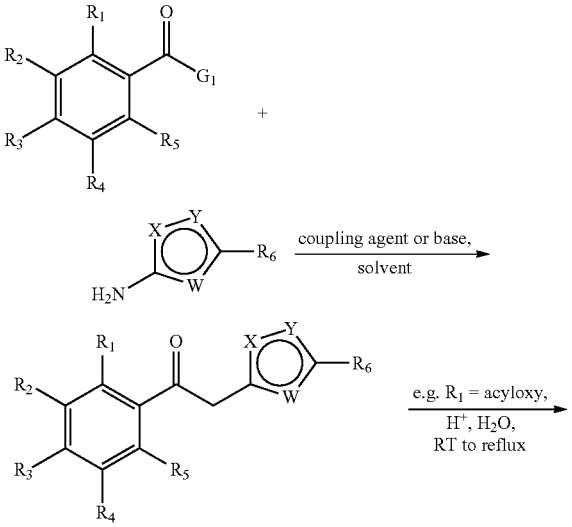

-continued

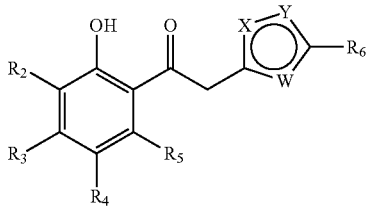

(I, $R_1$ = OH)

Examples of the invention, compounds (1) and (2), may be synthesized by the method described in the following reaction scheme. 2-Amino-5-trifluoromethyl-thiazole was prepared by a modification of the procedure of Laduron et al. J. Fluorine Chem. 1995, 73, 83-86. Coupling of o-acetylsalicyloyl chloride and 2-Amino-5-trifluoromethylthiazole in the presence of a suitable base, including tertiary amines like triethylamine, in a suitable inert solvent like dichloromethane, at about 0° C. to about ambient room temperature, affords compound (1). Hydrolysis of the acetyl moiety of compound (1) with dilute hydrochoric acid at room temperature to about 50° C. yields compound (2).

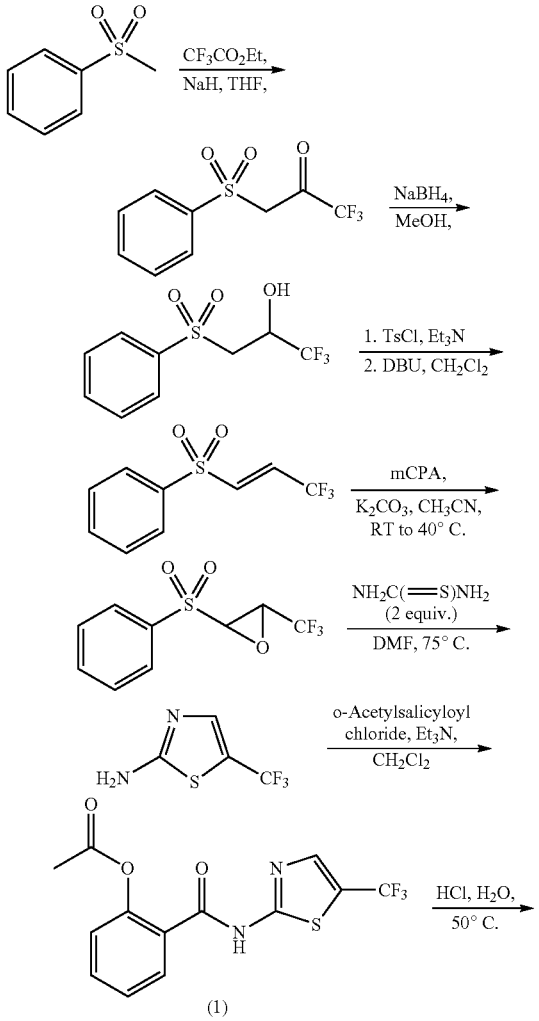

(1)

-continued

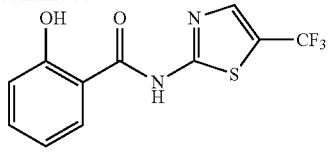

(2)

Further examples of the invention, compounds (3) and (4), may be synthesized via the synthetic pathway outlined in the scheme below, using commercially available 2-amino-4-trifluoromethylthiazole as a starting material.

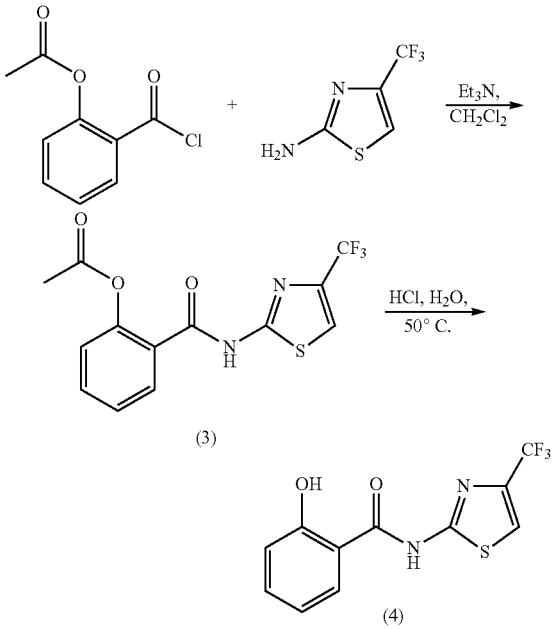

The compositions of the present invention may be formulated as solid or liquid dosage forms, or as pastes or ointments, and may optionally contain further active ingredients.

A pharmaceutical composition of the present invention comprises a pharmaceutically acceptable carrier, which is not particularly limited, and includes a wide range of carriers known to those of ordinary skill in the art, and including wetting or dispersing agents, starch derivatives, excipients, and the like. Tablet embodiments may optionally comprise a coating of a substance that constitutes an enteric coating, i.e., a coating that substantially insoluble in gastric secretion but substantially soluble in intestinal fluids.

Pharmaceutical compositions comprising the compounds of the present invention are in some embodiments formulated for oral administration and are optionally in the form of a liquid, for example an emulsion or a solution or a suspension in water or oil such as arachis oil, or other liquid. Formulations of non-aqueous micellar solutions may be prepared according to the method disclosed in U.S. Pat. No. 5,169,846. Alternatively, tablets can be manufactured, for example, by performing the following steps: wet granulation; drying; and compression. Film coating may generally be performed with organic solvents.

The present invention is a method, comprising administering to a subject at least one compound of the present invention in an amount in an effective amount for treating HCV infection (e.g., chronic HCV infection). In some embodiments, the method, comprising administering to a subject at least one pharmaceutical composition which comprises at least one compound of the present invention in an amount in an effective amount for treating HCV infection (e.g., chronic HCV infection).

In some embodiments, the subject is chosen from animals. In some embodiments, the subject is chosen from mammals. In some embodiments, the subject is chosen from pets, such as mice, dogs, cats, etc. In some embodiments, the subject is chosen from humans.

In some embodiments, the invention provides a method of treating a viral infection in a subject, comprising administering to the subject at least one dose of an effective amount of at least one compound of the present invention. In some embodiments, the invention provides a method of treating a viral infection in a subject, comprising administering to the subject at least one dose of an effective amount of at least one pharmaceutical composition comprising, in a pharmaceutically acceptable carrier, at least one compound of the present invention.

In some embodiments the antiviral treatment or prophylactic dosages of the compound of the present invention may depend upon the weight of the subject, and may be inferred by one of ordinary skill without undue experimentation by reference to the following examples, which are set forth for purposes of illustration and are not intended to be limiting.

The inventive compounds and compositions may be administered locally or systemically by any means known to an ordinarily skilled artisan. For example, the inventive compounds and compositions may be administered orally, parenterally, by inhalation spray, topically, rectally, nasally, buccally, vaginally or via an implanted reservoir in dosage formulations containing conventional non-toxic pharmaceutically acceptable carriers, adjuvants and vehicles. The term parenteral as used herein includes subcutaneous, intravenous, intraarterial, intramuscular, intraperitoneal, intrathecal, intraventricular, intrasternal, intracranial or intraosseous injection and infusion techniques. The exact administration protocol will vary depending upon various factors including the age, body weight, general health, sex and diet of the patient; the determination of specific administration procedures would be routine to an ordinarily skilled artisan.

Dose levels on the order of about 0.1 to about 100 mg/kg of the active ingredient compound are useful in the treatment of the above conditions (e.g., 0.1 mg/kg-day). In some embodiments, the amounts range from about 1 to about 10 mg/kg, and in other embodiments, the amounts range from about 2 to about 5 mg/kg. The specific dose level for any particular patient will vary depending upon a variety of factors, including the activity and the possible toxicity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

Any administration regimen for regulating the timing and sequence of drug delivery can be used and repeated as necessary to effect treatment. Such regimen may include multiple uses or preadministration and/or co-administration and/or postadministration with food, liquid, or water.

As noted above, this invention provides or contemplates a kit, comprising at least one compound of the invention. The kit could take any form. By way of example, a kit includes one or more containers for storing a pharmaceutical composition. In some embodiments, a container contains written instructions for administering the pharmaceutical composition. In some embodiments, a container contains is the substrate for the written instructions for administering the pharmaceutical composition. In some embodiments, the written instructions for administering the pharmaceutical composition are affixed to a container, for example, as in a container for filling a prescription sometimes has written instructions affixed on a surface.

Other embodiments of the invention will be apparent to those skilled in the art from consideration of the specification and practice of the invention disclosed herein. It is intended that the specification and its examples be considered as exemplary only, with a true scope and spirit of the invention being indicated by what may eventually be claimed.

EXAMPLES

1. Materials and Methods 1.1 Materials.

All test compounds were provided by Romark Laboratories, Nitazoxanide and Tizoxanide were used as standards.

1.2. HBV studies.

1.2.1. Antiviral Assays.

HBV antiviral assays were conducted as previous described [Korba and Gerin, Antiviral Res. 19:55 (1992 Confluent cultures of 2.2.15 cells were maintained on 96-well flat-bottomed tissue culture plates (confluence in this culture system is required for active, high levels of HBV replication equivalent to that observed in chronically-infected individuals [Sells et al. J. Virol. 62, 2836-2844 (1988); Korba and Gerin (1992)]. Cultures were treated with nine consecutive daily doses of the test compounds. HBV DNA levels were assessed by quantitative blot hybridization 24 hr. after the last treatment. Cytotoxicity was assessed by uptake of neutral red dye 24 hr. following the last treatment.

1.2.3. Production of HBV Proteins.

Cultures of 2.2.15 cells were treated under standard procedures and semi-quantitative EIA-based analysis of HBV proteins was performed as previously described [Korba and Gerin, Antivir. Res. 28, 225-242 (1995)], except that HBeAg was analyzed ETI-EBK Plus®(DiaSorin, Inc., Stillwater, Minn. USA). Samples were diluted (2 to 10-fold) to bring levels into the dynamic response ranges of the EIA's. HBsAg, and HBeAg were analyzed from culture medium samples and HBcAg was analyzed from intracellular lysates. Intracellular HBV RNA was assessed by quantitative northern blot hybridization (Korba and Gerin, 1995).

1.3. HCV Studies.

Antiviral activity of test compounds was assessed in a 3-day assay using the stably-expressing HCV replicon cell line, AVA5 (sub-genomic CONI, genotype 1b) [Blight et al., Science 290, 1972-1974 (2000)] maintained as sub-confluent cultures on 96-well plates as previously described (Okuse et al., Antiviral Research 65, 23-34 (2005)]. Antiviral activity was determined by blot hybridization analysis of intracellular HCV RNA (normalized to the level of cellular B-actin RNA in each culture sample) and cytotoxicity was assessed by neutral red dye uptake after 3 days of treatment. Additional studies were performed using Huh7 cells containing another HCV replicon, H/FL-Neo, a genotype 1a full length construct [Blight et al., J. Virol. 77, 3181-3190 (2003)]. For studies involving human serum, standard culture medium (which contains 10% fetal bovine serum) and assay conditions were maintained.

1.4. Presentation of Results.

$EC_{50}$, $EC_{90}$ and $CC_{50}$ values (±standard deviations [S.D.]) were calculated by linear regression analysis using data combined from all treated cultures (Korba and Gerin, 1992; Okuse et al., 2005). $EC_{50}$ and $EC_{90}$ are drug concentrations at which a 2-fold, or a 10-fold depression of intracellular HBV DNA or HCV RNA (relative to the average levels in untreated cultures), respectively, was observed. $CC_{50}$ is the drug concentration at which a 2-fold lower level of neutral red dye uptake (relative to the average levels in untreated cultures) was observed. Selectivity index (S.I.) was calculated as $CC_{50}/EC_{90}$ for HBV assays and $CC_{50}/EC_{50}$ for HCV assays. $EC_{90}$ values were used for calculation of the S.I. in HBV assays since at least a 3-fold depression of HBV DNA levels is typically required to achieve statistical significance in this assay system (Korba and Gerin, 1992). For combination treatments, $EC_{50}$, $EC_{90}$, $CC_{50}$ and S.I. are presented for the first compound listed. The molar ratio of the compounds in each combination is also indicated.

2. Results

TABLE 3

HBV Extracellular Virion Assay Results.

| Compd # | | $CC_{50}$ (μM) | | $EC_{50}$ (VIR) (μM) | | $EC_{90}$ (VIR) (μM) | | SI (VIR) |
|---|---|---|---|---|---|---|---|---|
| Nitazoxanide (reference) | > | 100.0 | | A | | C | > | 121 |
| Tizoxanide (reference) | > | 100.0 | | A | | C | > | 172 |
| 1 | > | 100.0 | | D | | E | > | 11 |
| 2 | > | 100.0 | | D | | E | > | 11 |
| 3 | > | 100.0 | > | E | > | E | | |
| 4 | > | 100.0 | > | E | > | E | | |
| 5 | > | 100.0 | > | E | > | E | | |
| 6 | > | 100.0 | > | E | > | E | | |

Legend: A: 0.05-0.2; B: 0.2-0.8; C: 0.8-3.2; D: 3.2-4.0; E: >4.0

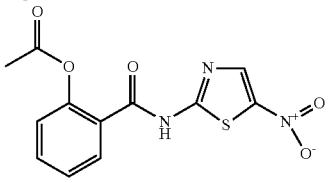

Nitazoxanide (reference)

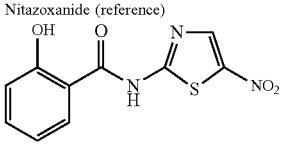

Tizoxanide (reference)

Table 4 presents data from the primary HCV replicon cell assay.

TABLE 4

Primary HCV Replicon Cell Assay.

| | PRIMARY ASSAY, GENOTYPE 1B | | | |
|---|---|---|---|---|
| Compound | CC50 (μM) | EC50 (μM) | EC90 (μM) | SI |
| Nitazoxanide (reference) | 32.0 | B | C | 169.0 |
| Tizoxanide (reference) | 15.0 | B | C | 100.0 |
| 1 | 3.7 | D | E | 0.9 |
| 2 | 0.46 | A | A | 58.0 |
| 3 | in | | test | |
| 4 | in | | test | |
| 5 | 15.0 | D | E | 15.0 |
| 6 | 5.3 | D | E | 1.4 |

EC50 & EC90 Legand

A: 0.005-0.05; B: 0.05-0.5; C: 0.5-10; D: 0-5.0; E: >5.0

TABLE 5

Antiviral Activity of Thiazolides Against Paramyxovirus, Influenza A and Coronavirus in Cell Assays

| | | Paramyxovirus (Sendai virus)-37RC cells | | | | Influenza A (PR8)-MDCK cells | | | | Coronavirus (CCoV)-A72 cells | | | |
|---|---|---|---|---|---|---|---|---|---|---|---|---|---|
| | | Virus Yield | | Toxicity $LD_{50}$ | S.I. | Virus Yield | | Toxicity $LD_{50}$ | S.I. | Virus Yield | | Toxicity $LD_{50}$ | S.I. |
| Compound | RM# | $ID_{50}$ µg/ml | $ID_{90}$ µg/ml | (MTT) µg/ml | $LD_{50}/ID_{50}$ | $ID_{50}$ µg/ml | $ID_{90}$ µg/ml | (MTT) µg/ml | $LD_{50}/ID_{50}$ | $ID_{50}$ µg/ml | $ID_{90}$ µg/ml | (MTT) µg/ml | $LD_{50}/ID_{50}$ |
| Nitazoxanide (reference) | NTZ | 1 | 6 | >50 | >50 | 1 | 7 | >50 | >50 | | | | |
| Tizoxanide (reference) | TIZ | 0.5 | 5 | >50 | >100 | 1 | 9 | >50 | >50 | 1 | 1.5 | >50 | >50 |
| 1 | RM5036 | | | | | | | | | | | | |
| 2 | RM5037 | | | | | | | | | | | | |
| 3 | RM5034 | | | | | | | | | | | | |
| 4 | RM5035 | | | | | | | | | | | | |
| 5 | RM4816 | 3 | 9 | >50 | >17 | 3 | 9 | >50 | >16.7 | | | | |
| 6 | RM5033 | | | | | | | | | | | | |

TABLE 6

Antiviral Activity of Thiazolides Against Rhinovirus, Respiratory Syncytial Virus and Herpesvirus in Cell Assays

| | | Rhinovirus (RHV-2) HeLa R19 cells | | | | Respiratory Syncytial Virus (RV-A2)-HeLa cells | | | | | Herpesvirus (HSV-1)-Hep-2 cells | | |
|---|---|---|---|---|---|---|---|---|---|---|---|---|---|
| | | Virus Yield | | Toxicity $LD_{50}$ | S.I. | Virus Yield | | Toxicity $LD_{50}$ | | S.I. | Virus Yield | Toxicity $LD_{50}$ | S.I. |
| Compound | RM# | $ID_{50}$ µg/ml | $ID_{90}$ µg/ml | (MTT) µg/ml | $LD_{50}/ID_{50}$ | $ID_{50}$ µg/ml | $ID_{90}$ µg/ml | (MTT) µg/ml | $LD_{50}/ID_{50}$ | $ID_{50}$ µg/ml | $ID_{90}$ µg/ml | (MTT) µg/ml | $LD_{50}/ID_{50}$ |
| Nitazoxanide (reference) | NTZ | 2.5 | >50 | >50 | >20 | | | | | 0.025 | 0.5 | >50 | >2000 |
| Tizoxanide (reference) | TIZ | 0.3 | 40 | >50 | >167 | 0.5 | — | 3 | 6 | 2 | 5 | 50 | 25 |
| 1 | RM5036 | 9 | >50 | >50 | >5.5 | | | | | 0.2 | 2 | >50 | >250 |
| 2 | RM5037 | | | | | | | | | | | | |
| 3 | RM5034 | | | | | | | | | 0.03 | 1.5 | >50 | >1667 |
| 4 | RM5035 | | | | | | | | | 0.15 | 1.5 | >50 | >333 |
| 5 | RM4816 | | | | | | | | | | | | |
| 6 | RM5033 | | | | | | | | | 0.2 | 1 | >50 | >250 |

TABLE 7

Antiviral Activity of Thiazolides Against Rotavirus (2 strains) and Adenovirus in Cell Assays

| | | Rotavirus (Simian SA11)-MA104 cells | | | | Rotavirus (WAG8P1)-MA104 cells | | | | Adenovirus (Ad5)-HeLa R19 cells | | | |
|---|---|---|---|---|---|---|---|---|---|---|---|---|---|
| | | Virus Yield | | Toxicity $LD_{50}$ | S.I. | Virus Yield | | Toxicity $LD_{50}$ | S.I. | Virus Yield | | Toxicity $LD_{50}$ | S.I. |
| Compound | RM# | $ID_{50}$ µg/ml | $ID_{90}$ µg/ml | (MTT) µg/ml | $LD_{50}/ID_{50}$ | $ID_{50}$ µg/ml | $ID_{90}$ µg/ml | (MTT) µg/ml | $LD_{50}/ID_{50}$ | $ID_{50}$ µg/ml | $ID_{90}$ µg/ml | (MTT) µg/ml | $LD_{50}/ID_{50}$ |
| Nitazoxanide (reference) | NTZ | 1 | 10 | >50 | >50 | 10 | 40 | >50 | >5 | 1.5 | 15 | >50 | >33.3 |
| Tizoxanide (reference) | TIZ | 0.5 | 4 | >50 | >100 | 1 | 15 | >50 | >50 | 0.2 | 0.3 | 0.8 | 5 |
| 1 | RM5036 | | | | | | | | | 0.1 | 3.5 | 4 | 40 |
| 2 | RM5037 | | | | | | | | | | | | |
| 3 | RM5034 | | | | | | | | | | | | |
| 4 | RM5035 | | | | | | | | | | | | |
| 5 | RM4816 | | | | | | | | | | | | |
| 6 | RM5033 | | | | | | | | | | | | |

TABLE 8

Antiviral Activity of thiazolides Against Rhabdovirus in Cell Assays

| | | Rhabdovirus (VSV)-MA104 cells | | | |
|---|---|---|---|---|---|
| | | Virus Yield | | Toxicity $LD_{50}$ | |
| Compound | RM # | $ID_{50}$ μg/ml | $ID_{90}$ μg/ml | (MTT) μg/ml | S.I. $LD_{50}/ID_{50}$ |
| Nitazoxanide (reference) | NTZ | | | | |
| Tizoxanide (reference) | TIZ | 2 | 15 | 50 | 25 |
| 1 | RM5036 | | | | |
| 2 | RM5037 | | | | |
| 3 | RM5034 | | | | |
| 4 | RM5035 | | | | |
| 5 | RM4816 | | | | |
| 6 | RM5033 | | | | |

The invention claimed is:

1. A pharmaceutical composition comprising a compound of Formula I:

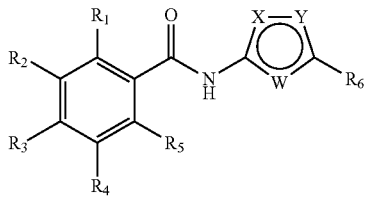

(I)

wherein:

$R_1$ through $R_5$ and $R_{10}$ are, independently, hydrogen, CN, $NO_2$, F, Cl, Br, I, hydroxy, alkyl, alkenyl, alkynyl, cycloalkyl, cycloalkylalkyl, cycloalkylalkenyl, cycloalkylalkynyl, cycloalkenyl, cycloalkenylalkyl, cycloalkenylalkenyl, cycloalkenylalkynyl, alkoxy, alkenyloxy, alkynyloxy, alkoxyalkyl, alkoxyalkenyl, alkoxyalkynyl, alkenyloxyalkyl, alkenyloxyalkenyl, alkenyloxyalkynyl, alkynyloxyalkyl, alkenyloxyalkenyl, alkenyloxyalkynyl, cycloalkoxy, cycloalkylalkoxy, cycloalkylalkenyloxy, cycloalkylalkynyloxy, cycloalkenyloxy, cycloalkenylalkoxy, cycloalkenylalkenyloxy, cycloalkenylalkynyloxy, alkoxyalkylamino, hydroxyalkyl, acyl, acyloxy, aroyloxy, arylalkanoyloxy, arylalkenoyloxy, heteroaroyloxy, heteroarylalkanoyloxy, heteroarylalkenoyloxy, alkoxycarbonyl, aryloxycarbonyl, arylalkoxycarbonyl, heteroaryloxycarbonyl, heteroarylalkoxycarbonyl, alkoxycarbonyloxy, carbamoyl, carbamoyloxy, alkylamino, dialkylamino, alkylaminoalkyl, amido, alkylamido, dialkylamido, haloalkyl, perhaloalkyl, perhaloalkoxy, alkylthio, alkylthioalkyl, alkylsulfonyl, alkylsulfonylalkyl, alkenylsulfonyl, alkynylsulfonyl, cycloalkylsulfonyl, cycloalkylalkylsulfonyl, cycloalkylsulfonylalkyl, cycloalkylalkylsulfonylalkyl, arylsulfonyl, arylalkylsulfonyl, arylalkenylsulfonyl, heteroarylsulfonyl, heteroarylalkylsulfonyl, heteroarylalkenylsulfonyl, alkylsulfonamido, N,N'-dialkylsulfonamido, sulfonamidoalkyl, sulfonamidoaryl, sulfonamidoarylalkyl, sulfonamidoarylalkenyl, aryl, arylalkyl, aryloxy, arylalkoxy, arylthio, arylalkylthio, arylamino, arylalkylamino, arylalkenyl, arylalkynyl, heteroaryl, heteroarylalkyl, heteroarylalkenyl, heteroarylalkynyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, or heterocycloalkenyloxy, any of which may be optionally substituted wherein $R_6$ is selected from the group consisting of haloalkyl, perhaloalkyl, haloalkoxy, perhaloalkoxy, $S(O)_mC(R_7R_8)_nCF_3$, and $C(R_7R_8)_nCF_3$;

wherein W, X and Y are, independently, S, O, N, $NR_9$ or $CR_{10}$ where at least two of W, X, and Y are S, O, N, or $NR_9$;

wherein $R_7$, $R_8$, and $R_9$ are, independently, hydrogen, fluoro, chloro, alkyl, perhaloalkyl, aryl, arylalkyl, heteroaryl, or heteroarylalkyl, or together with the atoms to which they are attached, may be joined to form an optionally substituted 4-to 8-membered heterocycloalkyl or an optionally substituted 3- to 8-membered cycloalkyl ring, any of which may be optionally substituted;

m is an integer between 0 and 2; and n is an integer between 0 and 5;

or a pharmaceutically acceptable salt or ester thereof, and a pharmaceutically acceptable carrier, wherein the composition comprises an effective amount of the compound for treating a viral pathogen.

2. The pharmaceutical composition of claim 1, wherein the viral pathogen is Hepatitis B or Hepatitis C Virus infection.

3. The pharmaceutical composition of claim 1, wherein the viral pathogen is a parainfluenza, an influenza A, or an influenza B infection.

4. A method for treating a viral infection comprising administering the pharmaceutical composition of claim 1 to a patient in need thereof.

5. A method for treating a viral infection comprising administering the pharmaceutical composition as claimed in claim 1, to a patient in need thereof, in combination with another antiviral composition.

6. The method of claim 4, wherein the viral infection is selected from the group consisting of respiratory viruses, herpes viruses, and gastrointestinal viruses.

7. The method of claim 6, wherein said respiratory viral infection is selected from the group consisting of parainfluenza, influenza A, influenza B, coronavirus, rhinovirus (RHV), and respiratory syncytial virus (RSV).

8. The method of claim 6, wherein said gastrointestinal virus is selected from the group consisting of rotavirus and adenovirus.

9. A method for treating rhabdovirus comprising administering the pharmaceutical composition of claim 1 to a patient in need thereof.

10. The pharmaceutical composition of claim 1, wherein:

$R_1$ through $R_5$ and $R_{10}$ are, independently, hydrogen, cyano, nitro, halo, hydroxy. alkyl, alkenyl, alkynyl, alkoxy, alkenyloxy, alkynyloxy, acyl, acyloxy, aroyloxy, heteroaroyloxy, alkoxycarbonyl, aryloxycarbonyl, heteroaryloxycarbonyl, alkoxycarbonyloxy, carbamoyl, carbamoyloxy, alkylamino, haloalkyl, perhaloalkyl, perhaloalkoxy, alkylthio, perhaloalkylthio, alkylthioalkyl, alkylsulfonyl, alkylsulfonylalkyl, arylsulfonyl, heteroarylsulfonyl, alkylsulfonamido, sulfonamidoalkyl, aryl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heterocycloalkyl, and heterocycloalkoxy, all optionally substituted with substituents selected independently from carbonyl (oxo), carboxyl, lower alkyl carboxylate, lower alkyl carbonate, lower alkyl carbamate, halogen, hydroxy, amino, amido, cyano, hydrazinyl, hydrazinylcarbonyl, alkylhydrazinyl, dialkylhydrazinyl, arylhydrazinyl, heteroarylhydrazinyl, nitro, thiol, sulfonic acid, trisubstituted silyl, urea, acyl, acyloxy, acylamino, arylthio, lower alkyl, lower alkylamino, lower dialkylamino, lower alkyloxy, lower alkoxyalkyl, lower alkylthio, lower alkylsulfonyl, lower alkenyl, lower alkenylamino, lower dialkenylamino, lower alkenyloxy, lower alkenylthio, lower alkenyl sulfonyl, lower alkynyl, lower alkynylamino, lower dialkynylamino, lower alkynyloxy, lower alkynylthio, lower alkynylsulfonyl, lower cycioalkyl, lower cycioalkyloxy, lower cycioalkylamino, lower cycloalkylthio, lower cycioalkylsulfonyl, lower cycioalkylalkyl, lower cycioalkylalkyloxy, lower cycioalkylalkylamino, lower cycioalkylalkylthio, lower cycioalkylalkylsulfonyl, aryl, aryloxy, arylamino, arylthio, arylsulfonyl, arylalkyl, arylalkyloxy, arylalkylamino, arylalkylthio, arylalkylsulfonyl, heteroaryl, heteroaryloxy, heteroarylamino, heteroarylthio, heteroarylsulfonyl, heteroarylalkyl, heteroarylalkyloxy, heteroarylalkylamino, heteroarylalkylthio, heteroarylalkylsulfonyl, heterocycioalkyl, heterocycioalkyloxy, heterocycioalkylamino, heterocycioalkylthio, heterocycloalkylsulfonyl, lower haloalkyl, lower haloalkenyl, lower haloalkynyl, lower perhaloalkyl, lower perhaloalkoxy, lower haloalkoxy, and lower acyloxy;

$R_6$ is selected from the group consisting of haloalkyl, perhaloalkyl, haloalkoxy, perhaloalkoxy, $S(O)_mC(R_7R_8)_nCF_3$, and $C(R_7R_8)_nCF_3$;

wherein W, X and Y are independently chosen from the group consisting of S, O, N, $NR_9$ and $CR_{10}$ and at least two of W, X and Y are heteroatoms;

wherein $R_7$, $R_8$, and $R_9$ are independently selected from the group consisting of hydrogen, fluoro, chloro, alkyl, perhaloalkyl, aryl, arylalkyl, heteroaryl and heteroarylalkyl, or together with the atoms to which they are attached, may be joined to form an optionally substituted 4- to 8-membered heterocycioalkyl or an optionally substituted 3- to 8-membered cycioalkyl ring, any of which may be optionally substituted as for $R_1$ through $R_5$ and $R_{10}$;

m is an integer between 0 and 2; and n is an integer between 0 and 5.

11. The pharmaceutical composition of claim 1, wherein $R_1$ through $R_5$ are, independently, hydrogen, CN, F, Cl, Br, hydroxy, alkyl, alkoxy, hydroxyalkyl, acyloxy, aroyloxy, arylalkanoyloxy, arylalkenoyloxy, heteroaroyloxy, heteroarylalkanoyloxy, heteroarylalkenoyloxy, alkoxycarbonyloxy, carbamoyloxy, alkylamino, haloalkyl, perhaloalkyl, perhaloalkoxy, alkylthio, alkylthioalkyl, alkylsulfonyl, cycloalkylsulfonyl, or cycloalkylalkylsulfonyl, any of which may be optionally substituted with halogen, alkoxy, perhalo-$C_1$-$C_3$-alkyl, or $C_1$-$C_3$ alkyl;

$R_6$ is selected from the group consisting of perhaloalkyl, $S(O)_mC(R_7R_8)_nCF_3$, and $C(R_7R_8)_nCF_3$;

$R_7$, $R_8$, and $R_9$ are independently selected from the group consisting of hydrogen, fluoro, chloro, alkyl, and perhaloalkyl, any of which may be optionally substituted;

$R_{10}$ is selected from the group consisting of hydrogen, CN, $NO_2$, F, Cl, Br, alkyl, cycloalkyl, cycloalkylalkyl, alkoxy, alkoxyalkyl, cycloalkoxy, cycloalkylalkoxy, acyl, alkoxycarbonyl, aryloxycarbonyl, arylalkoxycarbonyl, heteroaryloxycarbonyl, heteroarylalkoxycarbonyl, carbamoyl, alkylamino, amido, alkylamido, dialkylamido, perhaloalkyl, alkylthio, alkylthioalkyl, alkylsulfonyl, alkylsulfonylalkyl, cycloalkylsulfonyl, alkylsulfonamido, aryl, arylalkyl, aryloxy, arylalkoxy, arylthio, arylalkylthio, arylamino, arylalkylamino, heteroaryl, heteroarylalkyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy; and n is an integer between 0 and 2.

12. The pharmaceutical composition of claim 11, wherein:

$R_1$, $R_2$, and $R_3$ are, independently, hydroxy, acyloxy, aroyloxy, arylalkanoyloxy, arylalkenoyloxy, heteroaroyloxy, heteroarylalkanoyloxy, heteroarylalkenoyloxy, alkoxycarbonyloxy, or carbamoyloxy, any of which may be optionally substituted;

$R_6$ is selected from the group consisting of perhaloalkyl and $C(R_7R_8)$—$CF_3$;

$R_7$ and $R_8$ are independently selected from the group consisting of hydrogen, fluoro, and chloro; and $R_{10}$ is selected from the group consisting of hydrogen, CN, $NO_2$, F, Cl, Br, alkyl, cycloalkyl, cycloalkoxy, acyl, alkoxycarbonyl, aryloxycarbonyl, heteroaryloxycarbonyl, carbamoyl, amido, dialkylamido, perhaloalkyl, alkylthio, alkylsulfonyl, alkylsulfonylalkyl, cycloalkylsulfonyl, aryl, arylalkyl, heteroaryl, heteroarylalkyl, heteroarylthio, heteroarylalkylthio, heterocycloalkyl, and heterocycloalkenyl.

13. The pharmaceutical composition of claim 12 comprising a compound of Formula II or III or V or VI or VII or VIII or IX or X or XI or XII or XIII or XVI or XVII or XVIII or XIX (II)

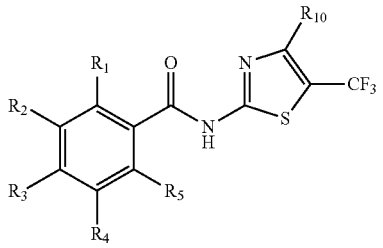

(III)

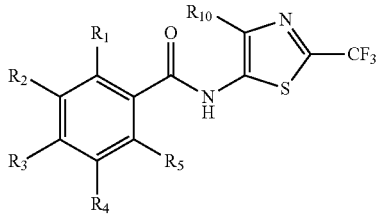

(V)

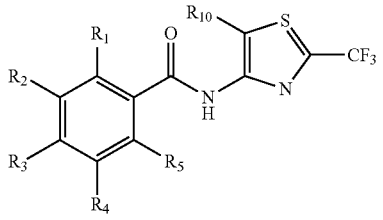

-continued
(XI)
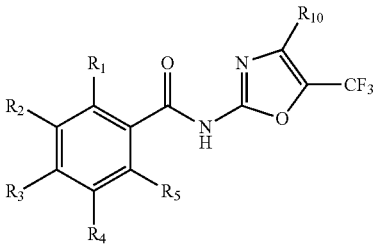
(VII)
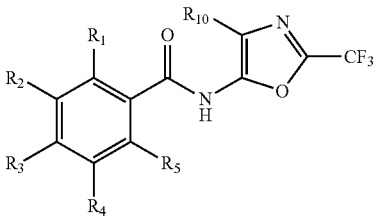
(VIII)
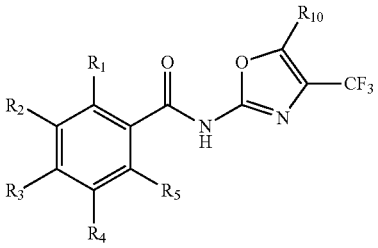
(IX)
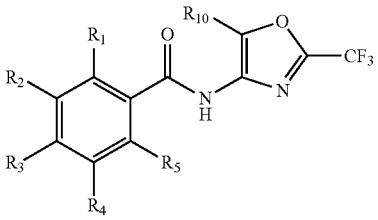
(X)
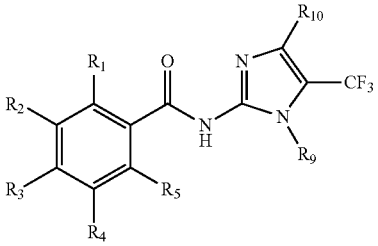
(XI)
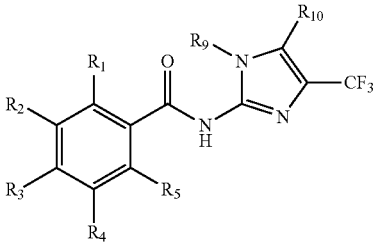
-continued
(XII)
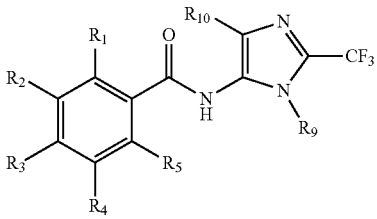
(XIII)
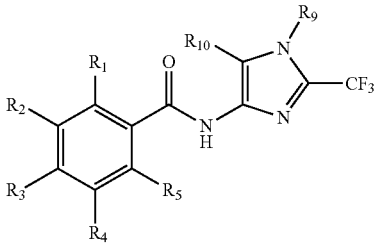
(XIV)
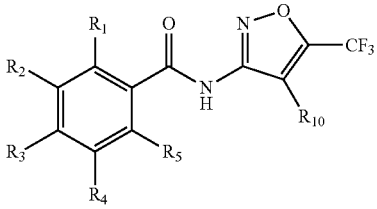
(XV)
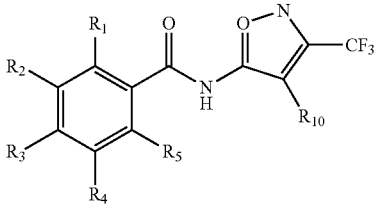
(XIV)
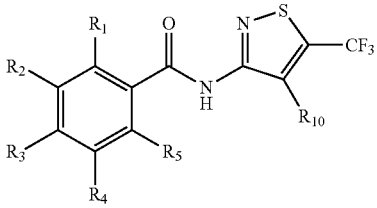
(XVII)
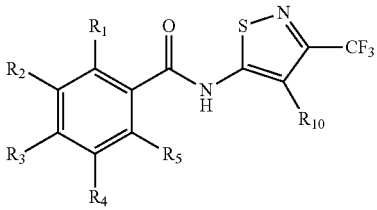
(XVIII)
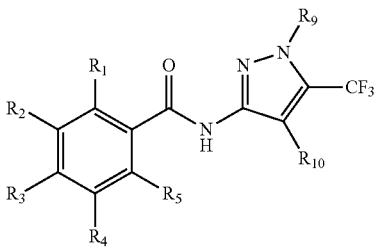

-continued (XIX)

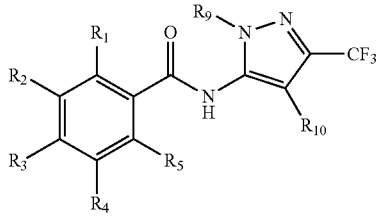

wherein:

$R_{10}$ is selected from the group consisting of hydrogen, CN, $NO_2$, F, Cl, Br, alkyl, cycloalkyl, acyl, alkoxycarbonyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl.

14. The pharmaceutical composition of claim 1, wherein the compound is of Formula IV (IV)

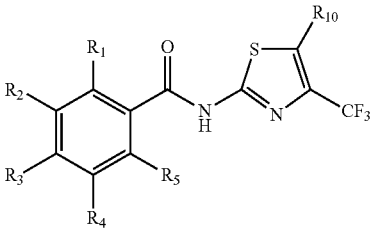

wherein:

$R_{10}$ is selected from the group consisting of hydrogen, CN, $NO_2$, F, Cl, alkyl, aryloxycarbonyl, heteroaryloxycarbonyl, carbamoyl, amido, dialkylamido, perhaloalkyl, alkylsulfonyl, alkylsulfonylalkyl, cycloalkylsulfonyl, aryl, arylalkyl, heteroaryl, heteroarylalkyl, heterocycloalkyl, and heterocycloalkenyl; and with the proviso that when $R_4$ is Br, $R_{10}$ may not be unsubstituted phenyl.

15. The pharmaceutical composition of claim 1, wherein the salt is selected from the group consisting of acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, malate, maleate, methanesulfonate, 2-naphthalenesulfonate, nicotinate, oxalate, thiocyanate, tosylate, undecanoate, lithium, sodium, calcium, potassium, aluminum, ammonium, tetraethylammonium, methylammonium, dimethylammonium, N-methylmorpholinium, and ethanolammonium.

16. The pharmaceutical composition of claim 1, wherein the pharmaceutical composition is a solid.

*17. The method of claim 5, wherein the patient is a human.*

*18. The method of claim 9, wherein the patient is a human.*

* * * * *